(12) United States Patent
Funahashi

(10) Patent No.: US 8,512,878 B2
(45) Date of Patent: Aug. 20, 2013

(54) DIAMINOPYRENE DERIVATIVE AND ORGANIC EL DEVICE USING THE SAME

(75) Inventor: Masakazu Funahashi, Sodegaura-shi (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 800 days.

(21) Appl. No.: 12/599,274

(22) PCT Filed: May 7, 2008

(86) PCT No.: PCT/JP2008/058481
§ 371 (c)(1),
(2), (4) Date: Nov. 6, 2009

(87) PCT Pub. No.: WO2008/136522
PCT Pub. Date: Nov. 13, 2008

(65) Prior Publication Data
US 2011/0193064 A1    Aug. 11, 2011

(30) Foreign Application Priority Data

May 8, 2007 (JP) .................................. 2007-123215

(51) Int. Cl.
*H01L 51/54* (2006.01)
*C07C 211/57* (2006.01)
*C07D 401/10* (2006.01)
*C07F 7/02* (2006.01)
*C07F 7/30* (2006.01)

(52) U.S. Cl.
USPC ........... 428/690; 428/917; 313/504; 313/506; 564/434; 546/264; 546/167; 546/14; 546/88; 556/413; 556/81

(58) Field of Classification Search
None
See application file for complete search history.

(56) References Cited

U.S. PATENT DOCUMENTS 7,651,786 B2 * 1/2010 Matsuura et al. ............. 428/690
7,700,201 B2 * 4/2010 Seo et al. ...................... 428/690

(Continued)

FOREIGN PATENT DOCUMENTS

JP    2002063988 A    2/2002
JP    2002324678 A    11/2002

(Continued)

OTHER PUBLICATIONS

Translation for JP 2006-273791, which was published Oct. 2006.*

*Primary Examiner* — Dawn L Garrett
(74) *Attorney, Agent, or Firm* — Foley & Lardner LLP

(57) ABSTRACT

An organic EL device is provided that includes an emitting layer provided between an anode and a cathode. The emitting layer contains a diaminopyrene derivative represented by the following formula (1) as an emitting material for the organic EL device. The diaminopyrene derivative emits light with electrical energy.

25 Claims, 5 Drawing Sheets (1)

(56) References Cited

U.S. PATENT DOCUMENTS

| | | |
|---|---|---|
| 7,705,183 B2 * | 4/2010 | Funahashi et al. ............. 564/308 |
| 7,732,063 B2 * | 6/2010 | Matsuura et al. ............ 428/690 |
| 7,981,523 B2 * | 7/2011 | Hosokawa et al. ........... 428/690 |
| 2003/0118866 A1 * | 6/2003 | Oh et al. ....................... 428/690 |
| 2006/0040131 A1 * | 2/2006 | Klubek et al. ................ 428/690 |
| 2007/0087222 A1 * | 4/2007 | Kim et al. ..................... 428/690 |
| 2007/0114917 A1 * | 5/2007 | Funahashi et al. ............. 313/504 |
| 2007/0252511 A1 * | 11/2007 | Funahashi ..................... 313/498 |
| 2009/0134781 A1 * | 5/2009 | Jang et al. ..................... 313/504 |
| 2011/0156016 A1 * | 6/2011 | Kawamura et al. ............. 257/40 |

FOREIGN PATENT DOCUMENTS

| | | |
|---|---|---|
| JP | 2004204238 A | 7/2004 |
| JP | 2004356033 A | 12/2004 |
| JP | 2006273791 A | 10/2006 |
| WO | 2005061656 A1 | 7/2005 |
| WO | 2005108348 A1 | 11/2005 |
| WO | 2005115950 A1 | 12/2005 |
| WO | 2006051649 A1 | 5/2006 |

* cited by examiner

DIAMINOPYRENE DERIVATIVE AND ORGANIC EL DEVICE USING THE SAME

CROSS-REFERENCE TO PRIOR APPLICATION

This is the U.S. National Phase Application under 35 U.S.C. §371 of International Patent Application No. PCT/JP2008/058481 filed May 7, 2008, which claims the benefit of Japanese Patent Application No. 2007-123215 filed May 8, 2007, both of which are incorporated by reference herein. The International Application was published in Japanese on November 13, as WO2007/136522 A1 under PCT Article 21(2).

TECHNICAL FIELD

The present invention relates to a novel diaminopyrene derivative and an organic EL device using the same.

BACKGROUND ART

Organic EL devices, which utilize emission of organic compounds, are known.

Such an organic EL device includes a plurality of organic thin films layered between an anode and a cathode. In this structure, voltage is applied between the anode and cathode. Then, holes and electrons are injected into the organic thin films respectively from the anode and cathode. The injected holes and electrons generate excited-state molecules in an emitting layer within the organic thin films. Energy generated when the molecules return to the ground state from the excited state is emitted as light.

As an emitting material having high luminous efficiency, high luminance and excellent color purity, pyrene derivatives are known (e.g., Patent Document 1).

However, pyrene skeletons exhibit high crystallinity due to their high planarity, so that crystallization tends to progress during an amorphous thin-film state and driving of the device. Destruction of thin films by crystallization leads to reduction in luminance or non-emission. When planarity of molecules is high, molecular aggregate is easily generated. Fluorescence obtained from molecular aggregate is unfavorably of longer wavelength than fluorescence obtained from a single molecule.

In view of the above, a known method makes a pyrene derivative sterically bulky by introducing substituents in the pyrene skeleton and thereby suppresses crystallization and molecular aggregate.

For instance, Patent Document 2 discloses diaminopyrene derivatives, and Patent Document 3 discloses diaminopyrene derivatives in which alkyl groups or aryl groups are introduced into the pyrene skeletons.

Patent Document 1: JP-A-2002-063988
Patent Document 2: JP-A-2004-204238
Patent Document 3: WO2005/108348

DISCLOSURE OF THE INVENTION

Problems to be Solved by the Invention

When organic EL devices are produced by using the diaminopyrene derivatives disclosed in Patent Document 2 as the dopants, increase in luminous efficiency can be anticipated. However, prevention of molecular aggregate and crystallization is not sufficient, and lifetime of such an organic EL device is short.

The diaminopyrene derivatives disclosed in Patent Document 3 can suppress molecular aggregate and crystallization, so that organic EL devices having high luminance, high luminous efficiency and long lifetime are obtainable. However, by the introduction of substituents into the pyrene skeletons, the obtained emission tends to be of long wavelength. Accordingly, when the diaminopyrene derivatives of Patent Document 3 are used, short-wavelength blue light of high color purity has been hardly obtainable.

For the solution of the above problems, an object of the invention is to provide an organic EL device having high luminance, high luminous efficiency and long lifetime, and to provide diaminopyrene derivatives usable in such an organic EL device.

Means for Solving the Problems

A diaminopyrene derivative for use as an emitting material for organic EL devices according to an aspect of the invention is represented by the following formula (1).

[Chemical Formula 1]

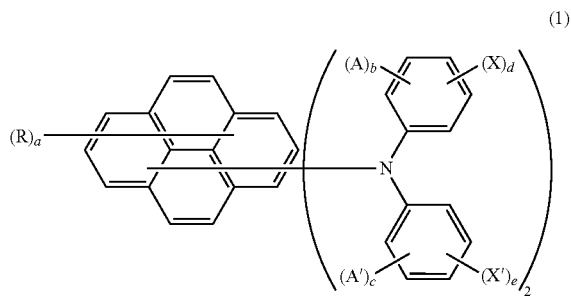

In the formula, R represents a substituted or unsubstituted alkyl group having 1 to 20 carbon atoms, substituted or unsubstituted aryl group having 5 to 25 carbon atoms, substituted or unsubstituted aralkyl group having 6 to 25 carbon atoms, substituted or unsubstituted cycloalkyl group having 3 to 25 carbon atoms, substituted or unsubstituted alkoxyl group having 3 to 20 carbon atoms, substituted or unsubstituted aryloxy group having 5 to 25 carbon atoms, substituted or unsubstituted arylamino group having 5 to 20 carbon atoms, fluorine atom, substituted or unsubstituted alkylamino group having 1 to 20 carbon atoms or cyano group. a represents an integer of 1 to 9. When a is 2 or more, the plurality of R may be mutually the same or different.

A and A' each independently represent a hydrogen atom, substituted or unsubstituted alkyl group having 1 to 20 carbon atoms, substituted or unsubstituted aryl group having 5 to 25 carbon atoms, substituted or unsubstituted aralkyl group having 6 to 25 carbon atoms, substituted or unsubstituted cycloalkyl group having 3 to 25 carbon atoms, substituted or unsubstituted alkoxyl group having 1 to 20 carbon atoms, substituted or unsubstituted aryloxy group having 5 to 25 carbon atoms, substituted or unsubstituted arylamino group having 5 to 25 carbon atoms, substituted or unsubstituted alkylamino group having 1 to 20 carbon atoms, fluorine atom or cyano group.

b and c each represent an integer of 1 to 5 while $b+c \leqq 9$ is satisfied. When b is 2 or more, the plurality of A may be mutually the same or different and may be bonded together to form a saturated or unsaturated ring. When c is 2 or more, the plurality of A' may be mutually the same or different and may be bonded together to form a saturated or unsaturated ring.

X and X' each independently represent a substituent containing at least one of Ge, P, B and Si.

d and e each represent an integer of 0 to 5 while d+e≧1 is satisfied. When d is 2 or more, the plurality of X may be mutually the same or different and may be bonded together to form a saturated or unsaturated ring. When e is 2 or more, the plurality of X' may be mutually the same or different and may be bonded together to form a saturated or unsaturated ring.

According to the aspect of the invention, since the pyrene skeleton of the diaminopyrene derivative is bonded with two amino groups, increase in luminous efficiency can be anticipated in an organic EL device in which the diaminopyrene derivative is used as the dopant. The amino groups bonded to the pyrene skeleton are diphenylamino groups having substituents of A, A', X and X', and thus the long lifetime can be realized.

In addition, the pyrene skeleton is bonded with a substituent of R. Thus, molecular aggregate and crystallization of the diaminopyrene derivative can be suppressed, and reduction in luminance and non-emission can be prevented.

The diaminopyrene derivative according to the aspect of the invention has substituents containing at least one of Ge, P, B and Si as the substituents of X and X' bonded to the diphenylamino group.

The introduction of substituents can prevent aggregate, but typically increases the wavelength of the emission, which is unfavorable when blue emission of short wavelength and pure color is desired.

In this respect, the substituents containing at least one of Ge, P, B and Si have been found less influential on the wavelength of the emission.

Hence, remarkably, the diaminopyrene derivative according to the aspect of the invention can not only have a long lifetime due to the prevention of the aggregate by the introduction of the substituents, but also provide color emission of high color purity.

Accordingly, the diaminopyrene derivative according to the aspect of the invention is usable as the emitting material for organic EL devices having high luminance, high luminous efficiency, long lifetime and high color purity.

Incidentally, d and e are preferably 1 or more. At this time, aggregate can be prevented while increase in the wavelength of the emission is more effectively suppressed.

The diaminopyrene derivative as the emitting material for organic EL devices according to the aspect of the invention is preferably a compound represented by the following formula (2) among compounds represented by the formula (1).

[Chemical Formula 2]

(2)

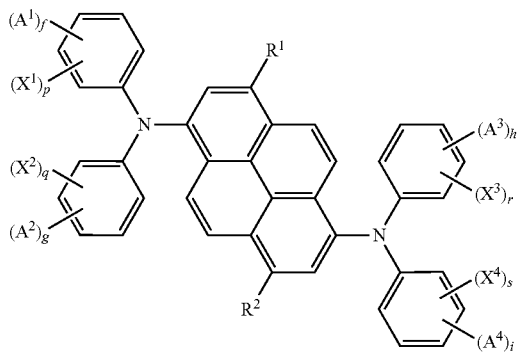

In the formula, $R^1$ and $R^2$ each independently represent a hydrogen atom, substituted or unsubstituted alkyl group having 1 to 20 carbon atoms, substituted or unsubstituted aryl group having 5 to 25 carbon atoms, substituted or unsubstituted aralkyl group having 6 to 25 carbon atoms, substituted or unsubstituted cycloalkyl group having 3 to 25 carbon atoms, substituted or unsubstituted alkoxyl group having 3 to 20 carbon atoms, substituted or unsubstituted aryloxy group having 5 to 25 carbon atoms, substituted or unsubstituted arylamino group having 5 to 20 carbon atoms, substituted or unsubstituted alkylamino group having 1 to 20 carbon atoms, fluorine atom or cyano group. However, $R^1$ and $R^2$ do not both represent a hydrogen atom.

$A^1, A^2, A^3$ and $A^4$ each independently represent a hydrogen atom, substituted or unsubstituted alkyl group having 1 to 20 carbon atoms, substituted or unsubstituted aryl group having 5 to 25 carbon atoms, substituted or unsubstituted aralkyl group having 6 to 25 carbon atoms, substituted or unsubstituted cycloalkyl group having 3 to 25 carbon atoms, substituted or unsubstituted alkoxyl group having 1 to 20 carbon atoms, substituted or unsubstituted aryloxy group having 5 to 25 carbon atoms, substituted or unsubstituted arylamino group having 5 to 25 carbon atoms, substituted or unsubstituted alkylamino group having 1 to 20 carbon atoms or cyano group.

f, g, h and i each represent an integer of 1 to 5 while f+g+h+i≦19 is satisfied. When f is 2 or more, the plurality of $A^1$ may be mutually the same or different and may be bonded together to form a saturated or unsaturated ring. When g is 2 or more, the plurality of $A^2$ may be mutually the same or different and may be bonded together to form a saturated or unsaturated ring. When h is 2 or more, the plurality of $A^3$ may be mutually the same or different and may be bonded together to form a saturated or unsaturated ring. When i is 2 or more, the plurality of $A^4$ may be mutually the same or different and may be bonded together to form a saturated or unsaturated ring.

$X^1, X^2, X^3$ and $X^4$ each independently represent a substituent containing at least one of Ge, P, B and Si.

p, q, r and s each represent an integer of 0 to 5 while p+q+r+s≧1 is satisfied. When p is 2 or more, the plurality of $X^1$ may be mutually the same or different and may be bonded together to form a saturated or unsaturated ring. When q is 2 or more, the plurality of $X^2$ may be mutually the same or different and may be bonded together to form a saturated or unsaturated ring. When r is 2 or more, the plurality of $X^3$ may be mutually the same or different and may be bonded together to form a saturated or unsaturated ring. When s is 2 or more, the plurality of $X^4$ may be mutually the same or different and may be bonded together to form a saturated or unsaturated ring.

According to the aspect of the invention, since the pyrene skeleton of the diaminopyrene derivative is bonded with two amino groups, increase in luminous efficiency can be anticipated in an organic EL device in which the diaminopyrene derivative is used as the dopant. The amino groups bonded to the pyrene skeleton are diphenylamino groups having substituents of $A^1, A^2, A^3, A^4, X^1, X^2, X^3$ and $X^4$, and thus the long lifetime can be realized.

In addition, the pyrene skeleton is bonded with substituents of $R^1$ and $R^2$. Thus, molecular aggregate and crystallization of the diaminopyrene derivative can be suppressed, and reduction in luminance and non-emission can be prevented.

The diaminopyrene derivative according to the aspect of the invention has substituents containing at least one of Ge, P, B and Si as the substituents of $X^1, X^2, X^3$ and $X^4$ bonded to the diphenylamino group.

As described above, the substituent containing at least one of Ge, P, B and Si is less influential over the wavelength of the emission. Hence, remarkably, the diaminopyrene derivative according to the aspect of the invention can not only have a long lifetime due to the prevention of the aggregate by the introduction of the substituents, but also provide blue emission of pure color.

Accordingly, the diaminopyrene derivative according to the aspect of the invention is usable as the emitting material for organic EL devices having high luminance, high luminous efficiency, long lifetime and high color purity.

Incidentally, p, q, r and s are preferably 1 or more. At this time, aggregate can be prevented while increase in the wavelength of the emission is more effectively suppressed.

Preferably in the aspect of the invention, $X^1$, $X^2$, $X^3$ and $X^4$ in the formula (2) each independently represent a substituent represented by the following formula (3).

-M(-R³)₃      (3)

In the formula, M represents Ge or Si.

$R^3$ represents hydrogen, a substituted or unsubstituted alkyl group having 1 to 20 carbon atoms, substituted or unsubstituted aryl group having 5 to 25 carbon atoms, substituted or unsubstituted aralkyl group having 6 to 25 carbon atoms, substituted or unsubstituted cycloalkyl group having 3 to 25 carbon atoms, substituted or unsubstituted alkoxyl group having 3 to 20 carbon atoms, substituted or unsubstituted aryloxy group having 5 to 25 carbon atoms, substituted or unsubstituted arylamino group having 5 to 20 carbon atoms, substituted or unsubstituted alkylamino group having 1 to 20 carbon atoms or cyano group.

The plurality of $R^3$ may be mutually the same or different and may be bonded together to form a saturated or unsaturated ring.

The above-described structure can more effectively suppress increase in the wavelength of the emission.

M is particularly preferably Si.

Patent Document 2, for instance, discloses a diaminopyrene derivative having a diphenylamino group substituted by a silyl group and an organic EL device containing the same as the dopant and being excellent in color purity and luminous efficiency.

However, the diaminopyrene derivative disclosed in Patent Document 2 is not structured such that substituents such as $R^1$ and $R^2$ are introduced in the pyrene skeleton. Thus, suppression of molecular aggregate and crystallization is insufficient, and reduction in luminance and non-emission cannot be prevented.

In the aspect of the invention, $X^1$, $X^2$, $X^3$ and $X^4$ in the formula (2) may each independently represent a substituent represented by the following formula (4) alternatively.

-M(-R⁴)₂      (4)

In the formula, M represents P or B.

$R^4$ represents hydrogen, a substituted or unsubstituted alkyl group having 1 to 20 carbon atoms, substituted or unsubstituted aryl group having 5 to 25 carbon atoms, substituted or unsubstituted aralkyl group having 6 to 25 carbon atoms, substituted or unsubstituted cycloalkyl group having 3 to 25 carbon atoms, substituted or unsubstituted alkoxyl group having 3 to 20 carbon atoms, substituted or unsubstituted aryloxy group having 5 to 25 carbon atoms, substituted or unsubstituted arylamino group having 5 to 20 carbon atoms, substituted or unsubstituted alkylamino group having 1 to 20 carbon atoms or cyano group.

The plurality of $R^4$ may be mutually the same or different and may be bonded together to form a saturated or unsaturated ring.

The above-described structure can also more effectively suppress increase in the wavelength of the emission.

In the aspect of the invention, at least either one of $R^1$ and $R^2$ in the formula (2) is preferably a substituted or unsubstituted alkyl group having 1 to 20 carbon atoms.

With this structure, the introduction of $R^1$ and $R^2$ into the pyrene skeleton is less likely to increase the wavelength of the emission, and emission of high color purity can be obtained.

In the aspect of the invention, at least either one of $R^1$ and $R^2$ in the formula (2) is preferably a substituted or unsubstituted aryl group having 5 to 25 carbon atoms.

Alternatively, at least either one of $R^1$ and $R^2$ in the formula (2) is preferably a substituted or unsubstituted cycloalkyl group having 3 to 25 carbon atoms.

With this structure, emission of high color purity (e.g., green emission of high color purity) can be obtained.

Specifically, when at least either one of $R^1$ and $R^2$ is a substituent having a ring structure, some increase in the wavelength of the emission is not avoidable. Nevertheless, green or red light, of which wavelength is longer than that of blue light, can still be emitted at high color purity. Thus, the diaminopyrene derivative according to the aspect of the invention is still usable as the emitting material for organic EL devices having high luminance, high luminous efficiency, long lifetime and high color purity.

At this time, by changing the structures of the substituents of $R^1$ and $R^2$ or by arranging both of $R^1$ and $R^2$ to be substituents having ring structures, the wavelength of the emission can be adjusted in accordance with the desired color of emission.

A diaminopyrene derivative (i.e., an emitting material for organic EL devices) according to an aspect of the invention is represented by the following formula (5).

[Chemical Formula 3]

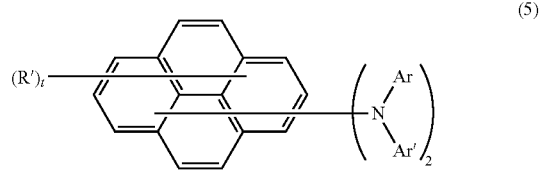

(5)

In the formula, R' represents a substituted or unsubstituted alkyl group having 1 to 20 carbon atoms, substituted or unsubstituted aryl group having 5 to 25 carbon atoms, substituted or unsubstituted aralkyl group having 6 to 25 carbon atoms, substituted or unsubstituted cycloalkyl group having 3 to 25 carbon atoms, substituted or unsubstituted alkoxyl group having 3 to 20 carbon atoms, substituted or unsubstituted aryloxy group having 5 to 25 carbon atoms, substituted or unsubstituted arylamino group having 5 to carbon atoms, fluorine atom, substituted or unsubstituted alkylamino group having 1 to 20 carbon atoms or cyano group. t represents an integer of 1 to 9. When t is 2 or more, the plurality of R' may be mutually the same or different.

Ar and Ar' each independently represent a substituted or unsubstituted alkyl group having 1 to 20 carbon atoms, substituted or unsubstituted aryl group having 5 to carbon atoms, substituted or unsubstituted aralkyl group having 6 to 25 carbon atoms, substituted or unsubstituted cycloalkyl group having 3 to 25 carbon atoms, substituted or unsubstituted alkoxyl group having 1 to 20 carbon atoms, substituted or unsubstituted aryloxy group having 5 to 25 carbon atoms, substituted or unsubstituted arylamino group having 5 to 25 carbon atoms, substituted or unsubstituted alkylamino group having 1 to 20 carbon atoms or substituted or unsubstituted nitrogen-containing heterocyclic group having 5 to 25 atoms for forming the ring.

Two Ar and two Ar' may be mutually the same or different.

However, at least one of Ar and Ar' is a substituted or unsubstituted nitrogen-containing heterocyclic group having 5 to 25 ring atoms.

According to the aspect of the invention, since the pyrene skeleton of the diaminopyrene derivative is bonded with two amino groups, increase in luminous efficiency can be anticipated in an organic EL device in which the diaminopyrene derivative is used as the dopant.

Since the amino groups bonded to the pyrene skeleton has the substituents of Ar and Ar', the lifetime of the emitting material can be increased while aggregate is prevented.

In addition, the pyrene skeleton is bonded with a substituent of R'. Thus, molecular aggregate and crystallization of the diaminopyrene derivative can be suppressed, and reduction in luminance and non-emission can be prevented.

At least one of Ar and Ar' is the nitrogen-containing heterocyclic group.

By using the heterocyclic group as the substituent, the wavelength of the emission can be reduced. Thus, reduction in the wavelength of the emission, as well as the prevention of aggregate, can be realized. This is particularly advantageous in providing a blue-emitting material.

Accordingly, the diaminopyrene derivative according to the aspect of the invention is usable as the emitting material for organic EL devices having high luminance, high luminous efficiency, long lifetime and high color purity.

The diaminopyrene derivative as the emitting material for organic EL devices according to the aspect of the invention is preferably a compound represented by the following formula (6) among the compounds represented by the formula (5).

[Chemical Formula 4]

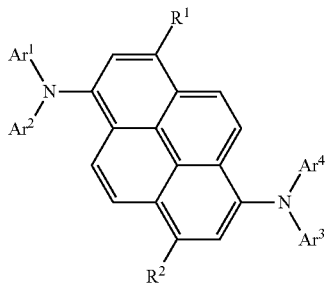

(6)

In the formula, $R^1$ and $R^2$ each independently represent a hydrogen atom, substituted or unsubstituted alkyl group having 1 to 20 carbon atoms, substituted or unsubstituted aryl group having 5 to 25 carbon atoms, substituted or unsubstituted aralkyl group having 6 to 25 carbon atoms, substituted or unsubstituted cycloalkyl group having 3 to 25 carbon atoms, substituted or unsubstituted alkoxyl group having 3 to 20 carbon atoms, substituted or unsubstituted aryloxy group having 5 to 25 carbon atoms, substituted or unsubstituted arylamino group having 5 to 20 carbon atoms, substituted or unsubstituted alkylamino group having 1 to 20 carbon atoms, fluorine atom or cyano group. However, $R^1$ and $R^2$ do not both represent a hydrogen atom.

$Ar^1$, $Ar^2$, $Ar^3$ and $Ar^4$ each independently represent a substituted or unsubstituted alkyl group having 1 to 20 carbon atoms, substituted or unsubstituted aryl group having 5 to 25 carbon atoms, substituted or unsubstituted aralkyl group having 6 to 25 carbon atoms, substituted or unsubstituted cycloalkyl group having 3 to 25 carbon atoms, substituted or unsubstituted alkoxyl group having 1 to 20 carbon atoms, substituted or unsubstituted aryloxy group having 5 to 25 carbon atoms, substituted or unsubstituted arylamino group having 5 to 25 carbon atoms, substituted or unsubstituted alkylamino group having 1 to 20 carbon atoms or substituted or unsubstituted nitrogen-containing heterocyclic group having 5 to 25 atoms for forming the ring. However, at least one of $Ar^1$, $Ar^2$, $Ar^3$ and $Ar^4$ is a substituted or unsubstituted nitrogen-containing heterocyclic group having 5 to 25 ring atoms.

According to the aspect of the invention, since the pyrene skeleton of the diaminopyrene derivative is bonded with two amino groups, increase in luminous efficiency can be anticipated in an organic EL device in which the diaminopyrene derivative is used as the dopant. Since the amino groups bonded to the pyrene skeleton have the substituents of $Ar^1$, $Ar^2$, $Ar^3$ and $Ar^4$, lifetime of the emission can be increased.

In addition, the pyrene skeleton is bonded with substituents of $R^1$ and $R^2$. Thus, molecular aggregate and crystallization of the diaminopyrene derivative can be suppressed, and reduction in luminance and non-emission can be prevented.

Further, at least one of $Ar^1$, $Ar^2$, $Ar^3$ and $Ar^4$ is the nitrogen-containing heterocyclic group.

By using the heterocyclic group as the substituent, the wavelength of the emission can be reduced. Thus, reduction in the wavelength of the emission, as well as the prevention of aggregate, can be realized. This is particularly advantageous in providing a blue-emitting material. Accordingly, the diaminopyrene derivative according to the aspect of the invention is usable as the emitting material for organic EL devices having high luminance, high luminous efficiency, long lifetime and high color purity.

In the aspect of the invention, at least either one of $R^1$ and $R^2$ in the formula (6) is preferably a substituted or unsubstituted alkyl group having 1 to 20 carbon atoms.

With this structure, the introduction of $R^1$ and $R^2$ into the pyrene skeleton is less likely to increase the wavelength of the emission, and emission of high color purity can be obtained.

In the aspect of the invention, at least either one of $R^1$ and $R^2$ in the formula (6) is preferably a substituted or unsubstituted aryl group having 5 to 25 carbon atoms.

Alternatively, at least either one of $R^1$ and $R^2$ in the formula (6) is preferably a substituted or unsubstituted cycloalkyl group having 3 to 25 carbon atoms.

With this structure, emission of high color purity (e.g., green emission of high color purity) can be obtained.

Specifically, when at least either one of $R^1$ and $R^2$ is a substituent having a ring structure, some increase in the wavelength of the emission is not avoidable. Nevertheless, green or red light, of which wavelength is longer than that of blue light, can still be emitted at high color purity. Accordingly, the diaminopyrene derivative according to the aspect of the invention is still usable as the emitting material for organic EL devices having high luminance, high luminous efficiency, long lifetime and high color purity.

At this time, by changing the structures of the substituents of $R^1$ and $R^2$ or by arranging both of $R^1$ and $R^2$ to be substituents having ring structures, the wavelength of the emission can be adjusted in accordance with the desired color of emission.

The diaminopyrene derivative according to the aspect of the invention is preferably used as a dopant of an emitting layer of an organic EL device, in which a host and the dopant are contained.

The diaminopyrene derivative according to the aspect of the invention, which has excellent capability of injecting and transporting the holes from a metal electrode or organic thin films and also of injecting and transporting the electrons from a metal electrode and organic thin films, is favorably usable as the dopant of organic EL devices. Thus, organic EL devices having high luminance, high luminous efficiency, long lifetime and high color purity are obtainable.

The diaminopyrene derivative is also usable alone as the emitting material.

An organic EL device according to another aspect of the invention includes an organic layer placed between a cathode and an anode, in which the organic layer contains the above-described diaminopyrene derivative.

An organic EL device according to still further aspect of the invention includes an emitting layer placed between a cathode and an anode, in which the emitting layer contains the above-described diaminopyrene derivative.

The organic EL device according to the aspect of the invention contains the above-described diaminopyrene derivative, so that the luminance, luminous efficiency, color purity and lifetime can be enhanced.

In the aspect of the invention, the emitting layer preferably contains: the above-described diaminopyrene derivative as a dopant; and a compound having a central anthracene skeleton represented by the following formula (7) as a host.

[Chemical Formula 5]

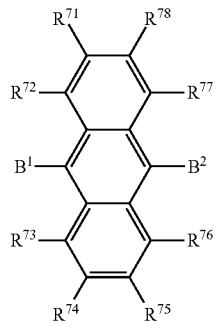

(7)

In the formula, $B^1$ and $B^2$ each independently represent a group induced from a substituted or unsubstituted aromatic ring having 6 to 20 carbon atoms for forming the ring.

The aromatic ring may be substituted by 1 or more substituent.

The substituent is selected from a substituted or unsubstituted aryl group having 6 to 50 carbon atoms for forming the ring, substituted or unsubstituted alkyl group having 1 to 50 carbon atoms, substituted or unsubstituted cycloalkyl group having 3 to 50 carbon atoms, substituted or unsubstituted alkoxy group having 1 to 50 carbon atoms, substituted or unsubstituted aralkyl group having 6 to 50 carbon atoms, substituted or unsubstituted aryloxy group having 5 to 50 atoms for forming the ring, substituted or unsubstituted arylthio group having 5 to 50 atoms for forming the ring, substituted or unsubstituted alkoxycarbonyl group having 1 to 50 carbon atoms, substituted or unsubstituted silyl group, carboxyl group, halogen atom, cyano group, nitro group and hydroxyl group.

When the aromatic ring is substituted by 2 or more substituents, the substituents may be the same or different. Alternatively, the adjacent substituents may be bonded together to form a saturated or unsaturated ring structure.

$R^{71}$ to $R^{78}$ are each independently selected from a hydrogen atom, substituted or unsubstituted aryl group having 6 to 50 carbon atoms for forming the ring, substituted or unsubstituted heteroaryl group having 5 to 50 atoms for forming the ring, substituted or unsubstituted alkyl group having 1 to 50 carbon atoms, substituted or unsubstituted cycloalkyl group having 3 to 50 carbon atoms, substituted or unsubstituted alkoxy group having 1 to 50 carbon atoms, substituted or unsubstituted aralkyl group having 6 to 50 carbon atoms, substituted or unsubstituted aryloxy group having 5 to 50 atoms for forming the ring, substituted or unsubstituted arylthio group having 5 to 50 atoms for forming the ring, substituted or unsubstituted alkoxycarbonyl group having 1 to 50 carbon atoms, substituted or unsubstituted silyl group, carboxyl group, halogen atom, cyano group, nitro group and hydroxyl group.

In the formula (7), $B^1$ and $B^2$ are preferably different from each other.

In the aspect of the invention, the emitting layer preferably contains: the above-described diaminopyrene derivative as a dopant; and a compound having a central pyrene skeleton represented by the following formula (8) as a host.

[Chemical Formula 6]

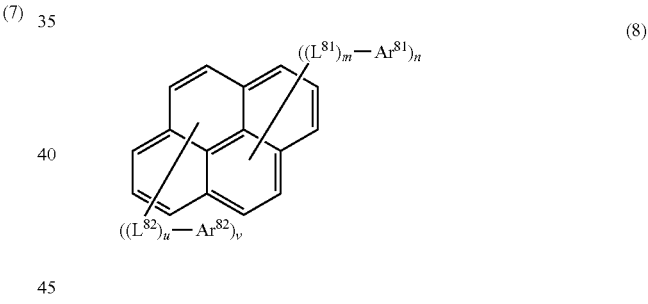

(8)

In the formula, $Ar^{81}$ and $Ar^{82}$ each independently represent a substituted or unsubstituted aryl group having 6 to 50 carbon atoms for forming the ring.

$L^{81}$ and $L^{82}$ are each independently selected from a substituted or unsubstituted phenylene group, substituted or unsubstituted naphthalenylene group, substituted or unsubstituted fluorenylene group and substituted or unsubstituted dibenzosylolylene group.

m represents an integer of 0 to 2, n represents an integer of 1 to 4, u represents an integer of 0 to 2, and v represents an integer of 0 to 4.

$L^{81}$ or $Ar^{81}$ is bonded to the pyrene in one of 1st to 5th positions, and $L^{82}$ or $Ar^{82}$ is bonded to the pyrene in one of 6th to 10th positions.

In the aspect of the invention, the emitting layer preferably contains: the above-described diaminopyrene derivative as a dopant; and a compound having a triphenylamine skeleton represented by the following formula (9) as a host material.

[Chemical Formula 7]

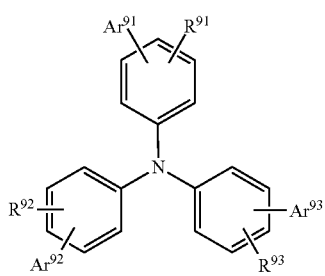

(9)

In the formula, $Ar^{91}$, $Ar^{92}$ and $Ar^{93}$ are each independently selected from a group having an anthracene structure, a group having a phenanthrene structure and a group having a pyrene structure.

$R^{91}$, $R^{92}$ and $R^{93}$ each independently represent a hydrogen atom or a substituent.

In the aspect of the invention, the emitting layer preferably contains: the above-described diaminopyrene derivative; and a compound having a structure represented by the following formula (10).

[Chemical Formula 8]

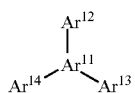

(10)

In the formula, $Ar^{12}$, $Ar^{13}$ and $Ar^{14}$ each independently represent an aryl group having 6 to 50 carbon atoms for forming the ring.

The aryl group may be substituted by 1 or more substituent(s).

At least one of $Ar^{12}$, $Ar^{13}$, $Ar^{14}$ and substituents for these aryl groups has a ring-fused aryl structure having 10 to 20 carbon atoms for forming the ring or a ring-fused heteroaryl structure having 6 to 20 carbon atoms for forming the ring.

$Ar^{11}$ represents a trivalent group induced from an aromatic ring or hetero aromatic ring.

Since the emitting layer contains the compound represented by the formula (7) to (10) in the above-described structure, further enhancement can be realized in the luminance, luminous efficiency, color purity and lifetime.

In the organic EL device according to the aspect of the invention, the emitting layer preferably contains the diaminopyrene derivative according to the aspect of the invention at 0.01 to 20 mass %, more preferably at 0.5 to 20 mass %. The content of the diaminopyrene derivative is further preferably 1 mass % to 20 mass %, much more preferably 5 mass % to 20 mass %.

Considerably advantageously, when the diaminopyrene derivative according to the aspect of the invention is used for the dopant, the doping concentration can be set higher than that of a typical dopant.

It is typically known that increase in the doping concentration may bring about concentration quenching. In this respect, since molecular aggregate is prevented by effectively introducing substituents in the diaminopyrene derivative according to the aspect of the invention, increase in the doping concentration does not bring about concentration quenching, and high luminous efficiency can be maintained.

Further, the increase in the doping concentration can increase the lifetime of the emission.

Typically, the introduction of substituents leads to increase in the wavelength of the emission. Thus, the enhancement of luminous efficiency by the prevention of molecular aggregate and the increase in lifetime by high-concentration doping have a trade-off relationship with obtainment of short-wavelength color emission.

Therefore, it has been particularly difficult to obtain a blue material having long lifetime and high efficiency.

In this respect, the diaminopyrene derivative according to the aspect of the invention can realize high luminous efficiency, while molecular aggregate is prevented by effectively introducing the substituents and doping is of high concentration.

Thus, remarkably, increase in the lifetime can also be realized by the high-concentration doping.

In the manufacturing process of devices, a mass ratio of the host to the dopant is controllable by controlling the deposition rates of the host and the dopant. Alternatively, when the emitting layers are formed by coating, the host/dopant ratio in the emitting layer is controllable by controlling the ratio of the host to the dopant contained in the coating agent.

The inspection of the host/dopant ratio in the emitting layer of the manufactured device may be exemplarily conducted by removing the emitting layer of the device, dissolving it in a solvent, separating the content in a column of liquid chromatography and determining the mass ratio based on the respective peak heights. However, the inspection is not limited to the above method but may be conducted by any other method as long as the host/dopant ratio in the emitting layer can be measured.

BEST MODE FOR CARRYING OUT THE INVENTION

Preferred exemplary embodiments of the invention will be described below.

[Organic EL Device]

Figure 1:
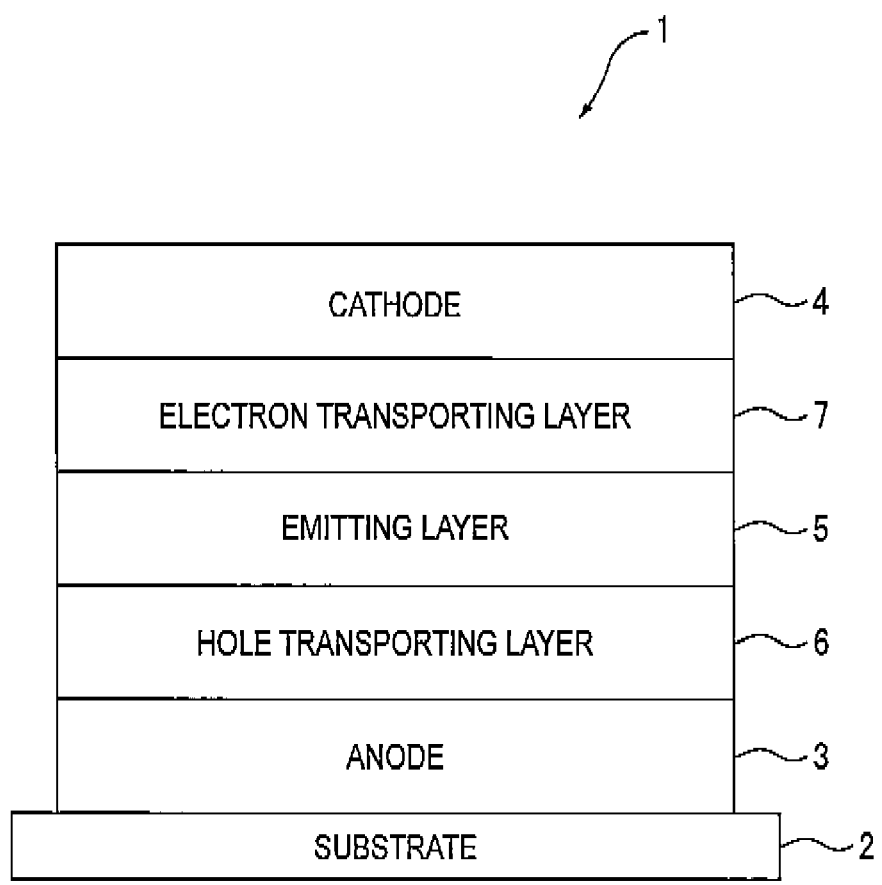
FIG. 1 schematically shows an arrangement of an organic EL device according to an exemplary embodiment of the invention.

As shown in FIG. 1, an organic EL device 1 according to the aspect of the invention at least includes a transparent substrate 2, anode 3, cathode 4 and emitting layer 5 placed between the anode 3 and the cathode 4. As a matter of course, the organic EL device 1 may further include a hole transporting layer 6 placed between the emitting layer 5 and the anode 3 and an electron transporting layer 7 placed between the emitting layer 5 and the cathode 4.

The emitting layer 5 contains a host and a dopant.

[Diaminopyrene Derivative]

The dopant of the emitting layer 5, i.e., the diaminopyrene derivative according to the aspect of the invention used as an emitting material for organic EL device, is represented by the formula (1) above, preferably by the formula (2) above.

In the formulae (1) and (2), $R^1$ and $R^2$ each independently represent a hydrogen atom, substituted or unsubstituted alkyl group having 1 to 20 carbon atoms (preferably 1 to 6 carbon atoms), substituted or unsubstituted aryl group having 5 to 25 carbon atoms (preferably 5 to 10 carbon atoms), substituted or unsubstituted aralkyl group having 6 to 25 carbon atoms (preferably 6 to 10 carbon atoms), substituted or unsubstituted cycloalkyl group having 3 to 25 carbon atoms (preferably 3 to 10 carbon atoms), substituted or unsubstituted alkoxyl group having 3 to 20 carbon atoms (preferably 1 to 6 carbon atoms), substituted or unsubstituted aryloxy group having 5 to 25 carbon atoms (preferably 5 to 10 carbon atoms), substituted or unsubstituted arylamino group having 5 to 20 carbon atoms (preferably 5 to 10 carbon atoms), substituted or unsubstituted alkylamino group having 1 to 20 carbon atoms (preferably 1 to 6 carbon atoms), fluorine atom or cyano group. However, $R^1$ and $R^2$ do not both represent a hydrogen atom.

At least either one of $R^1$ and $R^2$ in the formulae (1) and (2) is preferably a substituted or unsubstituted alkyl group having 1 to 20 carbon atoms (preferably 1 to 6 carbon atoms).

With this structure, the introduction of $R^1$ and $R^2$ into the pyrene skeleton is less likely to increase the wavelength of the emission, and emission of high color purity can be obtained.

However, $R^1$ and $R^2$ in the formulae (1) and (2) are not limited to the above, but at least either one of $R^1$ and $R^2$ may be any one of a substituted or unsubstituted alkyl group having 1 to 20 carbon atoms (preferably 1 to 6 carbon atoms), substituted or unsubstituted aryl group having 5 to 25 carbon atoms (preferably 5 to 10 carbon atoms), substituted or unsubstituted aralkyl group having 6 to 25 carbon atoms (preferably 6 to 10 carbon atoms), substituted or unsubstituted cycloalkyl group having 3 to 25 carbon atoms (preferably 3 to 10 carbon atoms), substituted or unsubstituted aryloxy group having 5 to 25 carbon atoms (preferably 5 to 10 carbon atoms) and substituted or unsubstituted arylamino group having 5 to 20 carbon atoms (preferably 5 to 10 carbon atoms).

Specifically, when at least either one of $R^1$ and $R^2$ is a substituent having a ring structure, some increase in the wavelength of the emission is not avoidable. Nevertheless, green or red light, of which wavelength is longer than that of blue light, can still be emitted at high color purity. Accordingly, the diaminopyrene derivative according to the aspect of the invention is still usable as the emitting material for organic EL devices having high luminance, high luminous efficiency, long lifetime and high color purity.

At least either one of $R^1$ and $R^2$ in the formulae (1) and (2) is preferably a substituted or unsubstituted aryl group having 5 to 25 carbon atoms (preferably 5 to 10 carbon atoms). Alternatively, at least either one of $R^1$ and $R^2$ in the formulae (1) and (2) is preferably a substituted or unsubstituted cycloalkyl group having 3 to 25 carbon atoms (preferably 3 to 10 carbon atoms).

At this time, by changing the structures of the substituents of $R^1$ and $R^2$ or by arranging both of $R^1$ and $R^2$ to be substituents having ring structures, the wavelength of the emission can be adjusted in accordance with the desired color of emission.

Examples of the alkyl group for $R^1$ and $R^2$ are a methyl group, ethyl group, propyl group, isopropyl group, butyl group, sec-butyl group, tert-butyl group, pentyl group, hexyl group, heptyl group, octyl group, stearyl group, 2-phenyl isopropyl group, trichloromethyl group, trifluoromethyl group, benzyl group, α-phenoxybenzyl group, α,α-methylphenylbenzyl group, α,α-ditrifluoromethylbenzyl group, triphenylmethyl group and α-benzyloxybenzyl group. Preferable are an ethyl group, propyl group, isopropyl group, butyl group, sec-butyl group and tert-butyl group.

Examples of the aryl group for $R^1$ and $R^2$ are a phenyl group, 2-methylphenyl group, 3-methylphenyl group, 4-methylphenyl group, 4-ethylphenyl group, 3,4-dimethylphenyl group, 3,4,5-trimethylphenyl group, o-biphenyl group, m-biphenyl group, p-biphenyl group, 4-cyanophenyl group, 3-cyanophenyl group, 4-methylbiphenyl group, 4-ethylbiphenyl group, 4-cyclohexylbiphenyl group, terphenyl group, 3,5-dichlorophenyl group, 1-naphthyl group, 2-naphthyl group, 5-methylnaphthyl group, anthryl group, pyrenyl group, 1,2,3,4-tetrahydronaphthyl group, 2,3-dihydroindanyl group, fluorenyl group and julolidinyl group. More preferable are a phenyl group, 1-naphthyl group and 2-naphthyl group.

Examples of the aralkyl group for $R^1$ and $R^2$ are a benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, o-methylbenzyl group, m-methylbenzyl group, p-chlorobenzyl group, o-chlorobenzyl group, m-chlorobenzyl group, p-bromobenzyl group, o-bromobenzyl group, m-bromobenzyl group, p-iodobenzyl group, o-iodobenzyl group, m-iodobenzyl group, p-hydroxybenzyl group, o-hydroxybenzyl group, m-hydroxybenzyl group, nitrochlorobenzyl group, o-nitrobenzyl group, m-nitrobenzyl group, p-cyanobenzyl group, o-cyanobenzyl group, m-cyanobenzyl group, 1-hydroxy-2-phenylisopropyl group and 1-chloro-2-phenylisopropyl group.

Examples of the cycloalkyl group for $R^1$ and $R^2$ are a cyclopropyl group, cyclobutyl group, cyclopentyl group, cyclohexyl group, norbornene group and adamantyl group.

Examples of the alkoxyl group for $R^1$ and $R^2$ are a methoxy group, ethoxy group, propoxy group, isopropoxy group, butoxy group, isobutoxy group, sec-butoxy group, tert-butoxy group, various pentyloxy groups and various hexyloxy groups.

Examples of the aryloxy group for $R^1$ and $R^2$ are a phenoxy group, tolyloxy group and naphthyloxy group.

Examples of the arylamino group for $R^1$ and $R^2$ are a diphenylamino group, ditolylamino group, isopropyldiphenylamino group, t-butyldiphenylamino group, diisopropyldiphenylamino group, di-t-butyldiphenylamino group, dinaphthylamino group and naphthylphenylamino group.

Examples of the alkylamino group for $R^1$ and $R^2$ are a dimethylamino group, diethylamino group and dihexylamino group.

In the formulae (1) and (2), $A^1$, $A^2$, $A^3$ and $A^4$ each independently represent a hydrogen atom, substituted or unsubstituted alkyl group having 1 to 20 carbon atoms (preferably 1 to 6 carbon atoms), substituted or unsubstituted aryl group having 5 to 25 carbon atoms (preferably 5 to 10 carbon atoms), substituted or unsubstituted aralkyl group having 6 to 25 carbon atoms (preferably 6 to 10 carbon atoms), substituted or unsubstituted cycloalkyl group having 3 to 25 carbon atoms (preferably 3 to 10 carbon atoms), substituted or unsubstituted alkoxyl group having 1 to 20 carbon atoms (preferably 1 to 6 carbon atoms), substituted or unsubstituted aryloxy group having 5 to 25 carbon atoms (preferably 5 to 10 carbon atoms), substituted or unsubstituted arylamino group having 5 to 20 carbon atoms (preferably 5 to 10 carbon atoms), substituted or unsubstituted alkylamino group having 1 to 20 carbon atoms (preferably 1 to 6 carbon atoms) or cyano group.

Examples of the alkyl group, aryl group, aralkyl group, cycloalkyl group, alkoxyl group, aryloxy group, arylamino group and alkylamino group for $A^1$, $A^2$, $A^3$ and $A^4$ are the same as enumerated with respect to $R^1$ and $R^2$.

In the formula (1), a represents an integer of 1 to 9. When a is 2 or more, the plurality of R may be mutually the same or different.

b and c each represent an integer of 1 to 5 while $b+c \leqq 9$ is satisfied. When b is 2 or more, the plurality of A may be mutually the same or different and may be bonded together to form a saturated or unsaturated ring. When c is 2 or more, the plurality of A' may be mutually the same or different and may be bonded together to form a saturated or unsaturated ring.

X and X' each independently represent a substituent containing at least one of Ge, P, B and Si.

d and e each represent an integer of 0 to 5 while $d+e \geqq 1$ is satisfied. When d is 2 or more, the plurality of X may be mutually the same or different and may be bonded together to form a saturated or unsaturated ring. When e is 2 or more, the plurality of X' may be mutually the same or different and may be bonded together to form a saturated or unsaturated ring.

In the formula (2), f, g, h and i each represent an integer of 1 to 5 while $f+g+h+i \leqq 19$ is satisfied. When f is 2 or more, the plurality of $A^1$ may be mutually the same or different and may be bonded together to form a saturated or unsaturated ring. When g is 2 or more, the plurality of $A^2$ may be mutually the same or different and may be bonded together to form a saturated or unsaturated ring. When h is 2 or more, the plurality of $A^3$ may be mutually the same or different and may be bonded together to form a saturated or unsaturated ring. When i is 2 or more, the plurality of $A^4$ may be mutually the same or different and may be bonded together to form a saturated or unsaturated ring.

Examples of the saturated or unsaturated ring are the same as enumerated with respect to the aryl group and cycloalkyl group for $R^1$ and $R^2$.

However, none of the substituents for the groups represented by $A^1$, $A^2$, $A^3$ and $A^4$ is a group containing a vinyl group.

In the formula (2), $X^1$, $X^2$, $X^3$ and $X^4$ each independently represent a substituent containing at least one of Ge, P, B and Si. However, none of the substituents for the groups represented by $X^1$, $X^2$, $X^3$ and $X^4$ is a group containing a vinyl group.

Examples of the substituent containing at least one of Ge, P, B and Si are substituents represented by the formulae (3) and (4). In order to more effectively suppress increase in the wavelength of the emission, the substituent is preferably represented by the formula (3).

In the formulae (3) and (4), $R^3$ and $R^4$ each independently represent a hydrogen atom, substituted or unsubstituted alkyl group having 1 to 20 carbon atoms (preferably 1 to 6 carbon atoms), substituted or unsubstituted aryl group having 5 to 25 carbon atoms (preferably 5 to 10 carbon atoms), substituted or unsubstituted aralkyl group having 6 to 25 carbon atoms (preferably 6 to 10 carbon atoms), substituted or unsubstituted cycloalkyl group having 3 to 25 carbon atoms (preferably 3 to 10 carbon atoms), substituted or unsubstituted alkoxyl group having 1 to 20 carbon atoms (preferably 1 to 6 carbon atoms), substituted or unsubstituted aryloxy group having 5 to 25 carbon atoms (preferably 5 to 10 carbon atoms), substituted or unsubstituted arylamino group having 5 to 20 carbon atoms (preferably 5 to 10 carbon atoms), substituted or unsubstituted alkylamino group having 1 to 20 carbon atoms (preferably 1 to 6 carbon atoms) or cyano group.

Examples of the alkyl group, aryl group, aralkyl group, cycloalkyl group, alkoxyl group, aryloxy group, arylamino group and alkylamino group for $R^3$ and $R^4$ are the same as enumerated with respect to $R^1$ and $R^2$.

The pluralities of $R^3$ and $R^4$ may be mutually the same or different and may be bonded together to form a saturated or unsaturated ring.

M is particularly preferably Si. $R^3$ and $R^4$ are particularly preferably hydrogen or an alkyl group having 1 to 3 carbon atoms. Examples of such a substituent are a silyl group, trimethylsilyl group, triethylsilyl group, tripropylsilyl group, triphenylsilyl group, butyldimethylsilyl group, propyldimethylsilyl group and vinyldimethylsilyl group. In particular, a trimethylsilyl is preferable.

In the formula (2), the substituents of $A^1$, $A^2$, $A^3$, $A^4$, $X^1$, $X^2$, $X^3$ and $X^4$ are preferably bonded in meta positions with respect to the bond position of N atom. This structure can also more effectively suppress increase in the wavelength of the emission.

In the formula (2), p, q, r and s are preferably 1 or more. This structure can also more effectively suppress increase in the wavelength of the emission.

The diaminopyrene derivative represented by the formula (5), preferably by the formula (6), is also favorably usable as the dopant of the emitting layer.

Examples of $R^1$ and $R^2$ in the formula (6) are the same substituents as those of $R^1$ and $R^2$ in the formula (2).

In the formula (6), $A^1$, $A^2$, $A^3$ and $A^4$ each independently represent a substituted or unsubstituted alkyl group having 1 to 20 carbon atoms (preferably 1 to 6 carbon atoms), substituted or unsubstituted aryl group having 5 to 25 carbon atoms (preferably 5 to 10 carbon atoms), substituted or unsubstituted aralkyl group having 6 to 25 carbon atoms (preferably 6 to 10 carbon atoms), substituted or unsubstituted cycloalkyl group having 3 to 25 carbon atoms (preferably 3 to 10 carbon atoms), substituted or unsubstituted alkoxyl group having 1 to 20 carbon atoms (preferably 1 to 6 carbon atoms), substituted or unsubstituted aryloxy group having 5 to 25 carbon atoms (preferably 5 to 10 carbon atoms), substituted or unsubstituted arylamino group having 5 to 25 carbon atoms (preferably 5 to 10 carbon atoms), substituted or unsubstituted alkylamino group having 1 to 20 carbon atoms (preferably 1 to 6 carbon atoms) or substituted or unsubstituted nitrogen-containing heterocyclic group having 5 to 25 atoms for forming the ring (preferably 5 to 10 carbon atoms).

However, at least one of $Ar^1$, $Ar^2$, $Ar^3$ and $Ar^4$ is a substituted or unsubstituted nitrogen-containing heterocyclic group having 5 to 25 ring atoms (preferably 5 to 10 carbon atoms).

Examples of the nitrogen-containing heterocyclic group for $Ar^1$, $Ar^2$, $Ar^3$ and $Ar^4$ are a pyrrolyl group, imidazoyl group, pyrazolyl group, isothiazoyl group, isoxazolyl group, pyridyl group, pyrazinyl group, pyrimidinyl group, pyridazynyl group, indolizinyl group, isoindolyl group, indolyl group, indazolyl group, quinolyl group, isoquinolyl group, quinoxalyl group, pyridinyl group, pyrazinyl group, pyrimidinyl group, pyridazynyl group, triazinyl group, indolinyl group, quinolinyl group, acridinyl group, pyrrolidinyl group, piperidinyl group, piperazinyl group, oxazolyl group, oxadiazolyl group, benzoxazolyl group, thiazolyl group, thiadiazolyl group, benzothiazolyl group, triazolyl group, imidazolyl group and benzoimidazolyl group.

Examples of the diaminopyrene derivative according to the aspect of the invention are shown below.
[Chemical Formula 9]
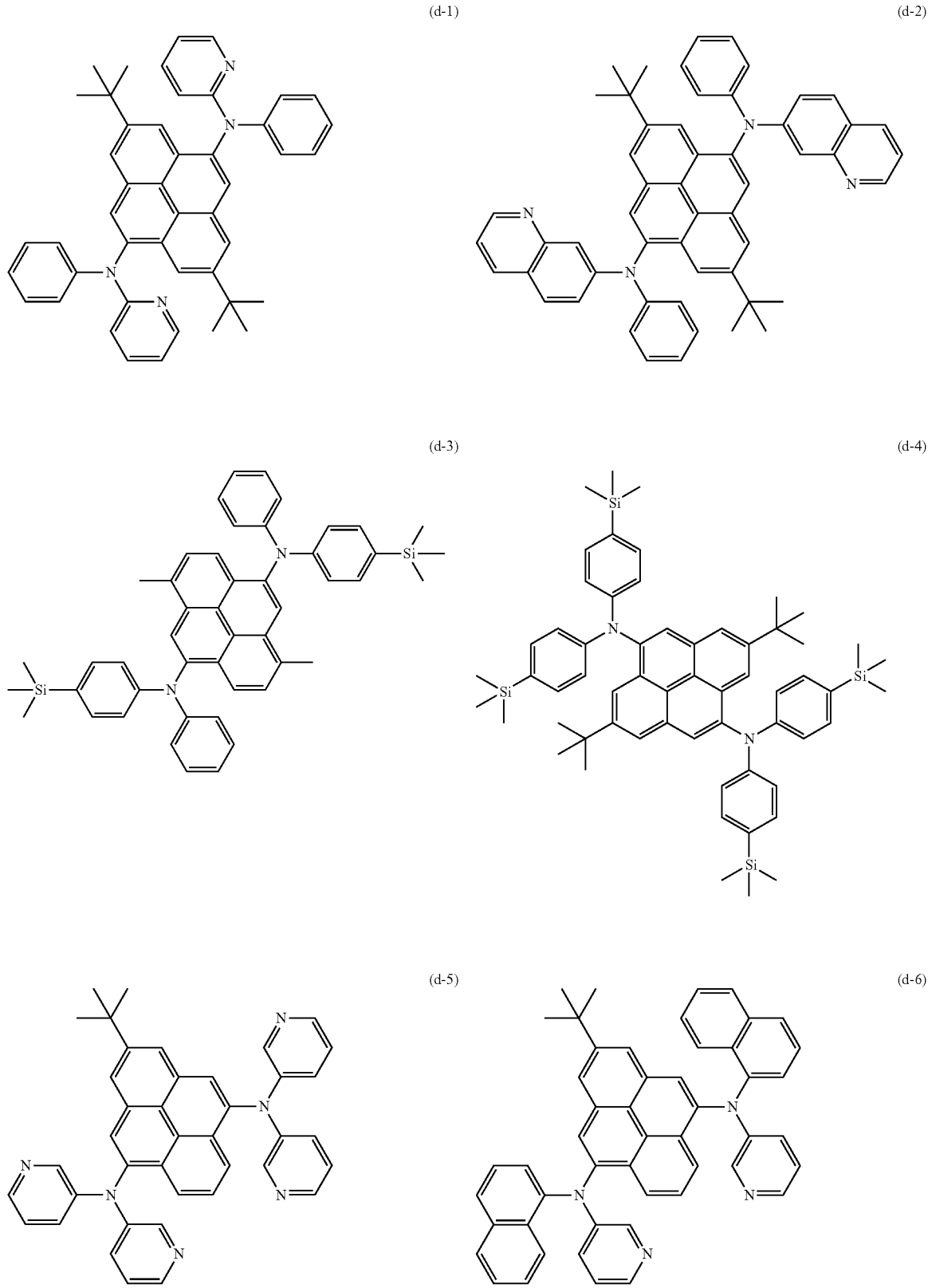

-continued
(d-7)
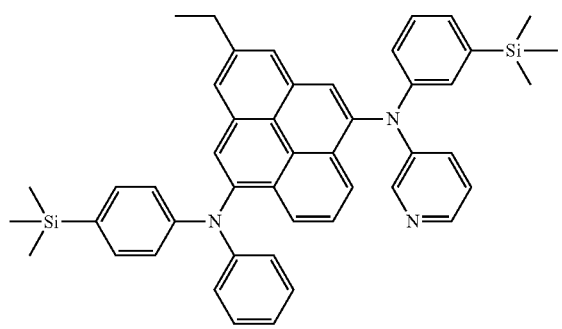
(d-8)
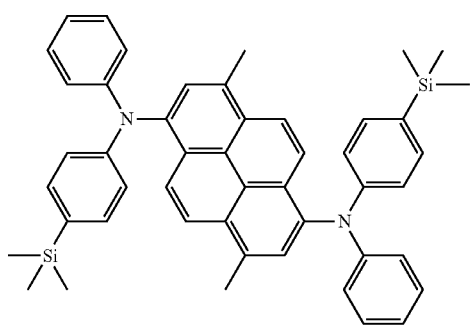
(d-9)
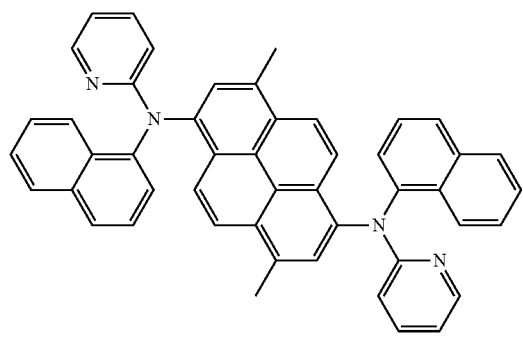
(d-10)
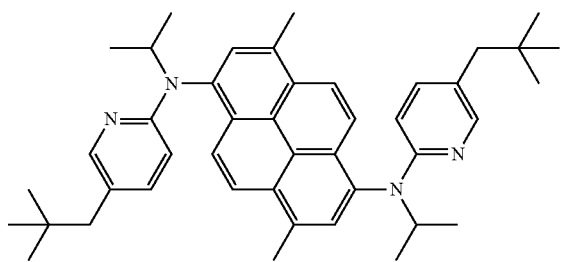
[Chemical Formula 10]
(d-11)
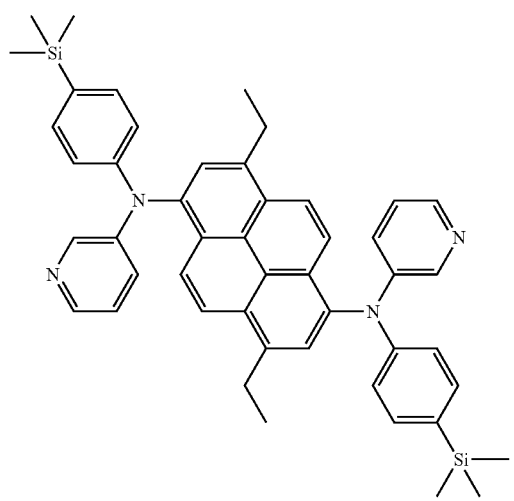
(d-12)
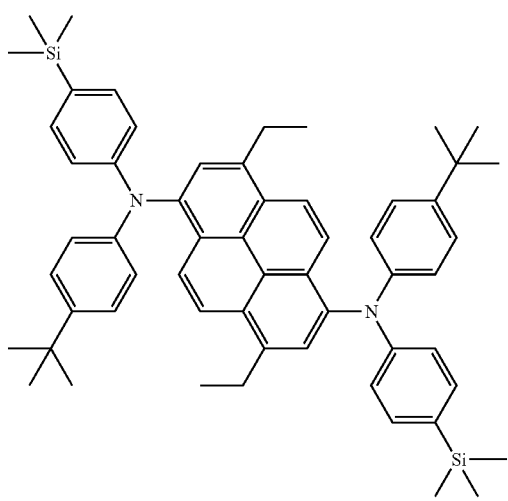

-continued
(d-13)
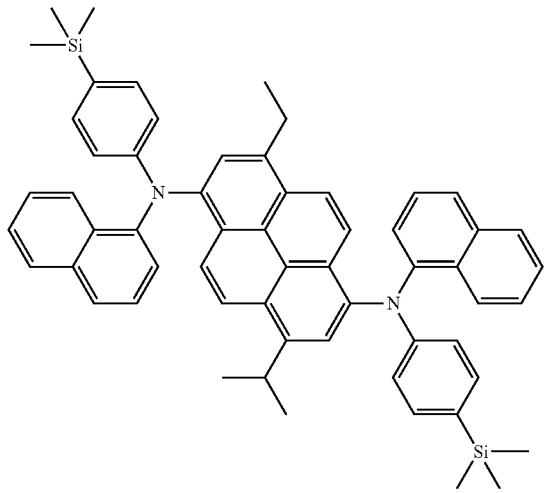
(d-14)
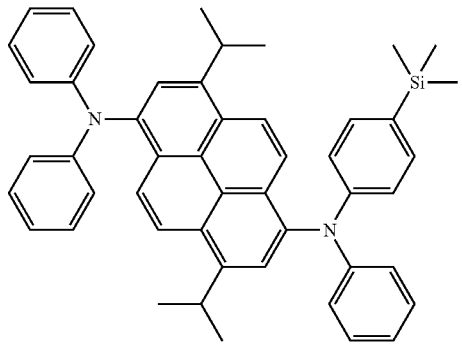
(d-15)
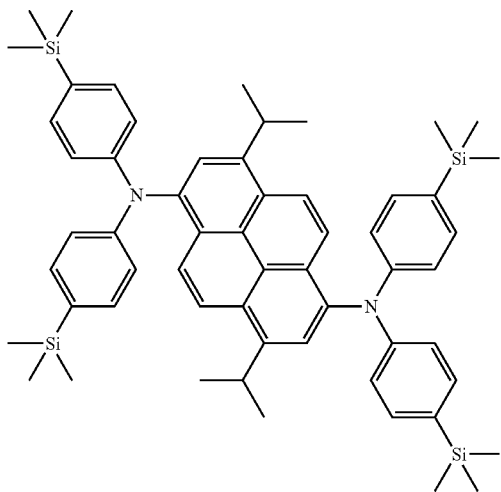
(d-16)
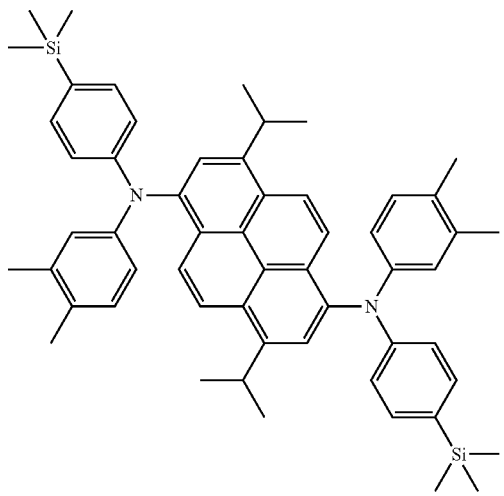
(d-17)
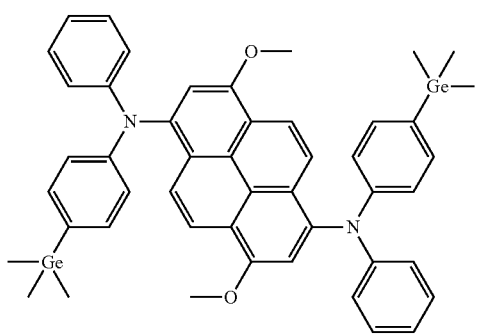
(d-18)
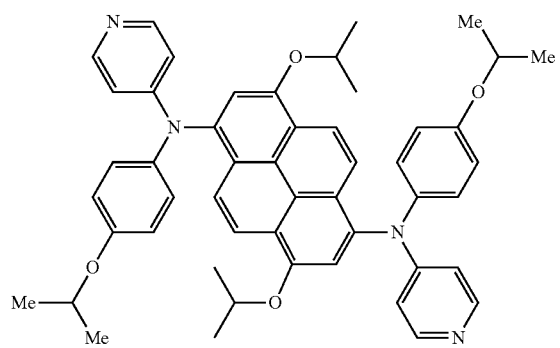

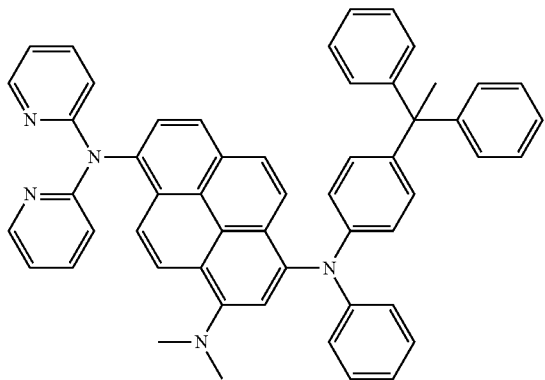
(d-19)
[Chemical Formula 11]
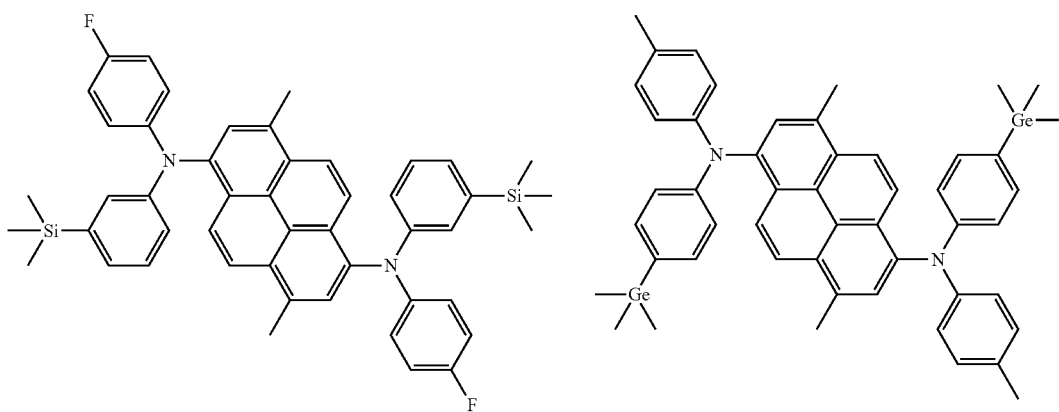
(d-20) (d-21)
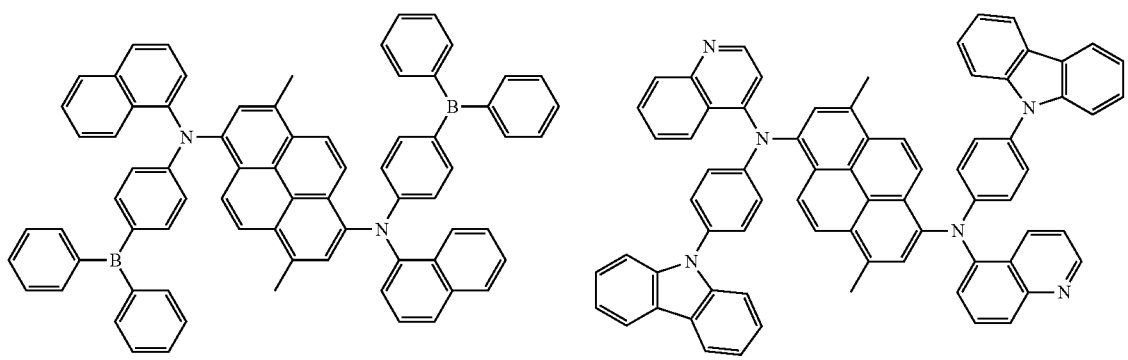
(d-22) (d-23)

-continued
(d-24)
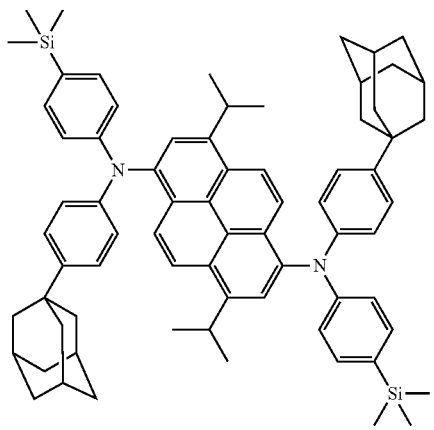
(d-25)
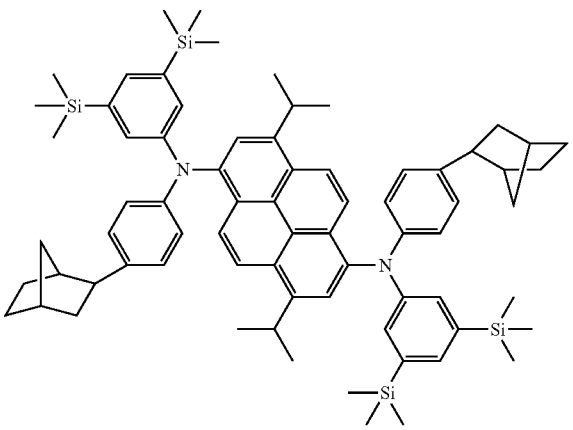
(d-26)
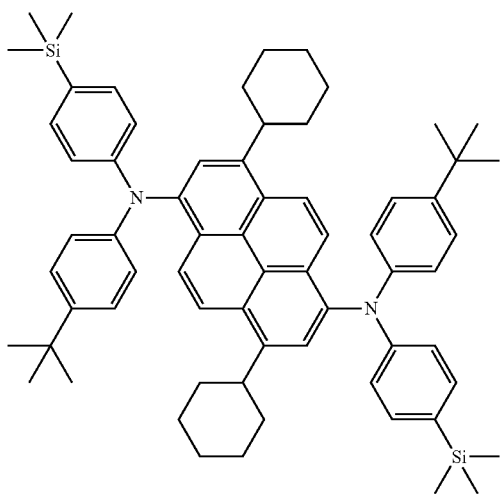
(d-27)
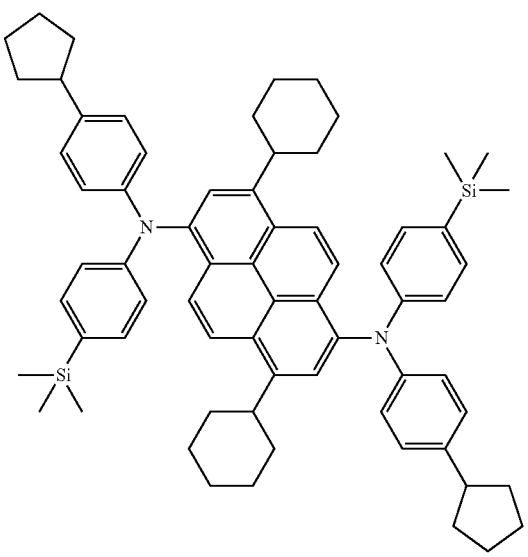
[Chemical Formula 12]
(d-28)
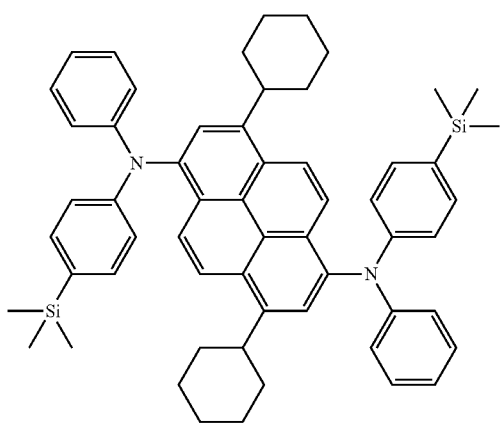
(d-29)
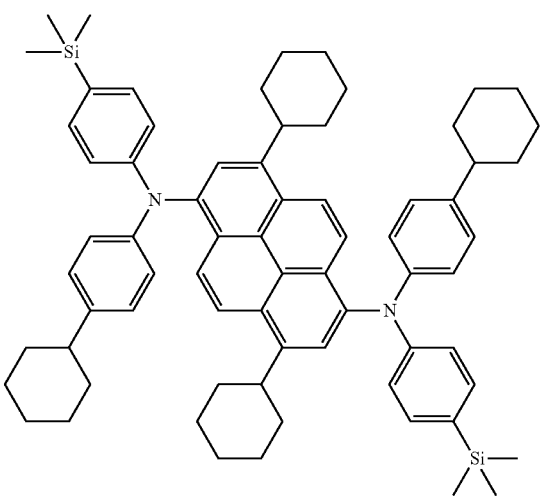

-continued
(d-30)
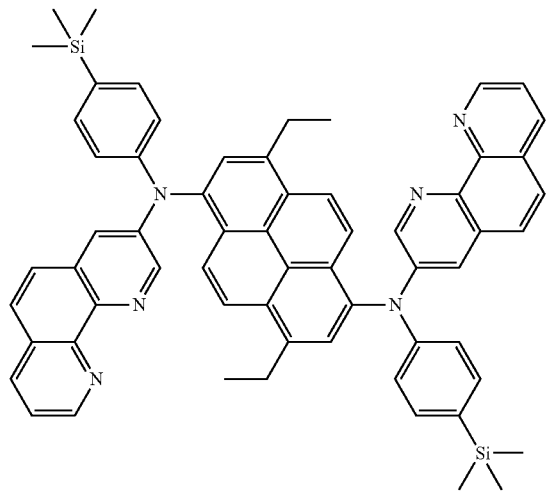
(d-31)
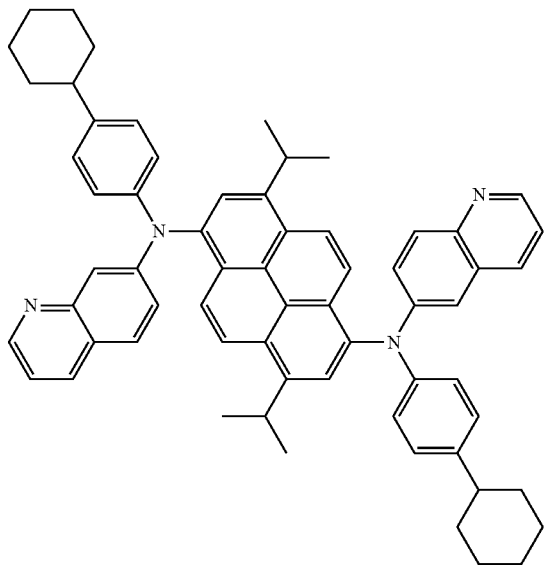
(d-32)
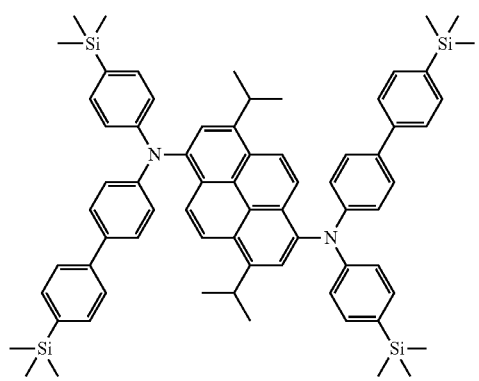
(d-33)
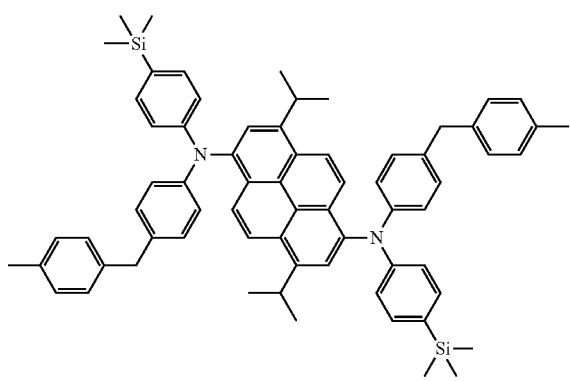
(d-34)
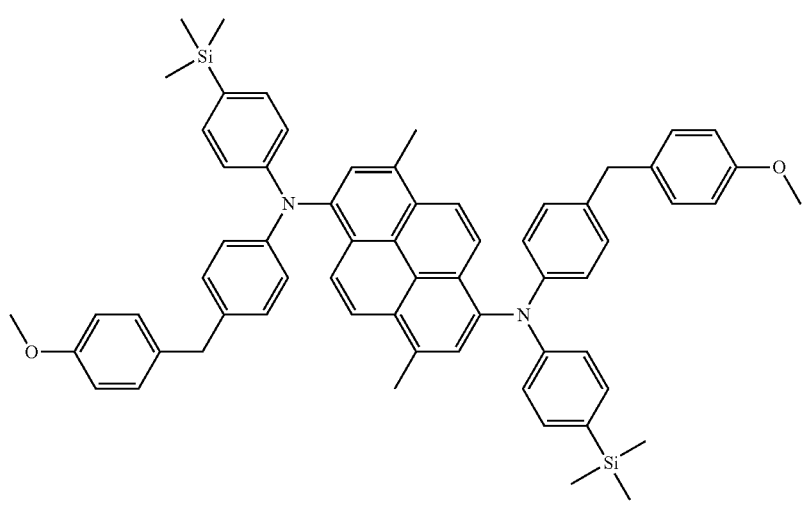

-continued
(d-35) (d-36)
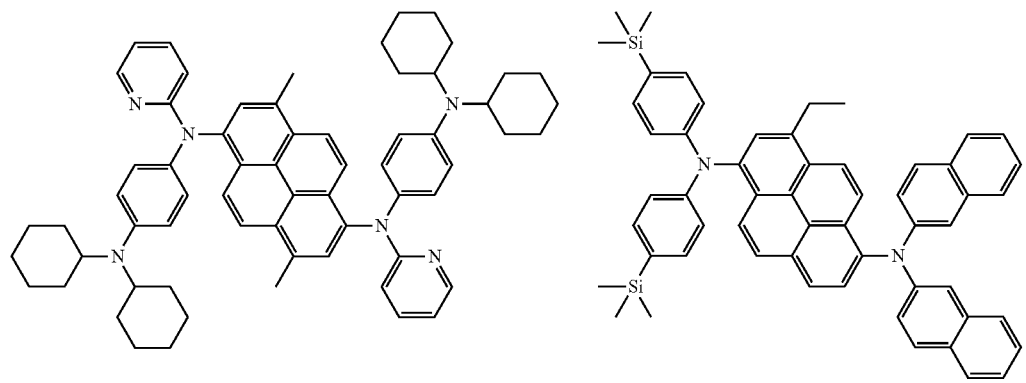
[Chemical Formula 13]
(d-37) (d-38)
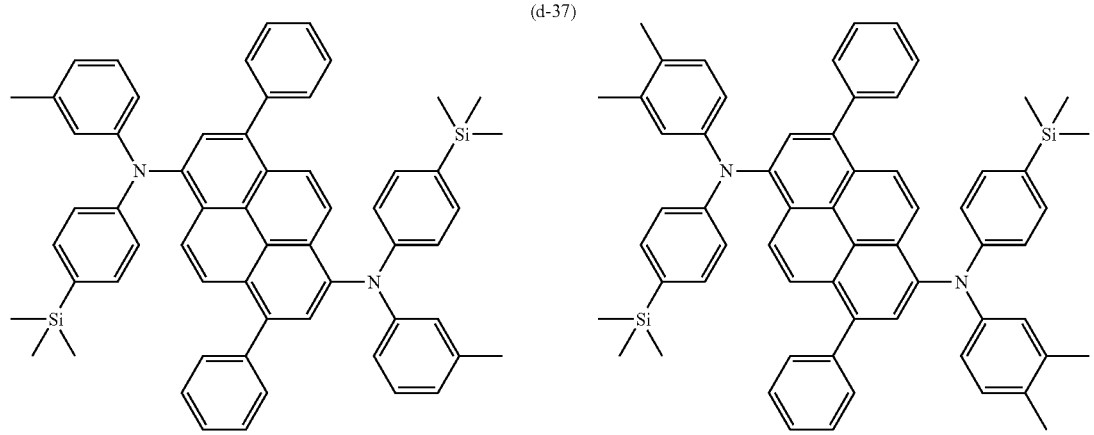
(d-39) (d-40)
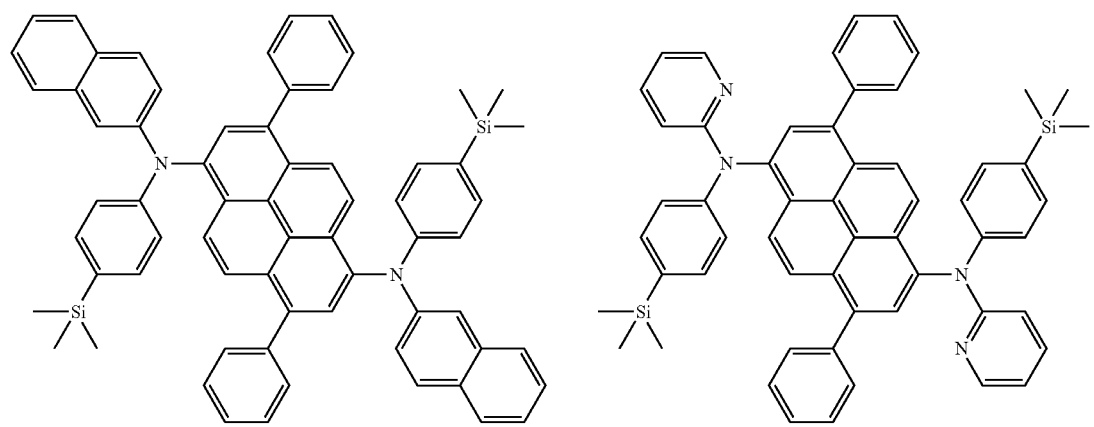

-continued
(d-41)
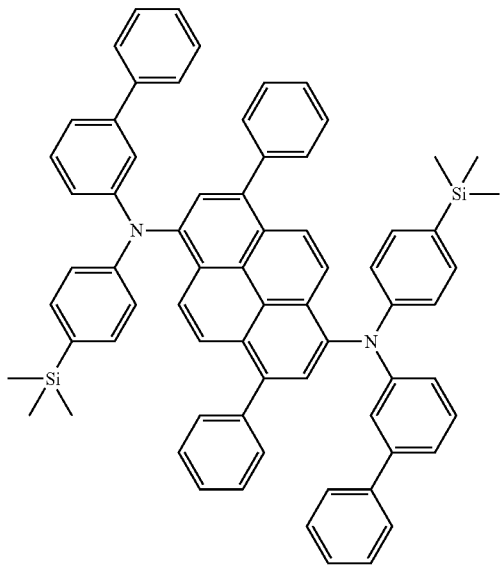
(d-42)
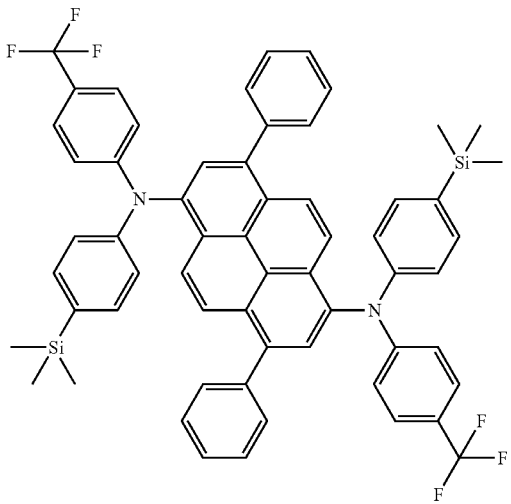
(d-43)
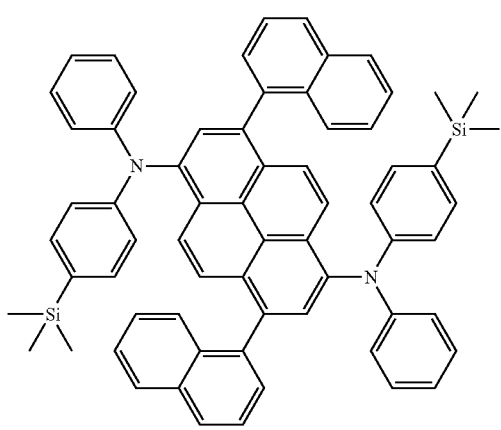
(d-44)
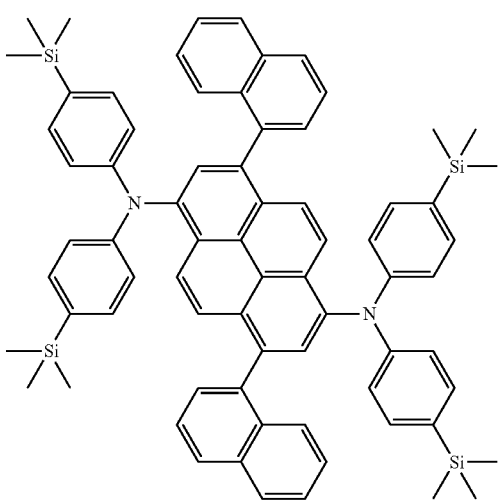
(d-45)
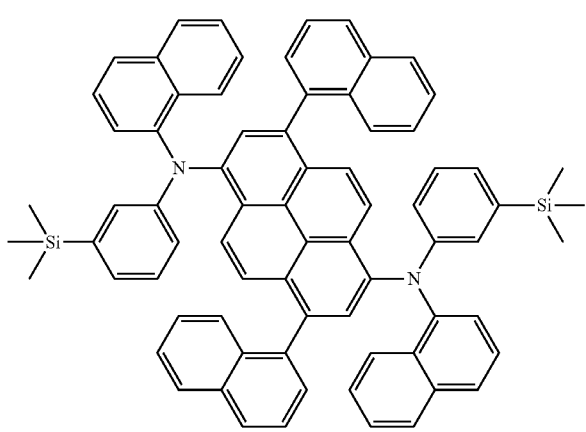

[Chemical Formula 14]
(d-46) 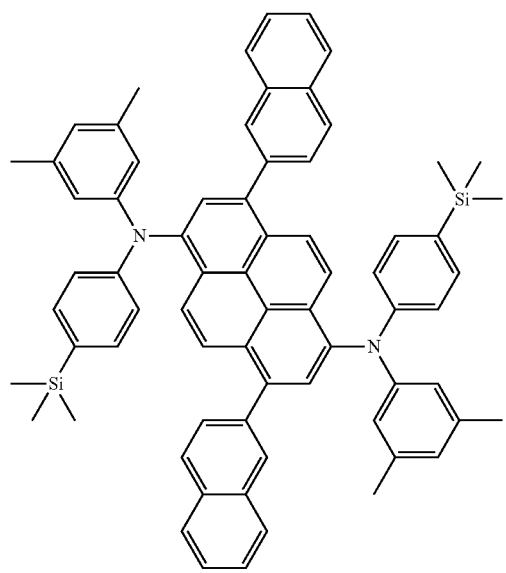
(d-47) 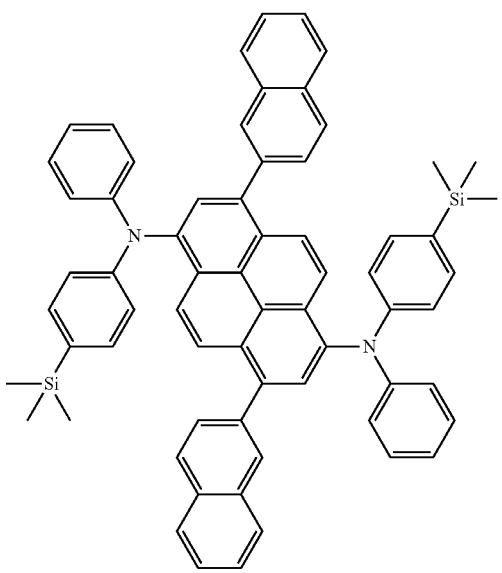
(d-48) 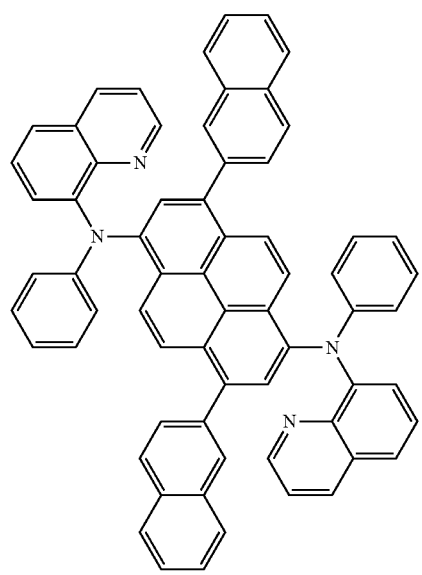
(d-49) 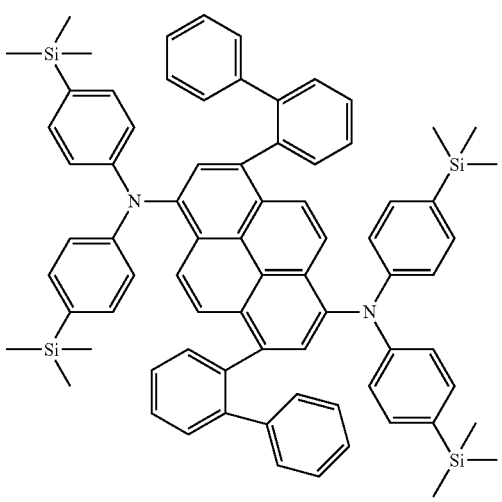
(d-50) 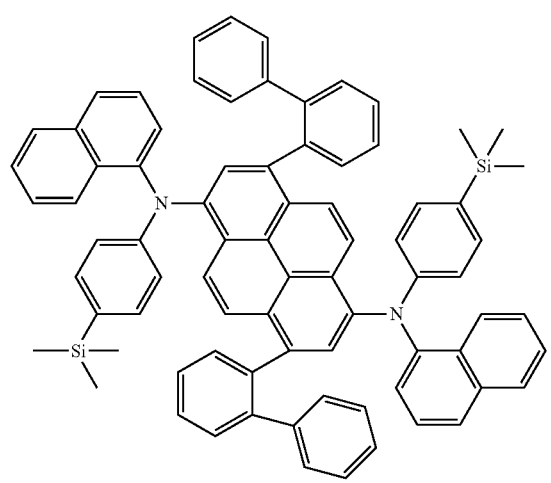
(d-51) 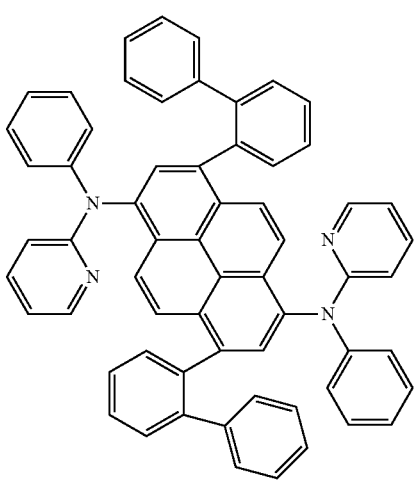

-continued
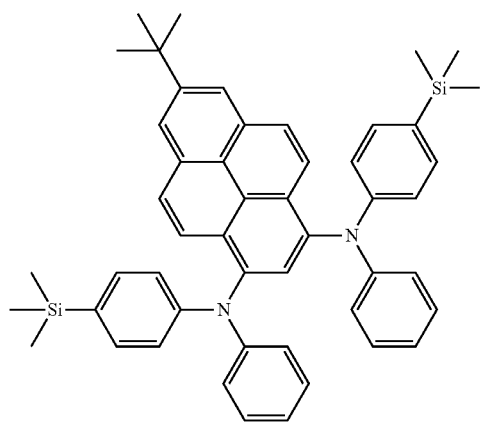
(d-52)
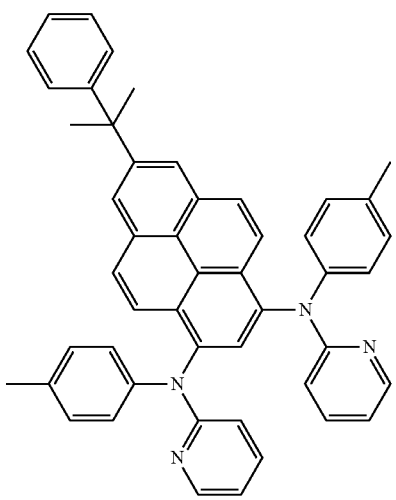
(d-53)
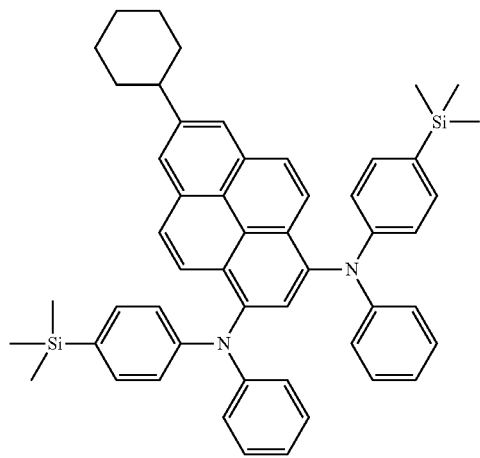
(d-54)
[Chemical Formula 15]
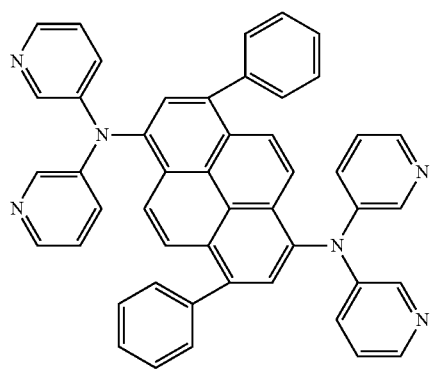
(d-55)
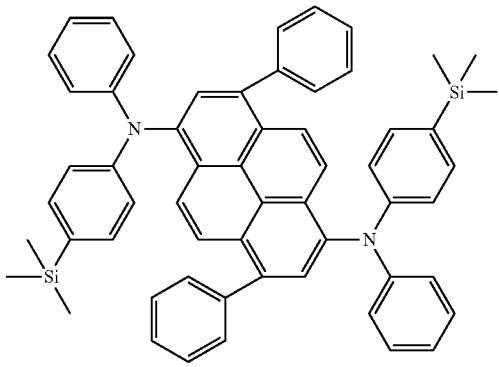
(d-56)

-continued
(d-57)
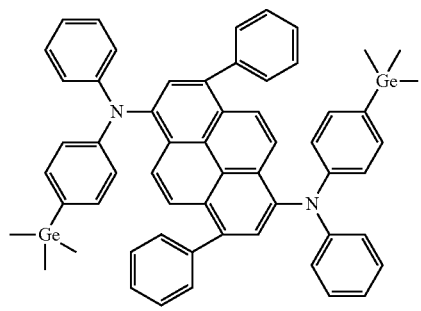
(d-58)
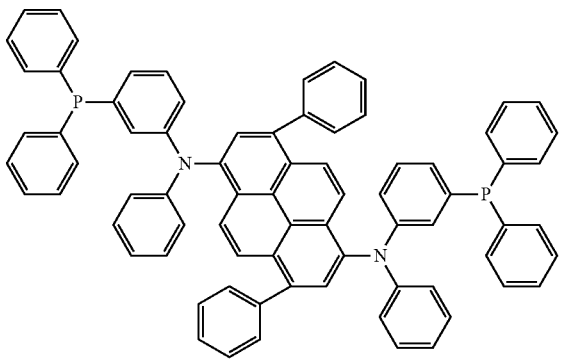
(d-59)
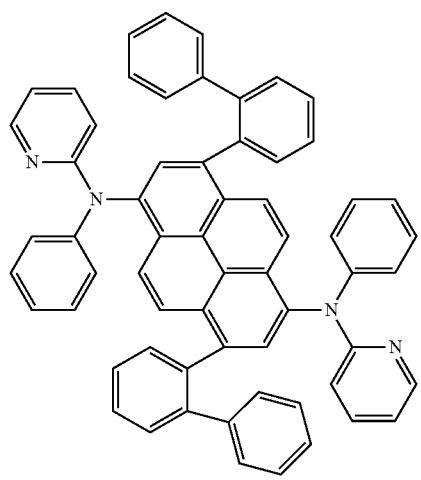
(d-60)
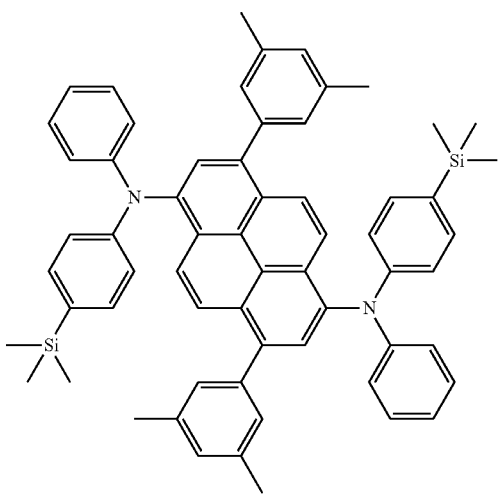
(d-61)
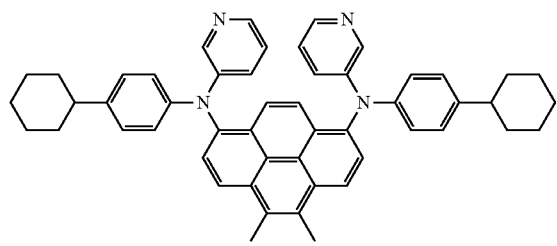
(d-62)
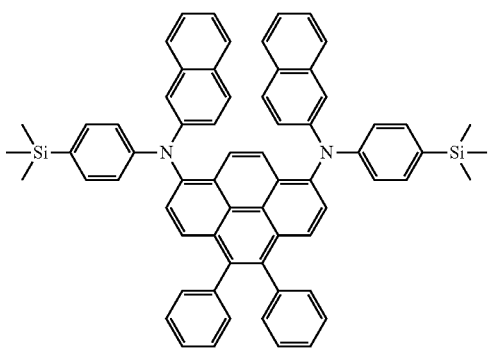

(d-63)
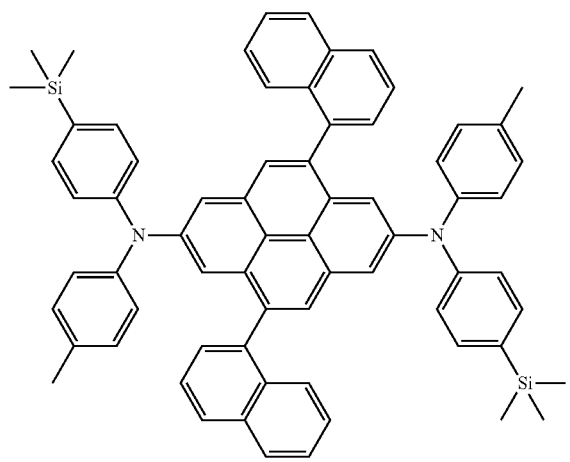
[Chemical Formula 16]
(d-64)
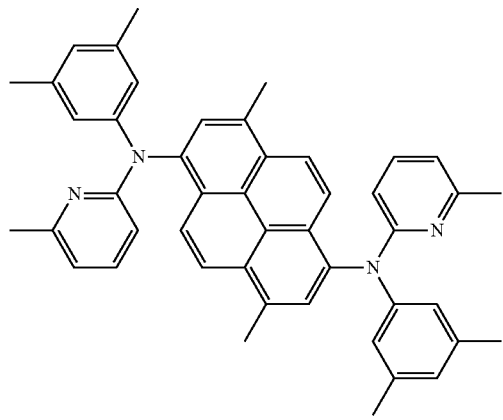
(d-65)
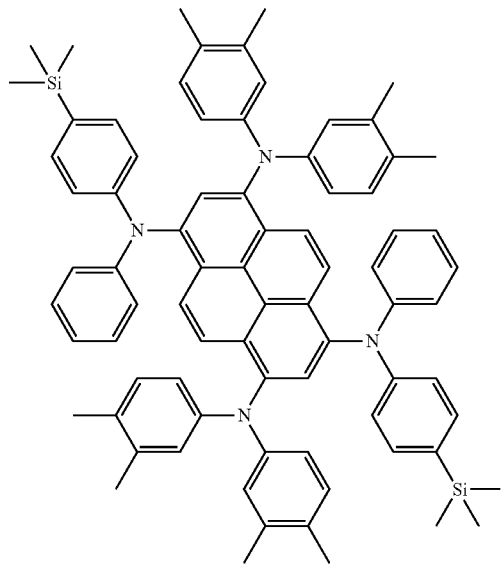
(d-66)
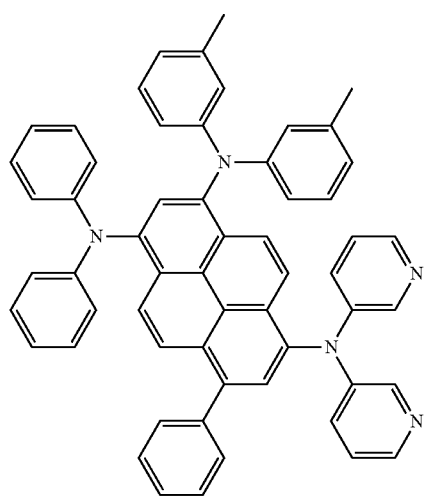
(d-67)
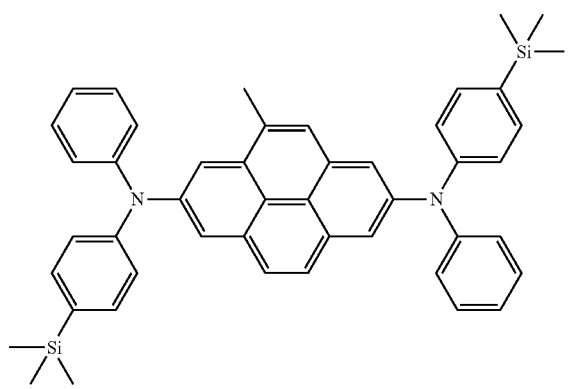

-continued
(d-68)
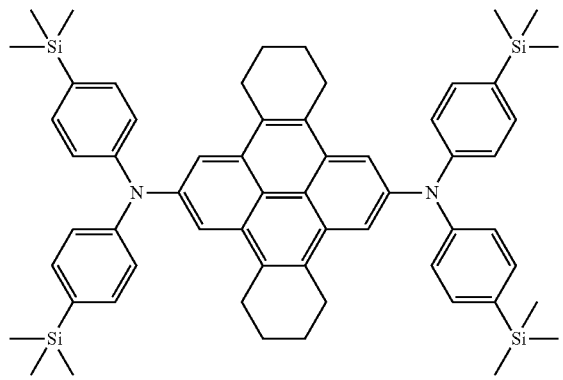
(d-69)
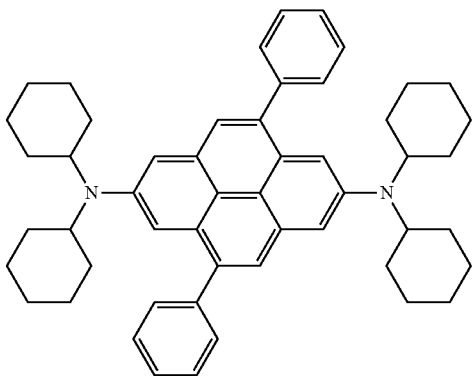
(d-70)
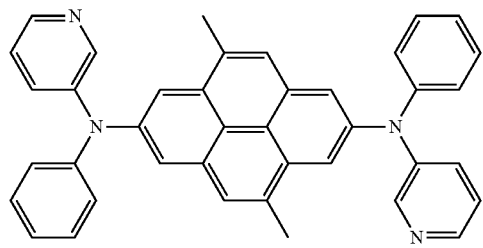
(d-71)
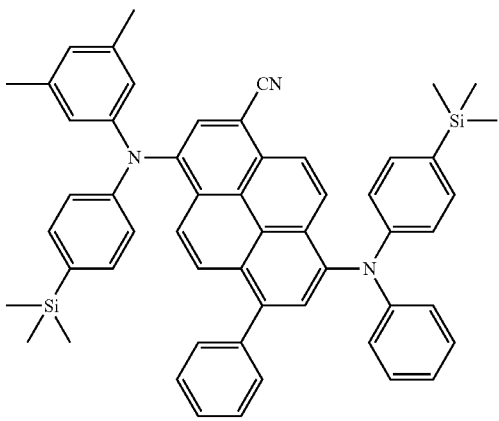
(d-72)
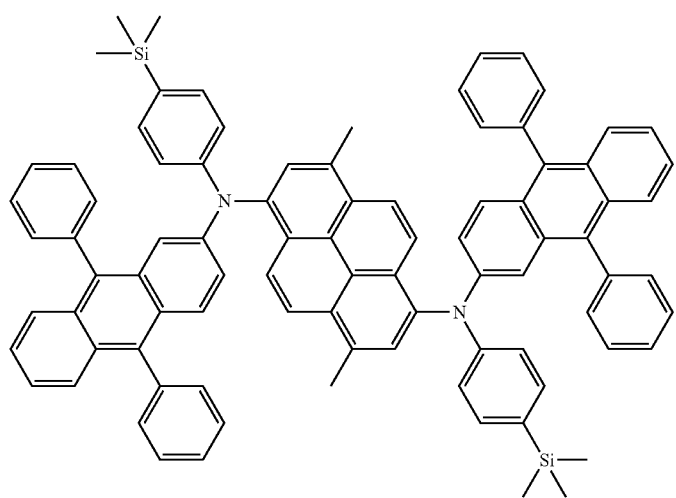

[Chemical Formula 17]
(d-73) 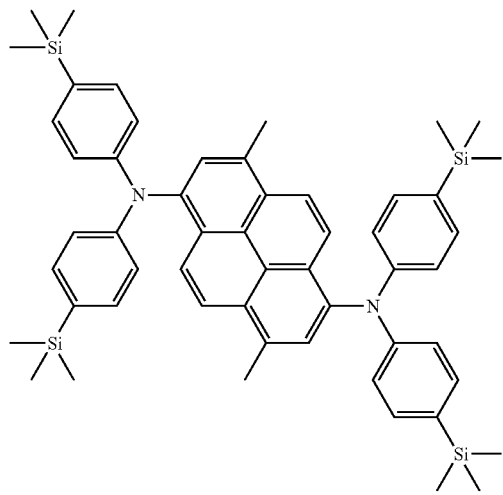
(d-74) 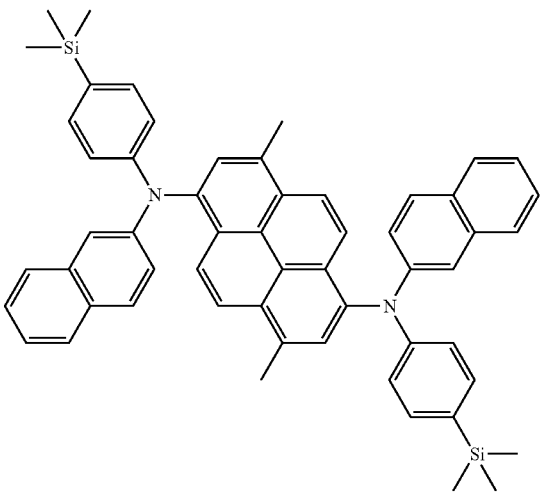
(d-75) 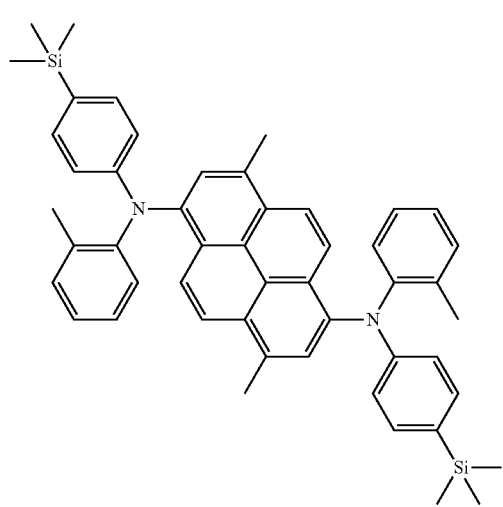
(d-76) 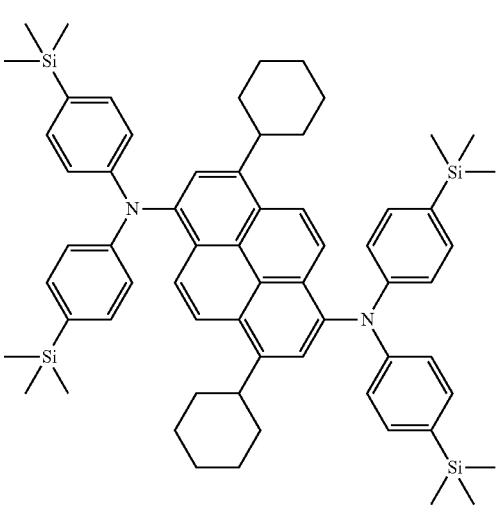
(d-77) 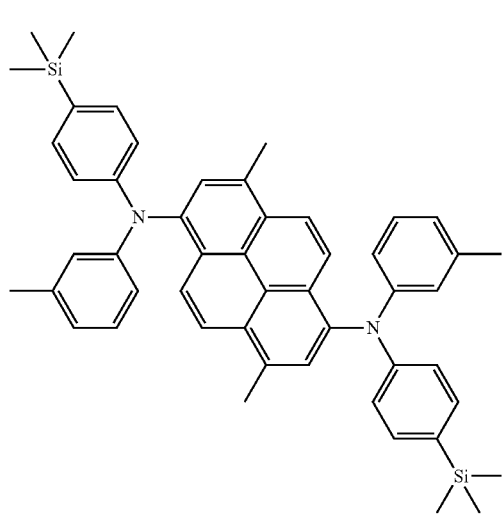
(d-78) 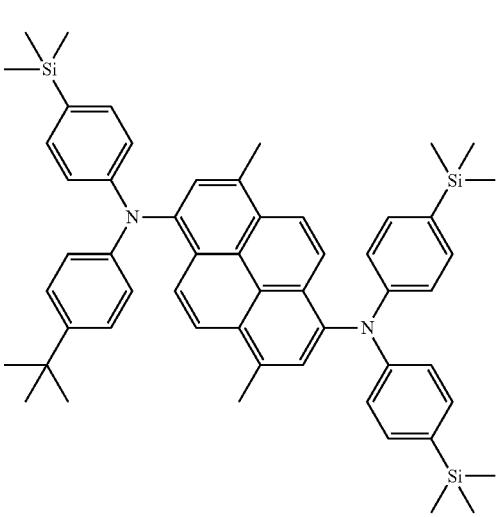

-continued
(d-79)
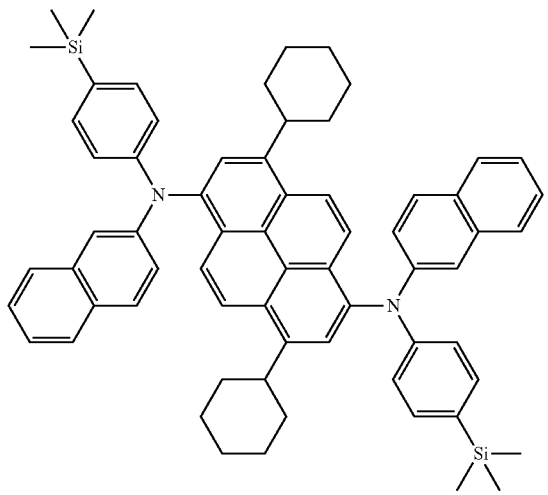
(d-80)
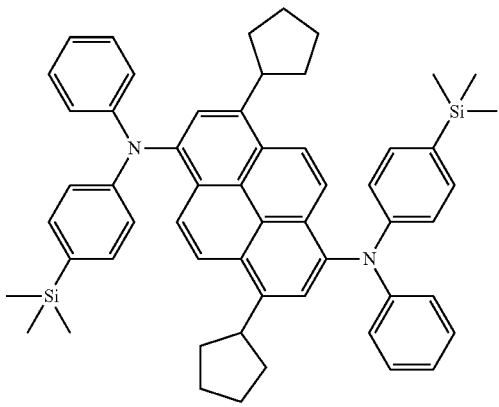
(d-81)
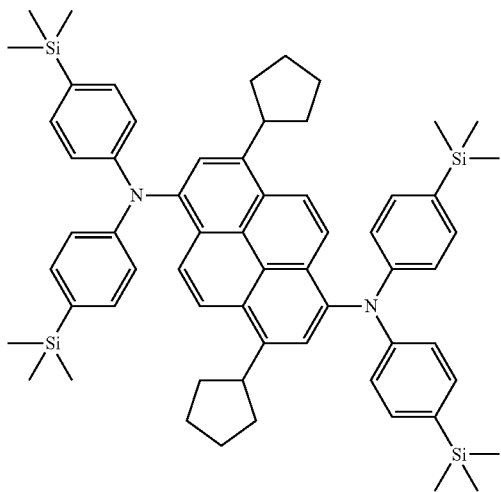
[Chemical Formula 18]
(d-82)
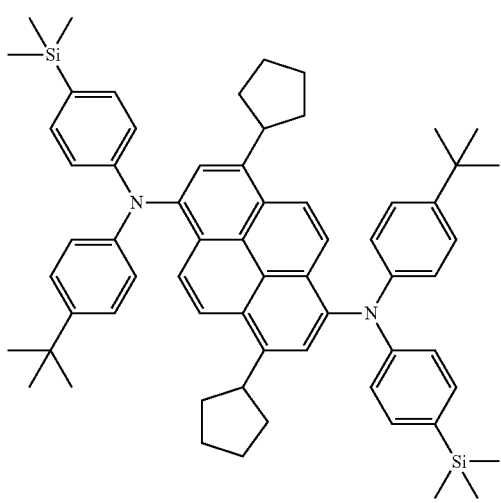
(d-83)
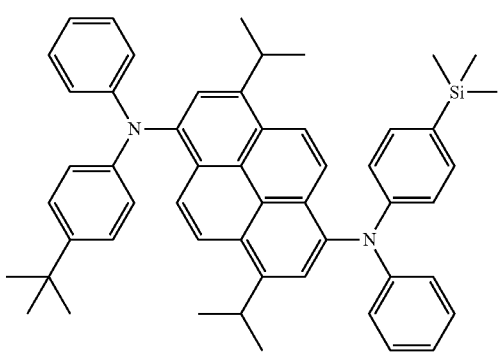

-continued
(d-84)
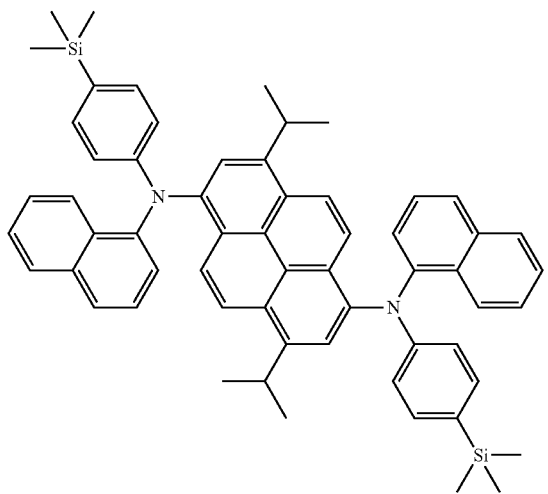
(d-85)
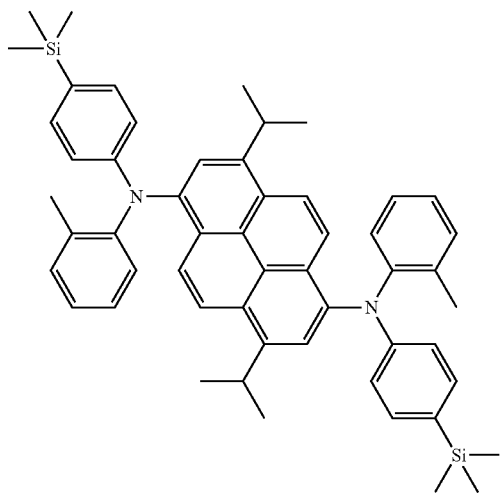
(d-86)
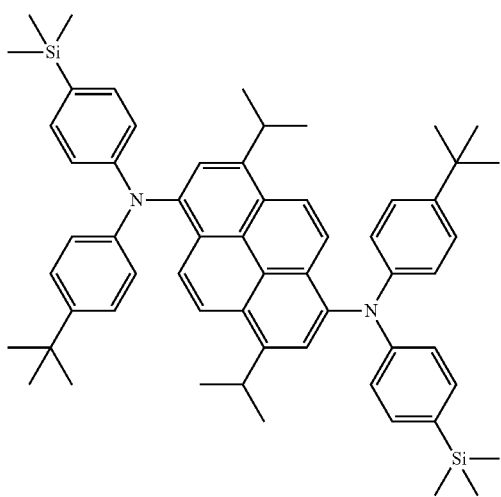
(d-87)
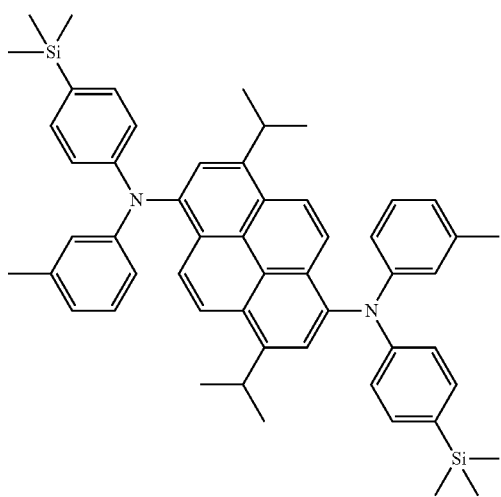
(d-88)
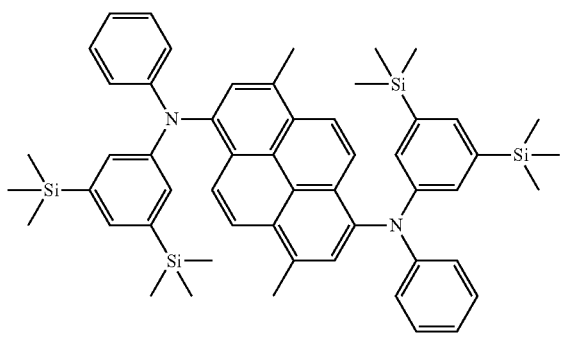
(d-89)
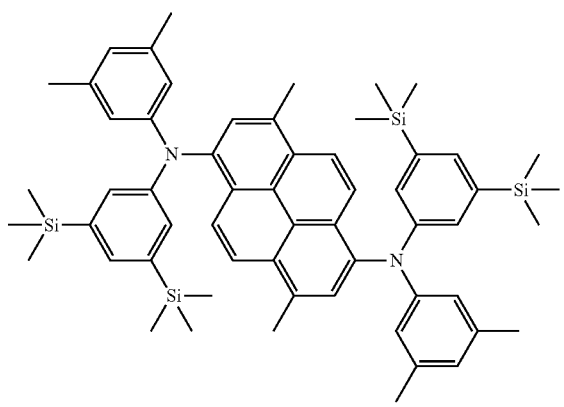

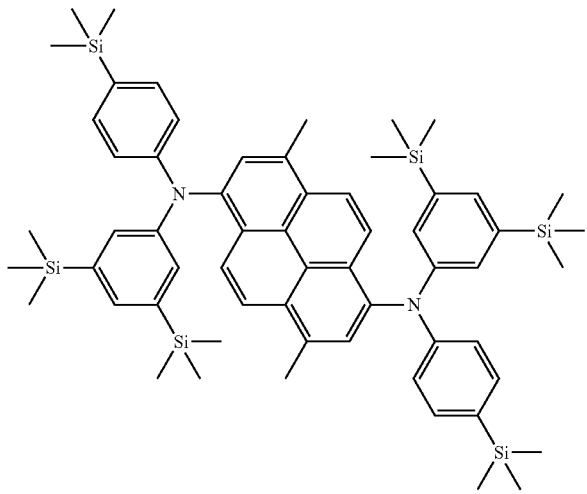
(d-90)
[Chemical Formula 19]
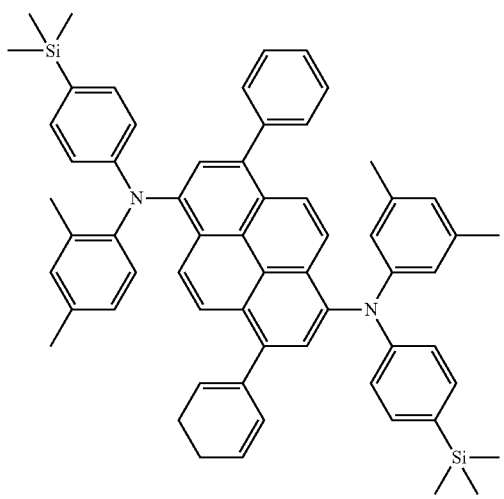
(d-91)
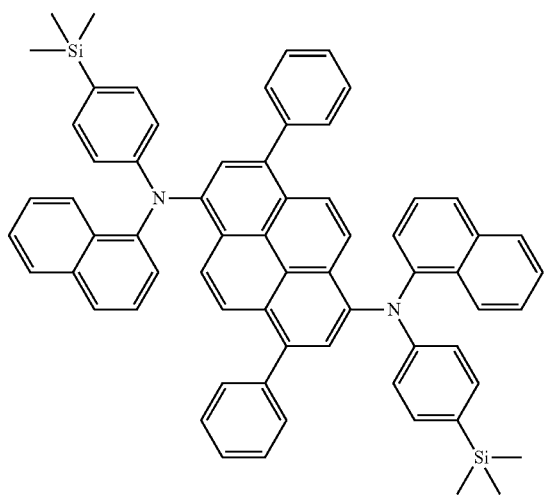
(d-92)
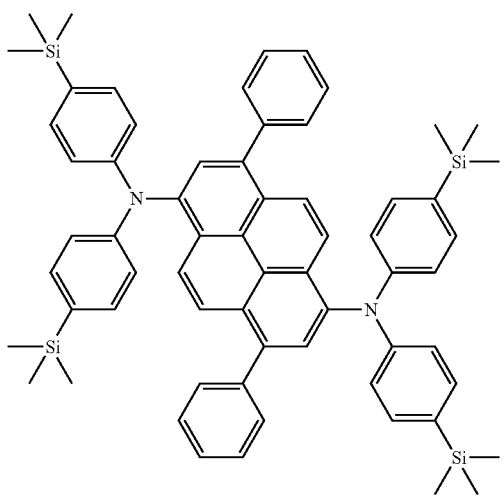
(d-93)
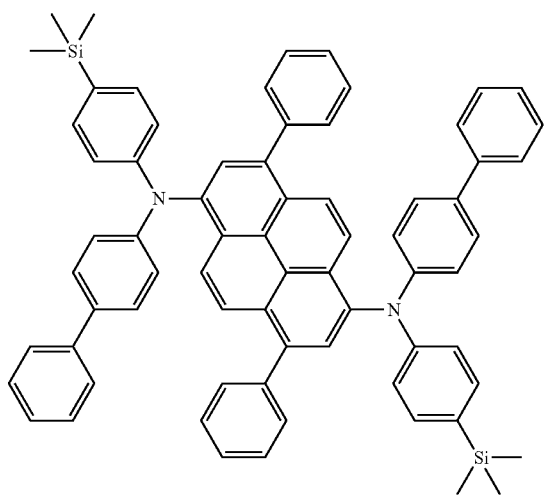
(d-94)

-continued
(d-95)
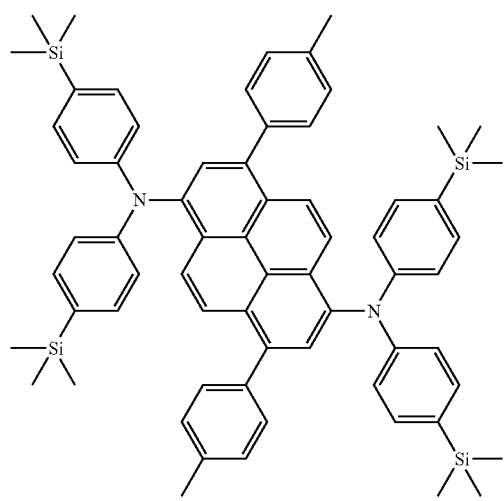
(d-96)
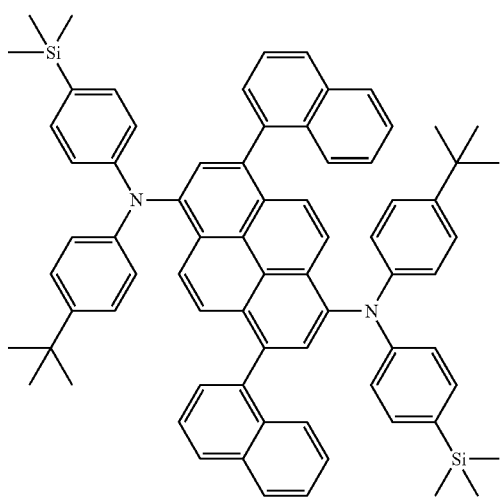
(d-97)
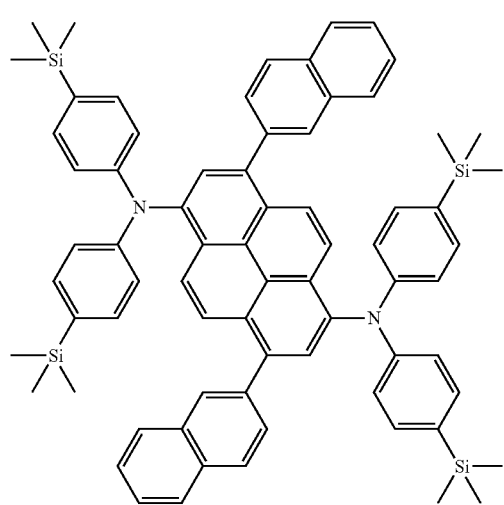
(d-98)
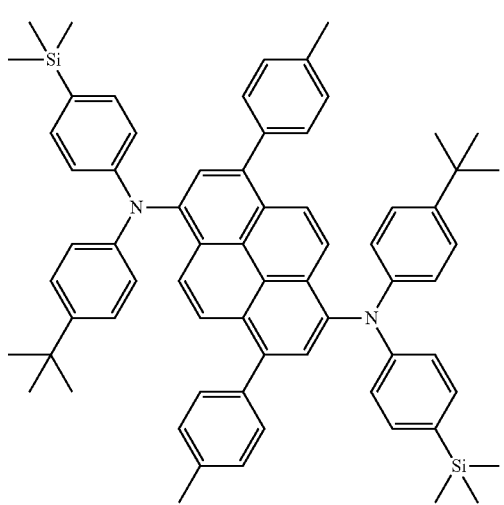
(d-99)
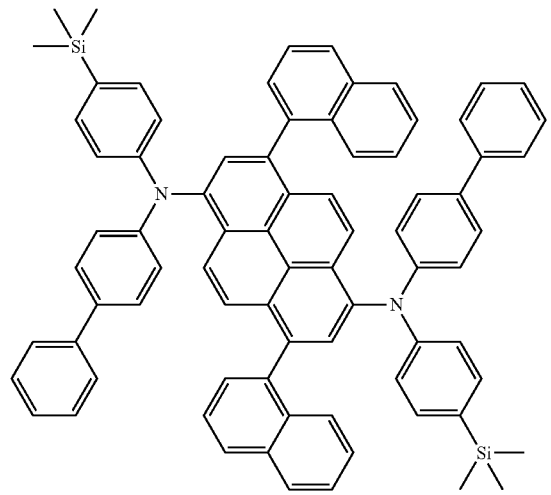
(d-100)
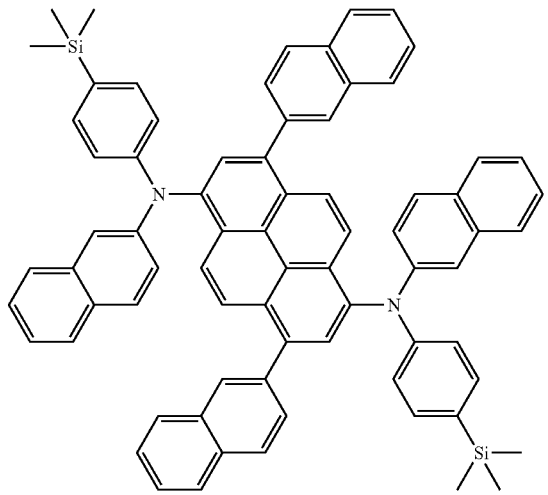

The diaminopyrene derivative according to the aspect of the invention, which has excellent capability of injecting and transporting the holes from a metal electrode or organic thin films and also of injecting and transporting the electrons from a metal electrode and organic thin films, is favorably usable as the dopant of organic EL devices.

[Host]

When used as an emitting material, the diaminopyrene derivative according to the aspect of the invention is preferably used together with a compound having a central anthracene skeleton represented by the formula (7).

In the formula (7), $B^1$ and $B^2$ each independently represent a group induced from a substituted or unsubstituted aromatic ring having 6 to 20 carbon atoms for forming the ring (preferably 6 to 10 atoms). Preferable are a substituted or unsubstituted phenyl group, substituted or unsubstituted naphthyl group (1-naphthyl group, 2-naphthyl group) and 9,9-dimethylfluorenyl group (9,9-dimethyl-1-fluorenyl group, 9,9-dimethyl-2-fluorenyl group, 9,9-dimethyl-3-fluorenyl group, 9,9-dimethyl-4-fluorenyl group).

The aromatic ring may be substituted by 1 or more substituent(s).

The substituent is selected from a substituted or unsubstituted aryl group having 6 to 50 carbon atoms for forming the ring (preferably 6 to 10 carbon atoms), substituted or unsubstituted alkyl group having 1 to 50 carbon atoms (preferably 1 to 6 carbon atoms), substituted or unsubstituted cycloalkyl group having 3 to 50 carbon atoms (preferably 3 to 10 carbon atoms), substituted or unsubstituted alkoxy group having 1 to 50 carbon atoms (preferably 6 to 10 carbon atoms), substituted or unsubstituted aralkyl group having 6 to 50 carbon atoms (preferably 6 to 10 carbon atoms), substituted or unsubstituted aryloxy group having 5 to 50 atoms for forming the ring (preferably 5 to 10 atoms), substituted or unsubstituted arylthio group having 5 to 50 atoms for forming the ring (preferably 5 to 10 carbon atoms), substituted or unsubstituted alkoxycarbonyl group having 1 to 50 carbon atoms (preferably 1 to 6 carbon atoms), substituted or unsubstituted silyl group, carboxyl group, halogen atom, cyano group, nitro group and hydroxyl group. A substituted or unsubstituted aryl group having 6 to 50 ring carbon atoms (preferably 6 to 10 carbon atoms) is preferable. More preferable are a substituted or unsubstituted phenyl group, substituted or unsubstituted naphthyl group (1-naphthyl group, 2-naphthyl group) and 9,9-dimethylfluorenyl group (9,9-dimethyl-1-fluorenyl group, 9,9-dimethyl-2-fluorenyl group, 9,9-dimethyl-3-fluorenyl group, 9,9-dimethyl-4-fluorenyl group).

When the aromatic ring is substituted by 2 or more substituents, the substituents may be the same or different. Alternatively, the substituents may be bonded together to form a saturated or unsaturated ring structure.

$B^1$ and $B^2$ are preferably different from each other.

Examples of the group induced from the substituted or unsubstituted aromatic ring having 6 to 20 ring carbon atoms for $B^1$ and $B^2$ in the formula (7) are a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 4-(1-naphthyl)phenyl group, 3-(1-naphthyl)phenyl group, 2-(1-naphthyl)phenyl group, 4-(2-naphthyl)phenyl group, 3-(2-naphthyl)phenyl group, 2-(2-naphthyl)phenyl group, 4-(1-naphthyl)-1-naphthyl group, 4-(2-naphthyl)-1-naphthyl group, 3-(1-naphthyl)-1-naphthyl group, 3-(2-naphthyl)-1-naphthyl group, 2-(1-naphthyl)-1-naphthyl group, 2-(2-naphthyl)-1-naphthyl group, 5-(1-naphthyl)-1-naphthyl group, 5-(2-naphthyl)-1-naphthyl group, 6-(1-naphthyl)-1-naphthyl group, 6-(2-naphthyl)-1-naphthyl group, 7-(1-naphthyl)-1-naphthyl group, 7-(2-naphthyl)-1-naphthyl group, 8-(1-naphthyl)-1-naphthyl group, 8-(2-naphthyl)-1-naphthyl group, 4-(1-naphthyl)-2-naphthyl group, 4-(2-naphthyl)-2-naphthyl group, 3-(1-naphthyl)-2-naphthyl group, 3-(2-naphthyl)-2-naphthyl group, 1-(1-naphthyl)-2-naphthyl group, 1-(2-naphthyl)-2-naphthyl group, 5-(1-naphthyl)-2-naphthyl group, 5-(2-naphthyl)-2-naphthyl group, 6-(1-naphthyl)-2-naphthyl group, 6-(2-naphthyl)-2-naphthyl group, 7-(1-naphthyl)-2-naphthyl group, 7-(2-naphthyl)-2-naphthyl group, 8-(1-naphthyl)-2-naphthyl group and 8-(2-naphthyl)-2-naphthyl group. In particular, a phenyl group, 1-naphthyl group, 2-naphthyl group and 9-phenanthryl group are preferable.

Examples of the substituted or unsubstituted aryl group having 6 to 50 ring carbon atoms as the substituent for the aromatic ring are a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group and 4"-t-butyl-p-terphenyl-4-yl group. The aryl group is preferably a substituted or unsubstituted aryl group having 6 to 18 ring carbon atoms. Particularly preferable are a phenyl group, 1-naphthyl group, 2-naphthyl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, o-tolyl group, m-tolyl group, p-tolyl group and p-t-butylphenyl group.

Additionally preferable are a phenyl group substituted by a phenyl group, naphthyl group substituted by a phenyl group (e.g., 1-naphthyl group substituted by a phenyl group, 2-naphthyl group substituted by a phenyl group), phenyl group substituted by naphthyl group (e.g., phenyl group substituted by a 1-naphthyl group, phenyl group substituted by a 2-naphthyl group) and naphthyl group substituted by a naphthyl group such as 1-naphthyl group and 2-naphthyl group.

$R^{71}$ to $R^{78}$ in the formula (7) are each independently selected from a hydrogen atom, substituted or unsubstituted aryl group having 6 to 50 carbon atoms for forming the ring (preferably 5 to 10 carbon atoms), substituted or unsubstituted heteroaryl group having 5 to 50 atoms for forming the ring (preferably 5 to 10 carbon atoms), substituted or unsubstituted alkyl group having 1 to 50 carbon atoms (preferably 1 to 6 carbon atoms), substituted or unsubstituted cycloalkyl group having 3 to 50 carbon atoms (preferably 3 to 10 carbon atoms), substituted or unsubstituted alkoxy group having 1 to 50 carbon atoms (preferably 1 to 6 carbon atoms), substituted or unsubstituted aralkyl group having 6 to 50 carbon atoms (preferably 5 to 10 carbon atoms), substituted or unsubstituted aryloxy group having 5 to 50 atoms for forming the ring (preferably 5 to 10 atoms), substituted or unsubstituted arylthio group having 5 to 50 atoms for forming the ring (preferably 5 to 10 carbon atoms), substituted or unsubstituted alkoxycarbonyl group having 1 to 50 carbon atoms, substituted or unsubstituted silyl group, carboxyl group, halogen atom, cyano group, nitro group and hydroxyl group.

Examples of the substituted or unsubstituted aryl group having 6 to 50 ring carbon atoms for $R^{71}$ to $R^{78}$ in the formula (7) are a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group and 4''-t-butyl-p-terphenyl-4-yl group.

Examples of the substituted or unsubstituted heteroaryl group having 5 to 50 ring carbon atoms for $R^{71}$ to $R^{78}$ in the formula (7) are a 1-pyroryl group, 2-pyroryl group, 3-pyroryl group, pyrazinyl group, 2-pyridiny group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

Examples of the substituted or unsubstituted alkyl group having 1 to 50 carbon atoms for $R^{71}$ to $R^{78}$ in the formula (7) and the substituent for the aromatic ring are a methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

Examples of the substituted or unsubstituted cycloalkyl group having 3 to 50 carbon atoms for $R^{71}$ to $R^{78}$ in the formula (7) and the substituent for the aromatic ring are a cyclopropyl group, cyclobutyl group, cyclopentyl group, cyclohexyl group, 4-methylcyclohexyl group, 1-adamantyl group, 2-adamantyl group, 1-norbornyl group and 2-norbornyl group.

The substituted or unsubstituted alkoxy group having 1 to 50 carbon atoms for $R^{71}$ to $R^{78}$ in the formula (7) and the substituent for the aromatic ring is a group represented by —OY. Examples of Y are the same as those of the substituted or unsubstituted alkyl group having 1 to 50 carbon atoms for $R^{71}$ to $R^{78}$ and the substituent for the aromatic ring.

Examples of the substituted or unsubstituted aralkyl group having 6 to 50 carbon atoms for $R^{71}$ to $R^{78}$ in the formula (7)

and the substituent for the aromatic ring are a benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrorylmethyl group, 2-(1-pyroryl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group.

The substituted or unsubstituted aryloxy group and arylthio group each having 5 to 50 ring atoms for $R^{71}$ to $R^{78}$ in the formula (7) and the substituent for the aromatic ring are groups respectively represented by —OY' and —SY". Examples of Y' and Y" are the same as those of the substituted or unsubstituted aryl group having 6 to 50 ring atoms for $R^{71}$ to $R^{78}$ and the substituent for the aromatic ring.

The substituted or unsubstituted alkoxycarbonyl group having 1 to 50 carbon atoms for $R^{71}$ to $R^{78}$ in the formula (7) and the substituent for the aromatic ring is a group represented by —COOZ. Examples of Z are the same as those of the substituted or unsubstituted alkyl group having 1 to 50 carbon atoms for $R^{71}$ to $R^{78}$ and the substituent for the aromatic ring.

Examples of the halogen atom for $R^{71}$ to $R^{78}$ in the formula (7) and the substituent for the aromatic ring are fluorine, chlorine, bromine and iodine.

Examples of the substituent for $R^{71}$ to $R^{78}$ and the substituent for the aromatic ring are a halogen atom, hydroxyl group, nitro group, cyano group, alkyl group, aryl group, cycloalkyl group, alkoxy group, aromatic heterocyclic group, aralkyl group, aryloxy group, arylthio group, alkoxycarbonyl group and carboxyl group.

Preferably, the anthracene derivative represented by the formula (7) is a compound having a structure represented by the following formula (7').

[Chemical Formula 20]

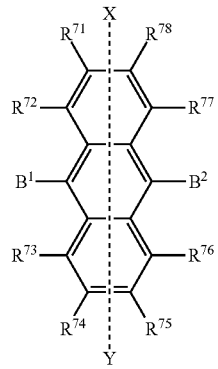

(7')

In the formula (7'), $B^1$ and $B^2$ each independently represent a group induced from a substituted or unsubstituted aromatic ring having 6 to 20 ring carbon atoms. The aromatic ring may be substituted by 1 or more substituent(s). The substituent is selected from a substituted or unsubstituted aryl group having 6 to 50 ring carbon atoms (preferably 6 to 10 carbon atoms), substituted or unsubstituted alkyl group having 1 to 50 carbon atoms (preferably 1 to 6 carbon atoms), substituted or unsubstituted cycloalkyl group having 3 to 50 carbon atoms (preferably 3 to 10 carbon atoms), substituted or unsubstituted alkoxy group having 1 to 50 carbon atoms (preferably 1 to 6 carbon atoms), substituted or unsubstituted aralkyl group having 6 to 50 carbon atoms (preferably 6 to 10 carbon atoms), substituted or unsubstituted aryloxy group having 5 to 50 ring atoms (preferably 5 to 10 atoms), substituted or unsubstituted arylthio group having 5 to 50 ring atoms (preferably 5 to 10 carbon atoms), substituted or unsubstituted alkoxycarbonyl group having 1 to 50 carbon atoms (preferably 1 to 6 carbon atoms), substituted or unsubstituted silyl group, carboxyl group, halogen atom, cyano group, nitro group and hydroxyl group. When the aromatic ring is substituted by 2 or more substituents, the substituents may be the same or different. Alternatively, the substituents may be bonded together to form a saturated or unsaturated ring structure.

$R^{71}$ to $R^{78}$ are each independently selected from a hydrogen atom, substituted or unsubstituted aryl group having 6 to 50 ring carbon atoms (preferably 6 to 10 carbon atoms), substituted or unsubstituted heteroaryl group having 5 to 50 ring atoms (preferably 5 to 10 carbon atoms), substituted or unsubstituted alkyl group having 1 to 50 carbon atoms (preferably 1 to 6 carbon atoms), substituted or unsubstituted cycloalkyl group having 3 to 50 carbon atoms (preferably 3 to 10 carbon atoms), substituted or unsubstituted alkoxy group having 1 to 50 carbon atoms (preferably 1 to 6 carbon atoms), substituted or unsubstituted aralkyl group having 6 to 50 carbon atoms (preferably 6 to 10 carbon atoms), substituted or unsubstituted aryloxy group having 5 to 50 ring atoms (preferably 5 to 10 carbon atoms), substituted or unsubstituted arylthio group having 5 to 50 ring atoms (preferably 5 to 10 carbon atoms), substituted or unsubstituted alkoxycarbonyl group having 1 to 50 carbon atoms (preferably 1 to 6 carbon atoms), substituted or unsubstituted silyl group, carboxyl group, halogen atom, cyano group, nitro group and hydroxyl group.

However, in the formula (7'), the substituents bonded to the central anthracene in the 9th and 10th positions are not symmetrical with respect to the X-Y axis shown above the anthracene.

Examples for each of $B^1$, $B^2$ and $R^{71}$ to $R^{78}$ are the same as those of the formula (7).

Examples of the anthracene derivative represented by the formula (7) for use in the organic EL device according to the aspect of the invention are known various anthracene derivatives such as an anthracene derivative having two anthracene skeletons in the molecule (see, paragraphs [0043] to [0064] of JP-A-2004-356033) and anthracene derivative having one anthracene skeleton (see, pages 27 to 28 of WO2005/061656). Representative examples are shown below.

[Chemical Formula 21]
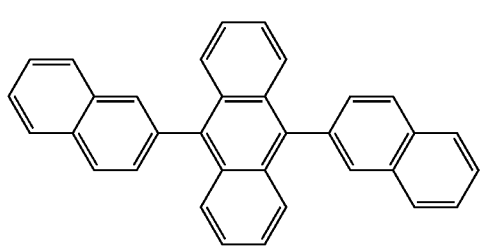
2a-1
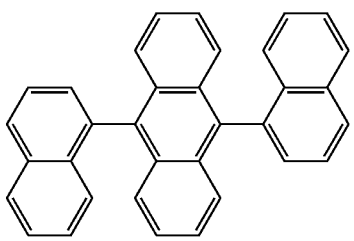
2a-2
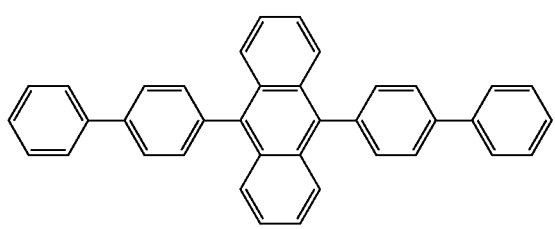
2a-3
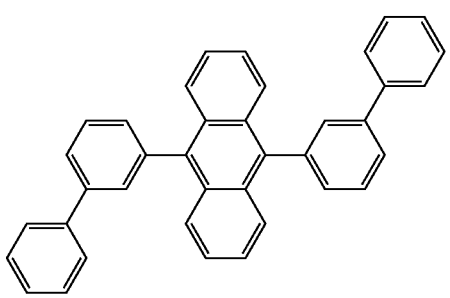
2a-4
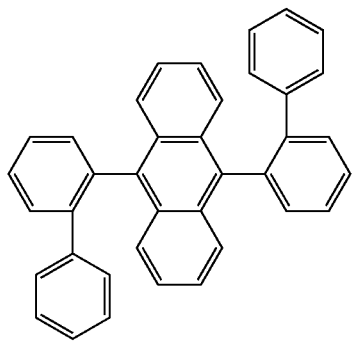
2a-5
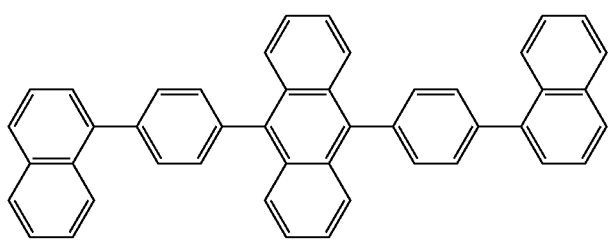
2a-6
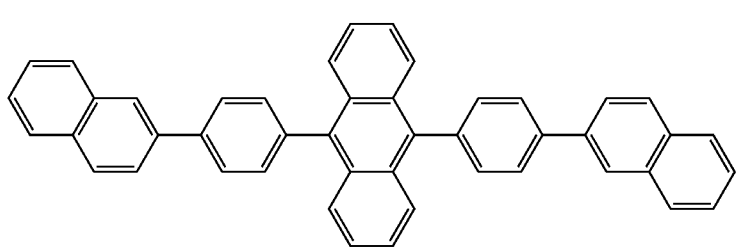
2a-7

-continued
2a-8
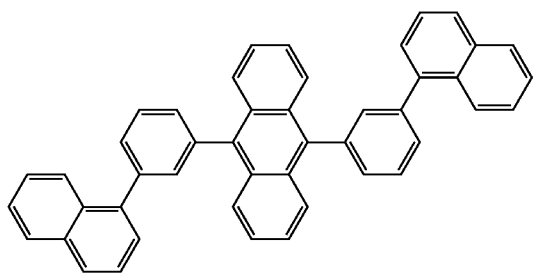
2a-9
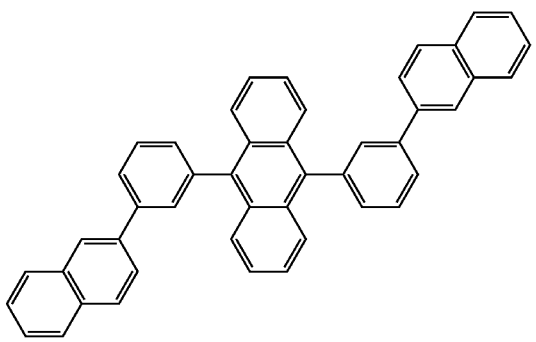
2a-10
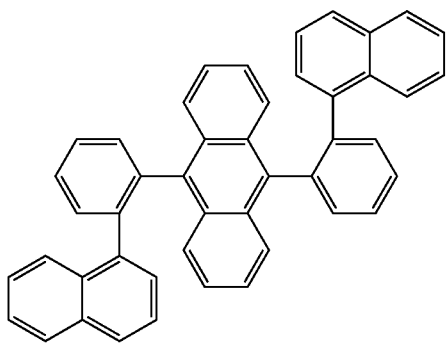
2a-11
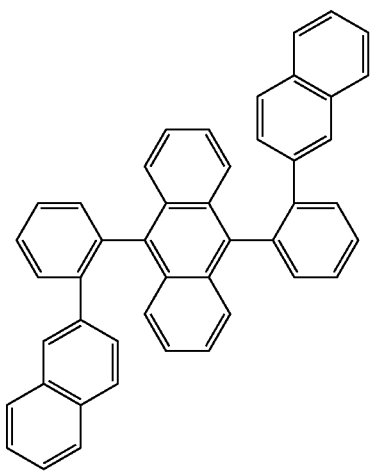
2a-12
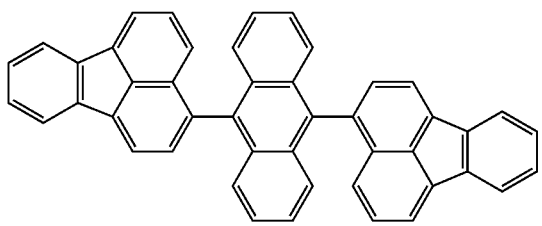
2a-13
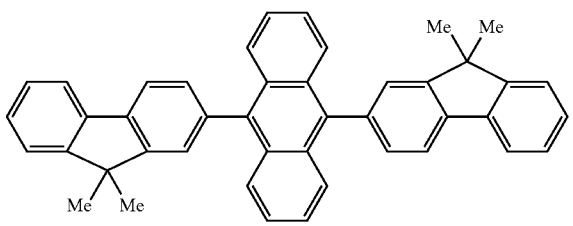
2a-14
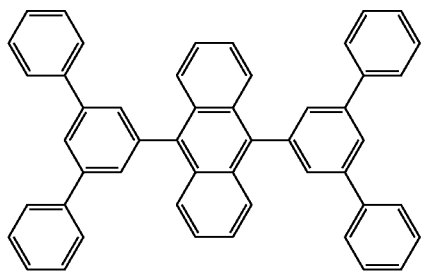
2a-15
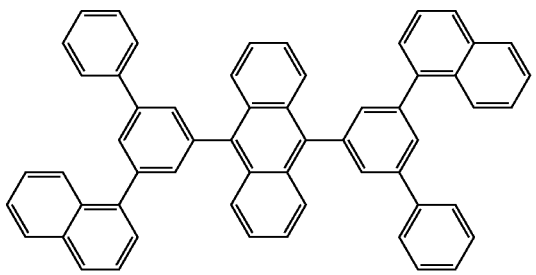

2a-16
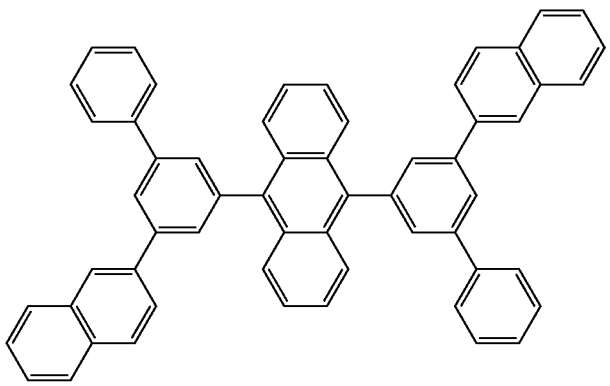
[Chemical Formula 22]
2a-17
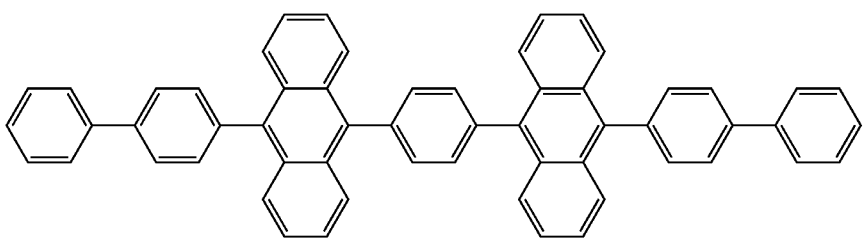
2a-18
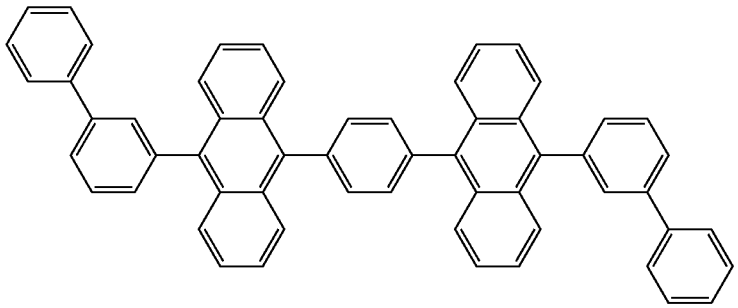
2a-19
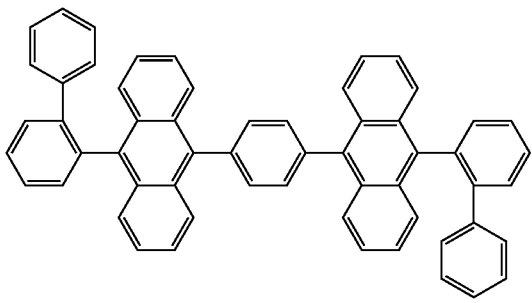
2a-20
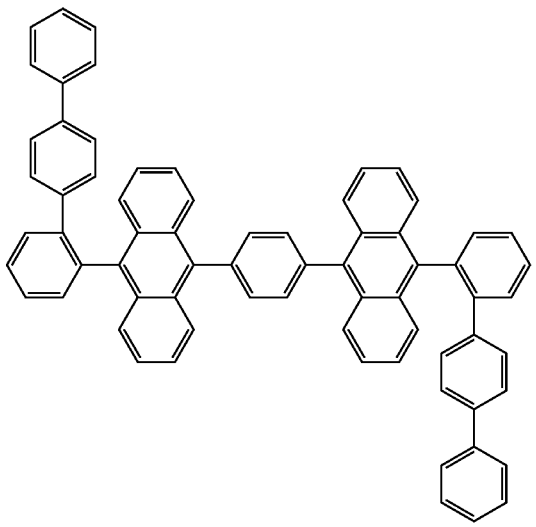

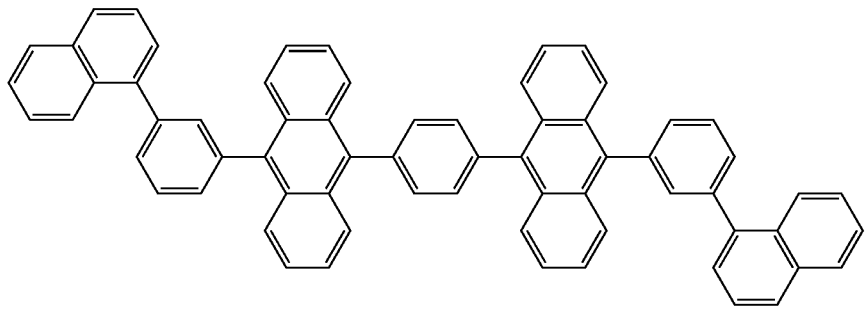

2a-27
2a-28
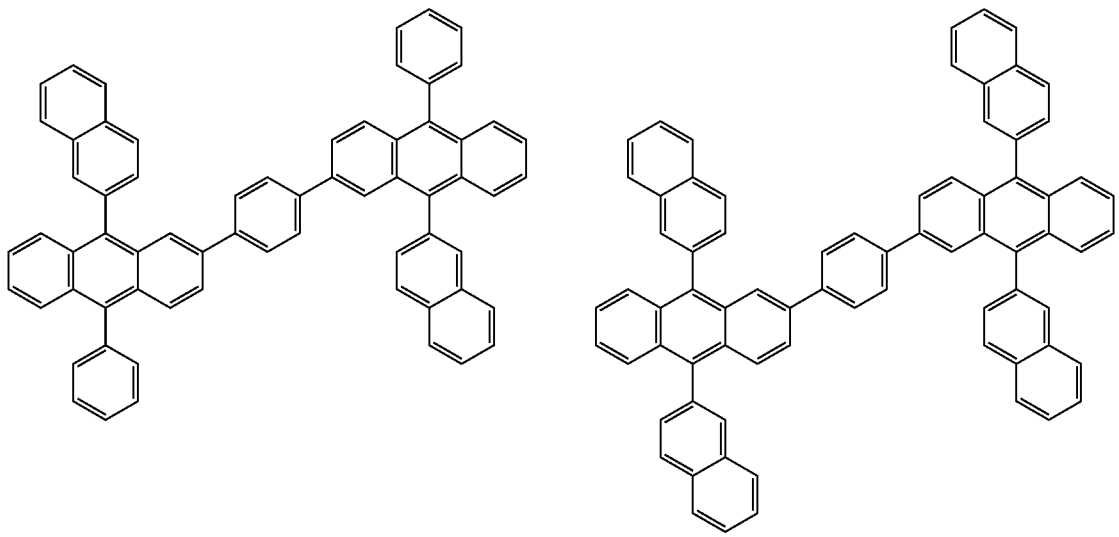
[Chemical Formula 23]
2a-29
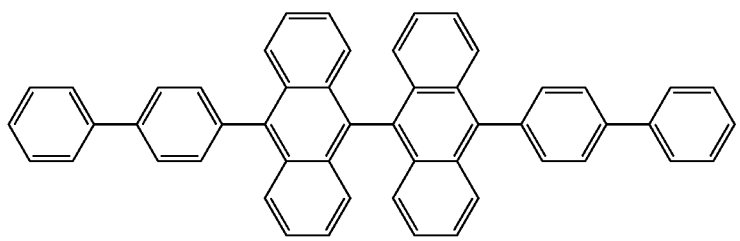
2a-30
2a-31
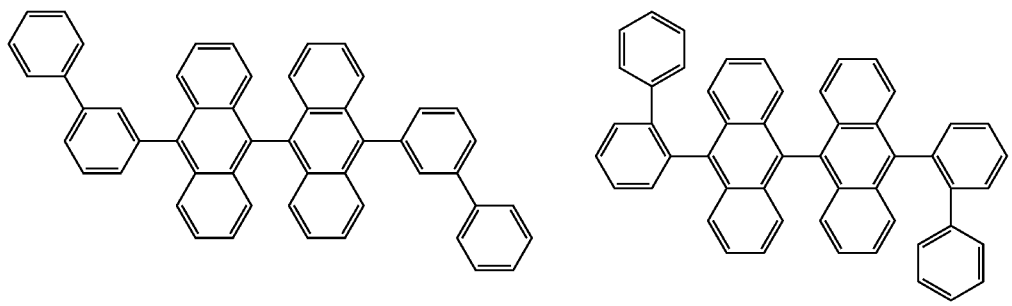
2a-32
2a-33
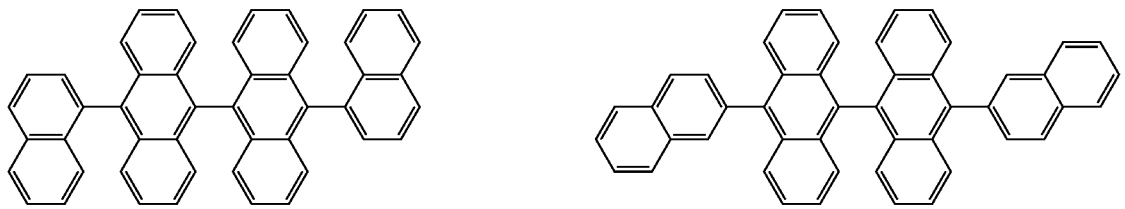

-continued
2a-34
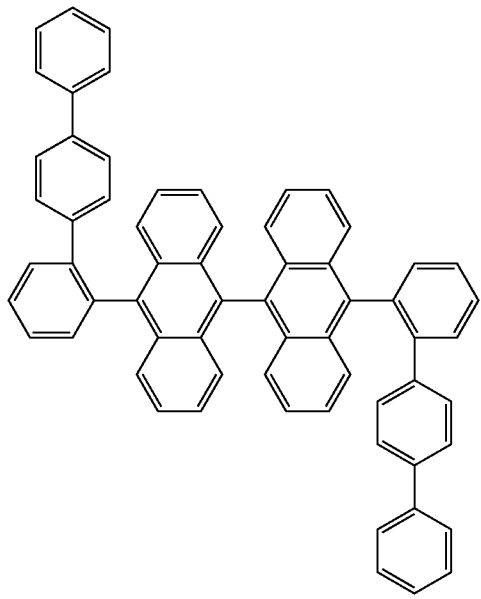
2a-35
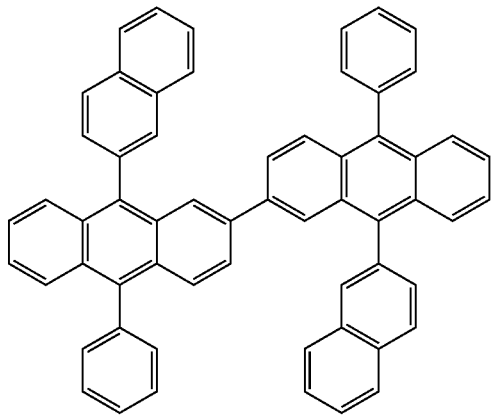
2a-36
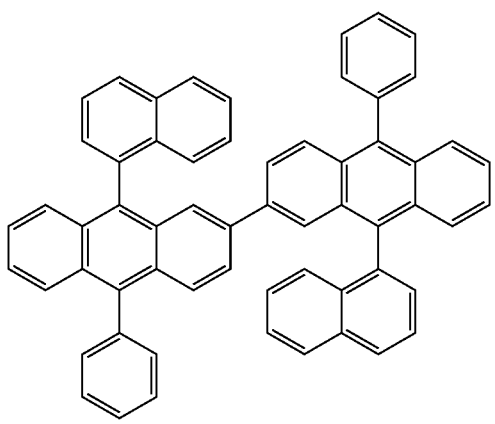
2a-37
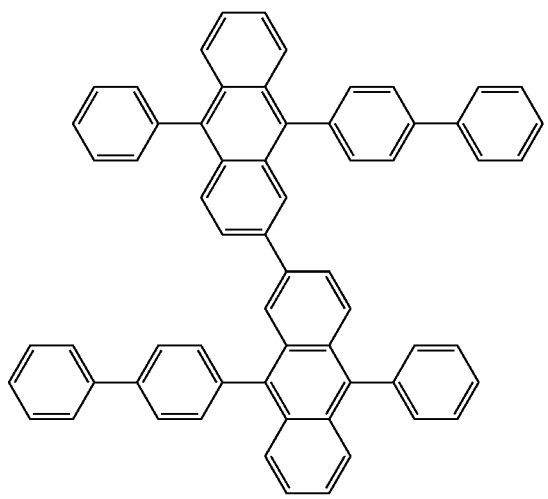
2a-38
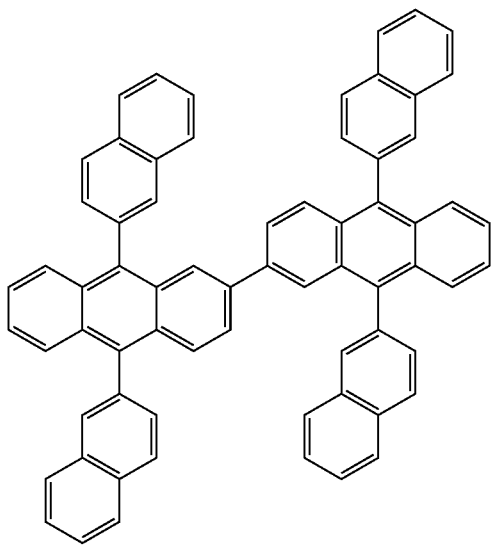
2a-39
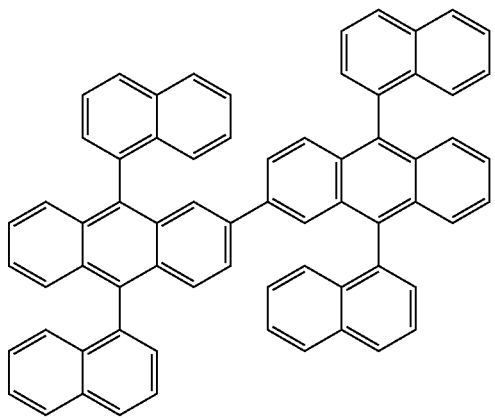

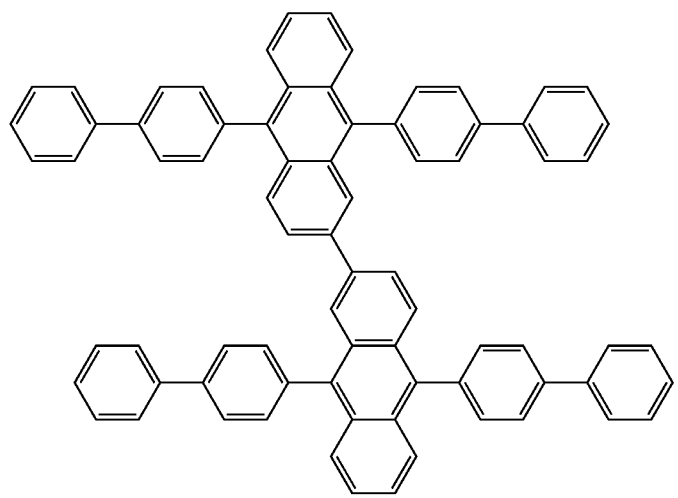
2a-40
[Chemical Formula 24]
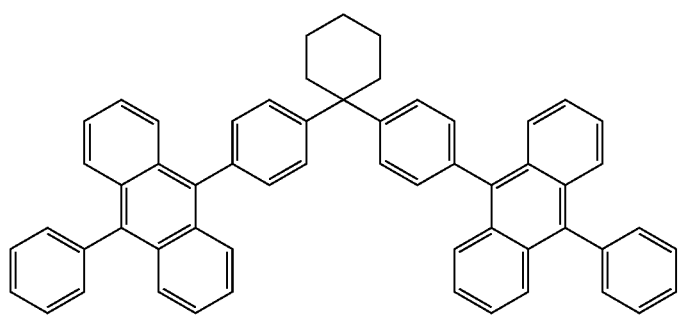
2a-41
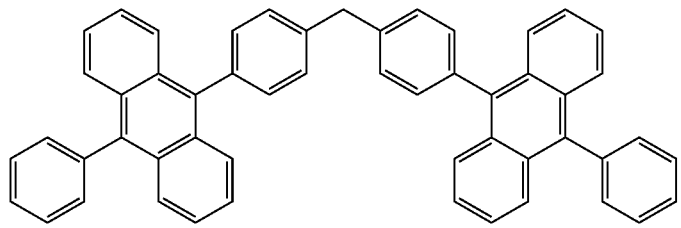
2a-42
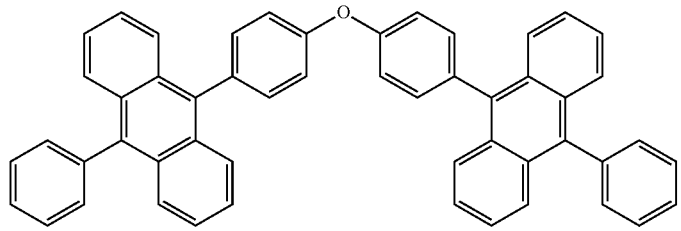
2a-43
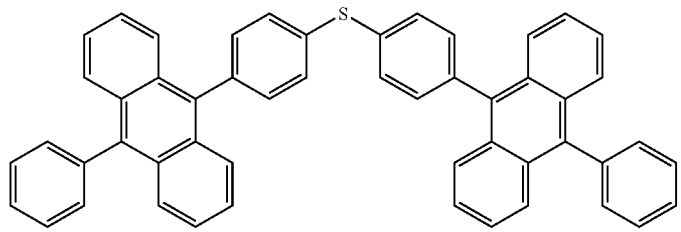
2a-44

-continued
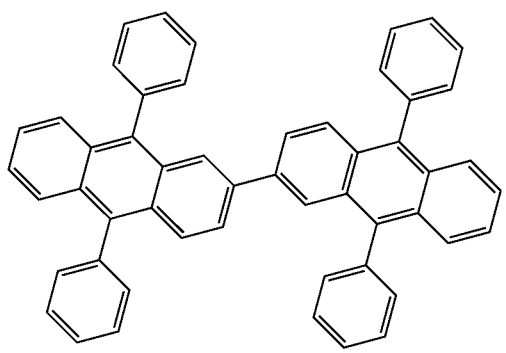
2a-45
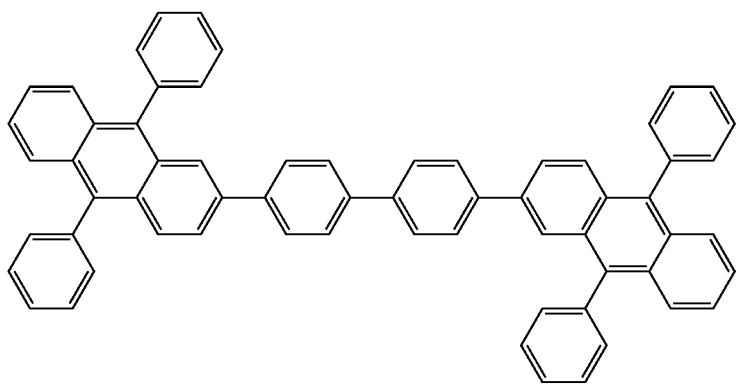
2a-46
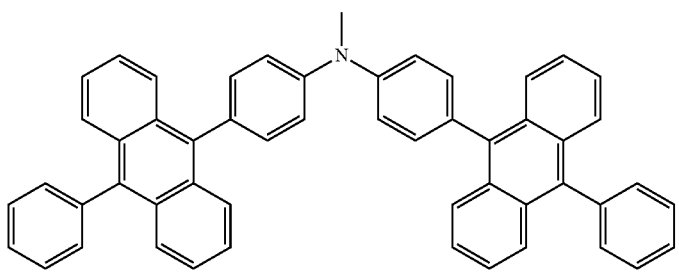
2a-47
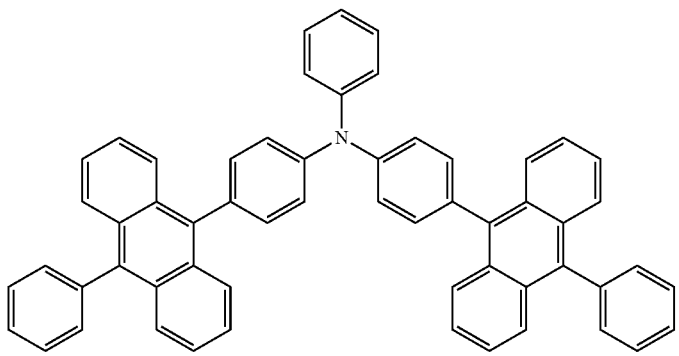
2a-48
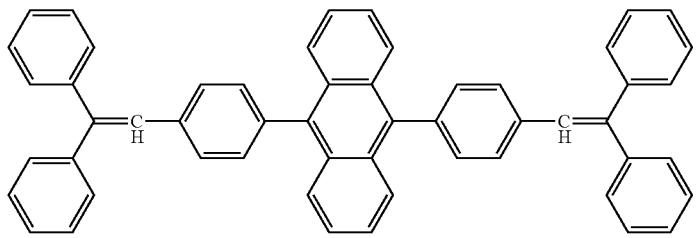
2a-49

-continued
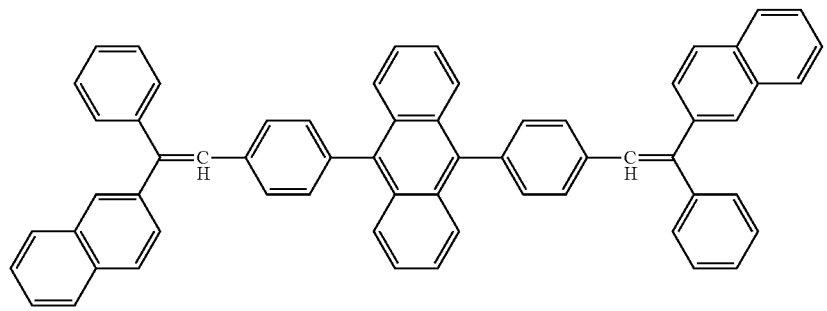
2a-50
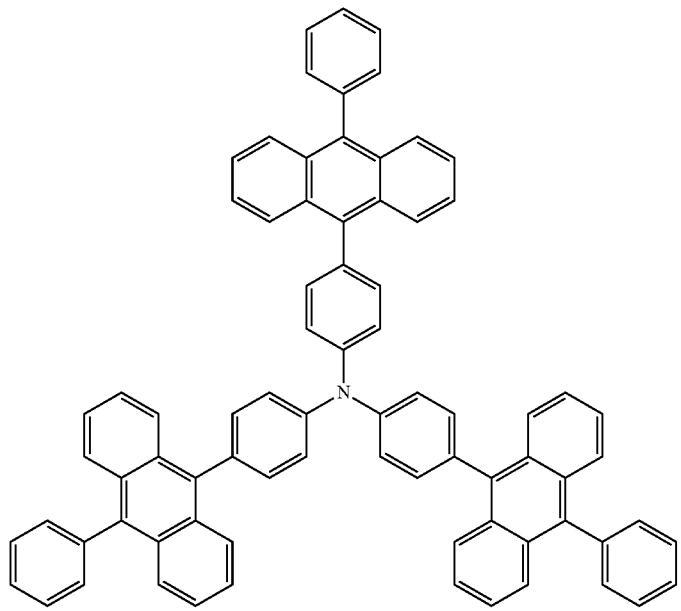
2a-51
[Chemical Formula 25]
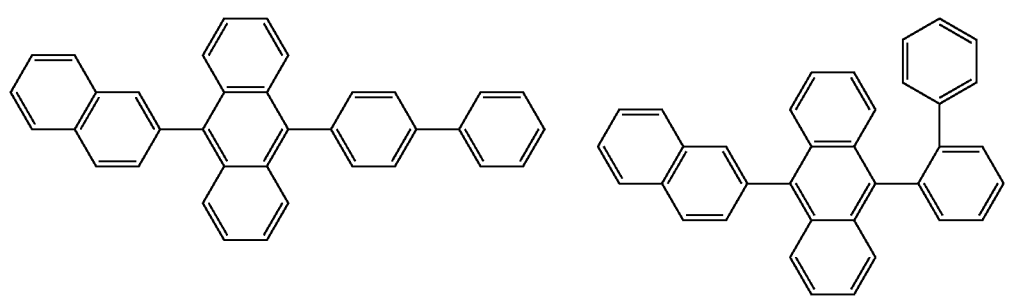
2a'-52         2a'-53
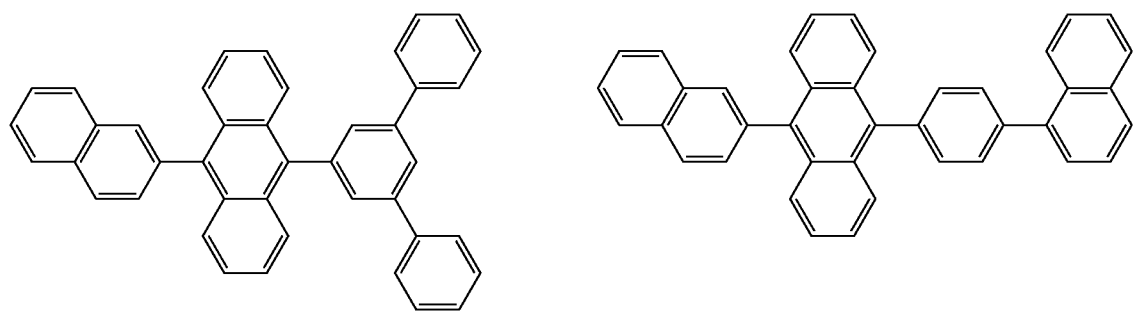
2a'-54         2a'-55

-continued
2a'-56
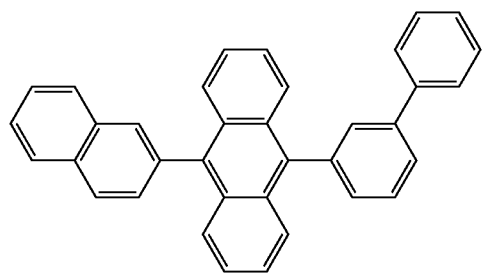
2a'-57
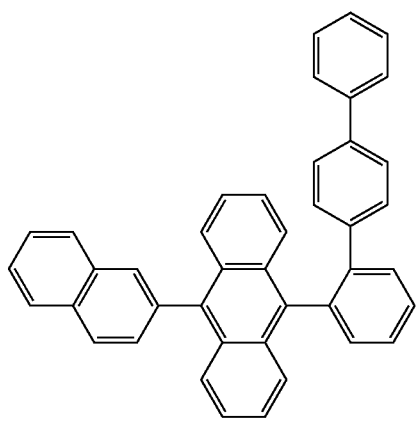
2a'-58
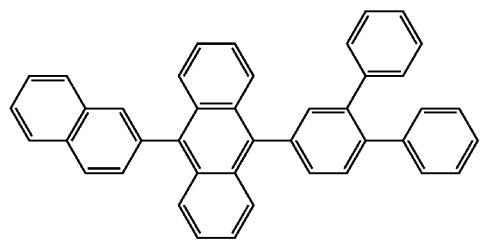
2a'-59
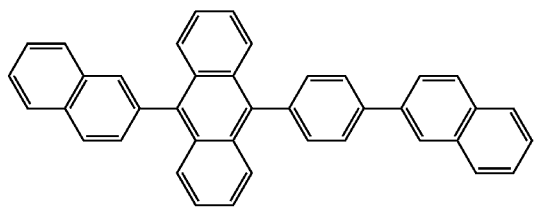
2a'-60
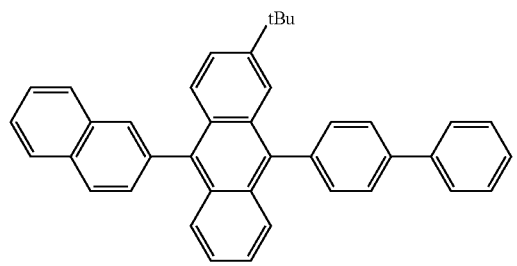
2a'-61
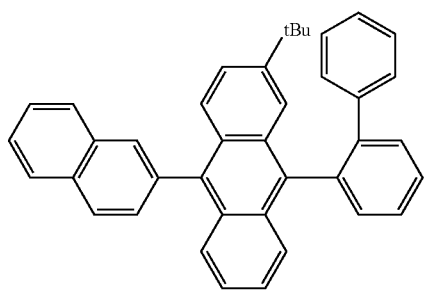
2a'-62
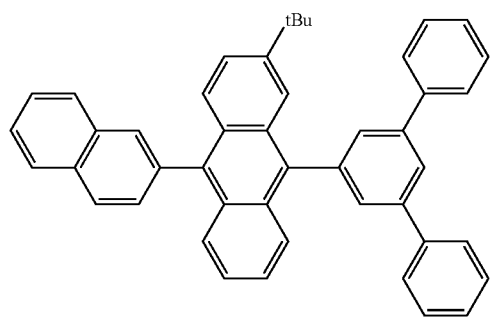
2a'-63
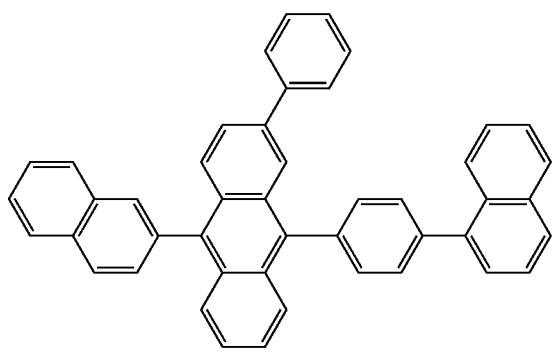

-continued
2a'-64
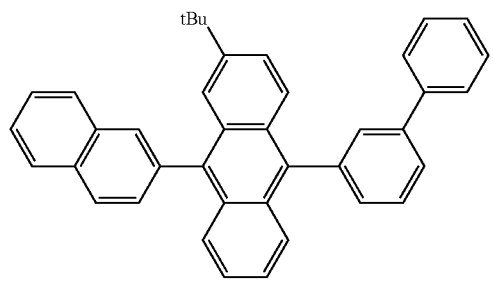
2a'-65
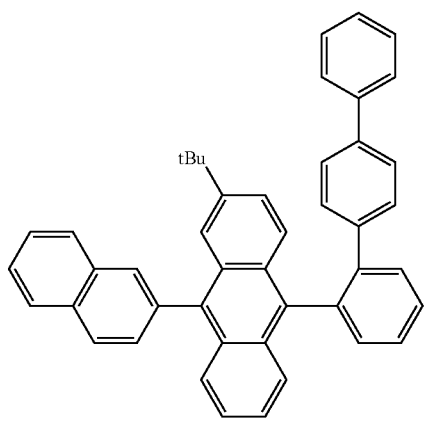
2a'-66
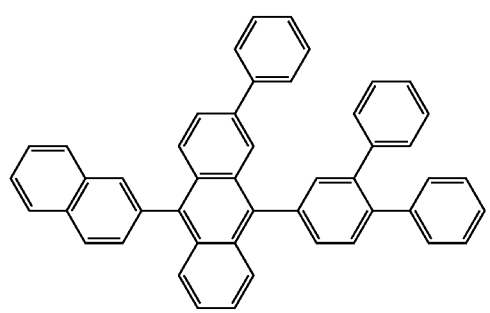
2a'-67
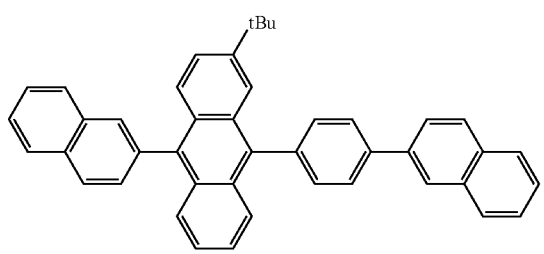
[Chemical Formula 26]
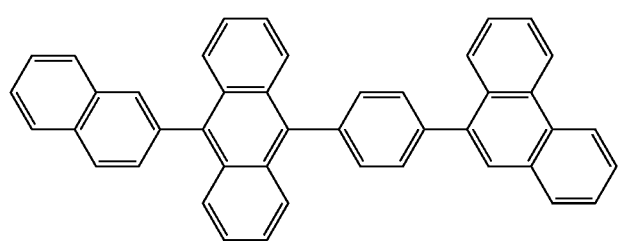
2a'-68
2a'-69
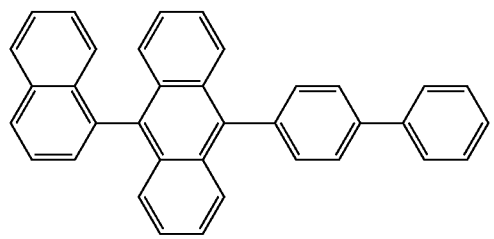
2a'-70
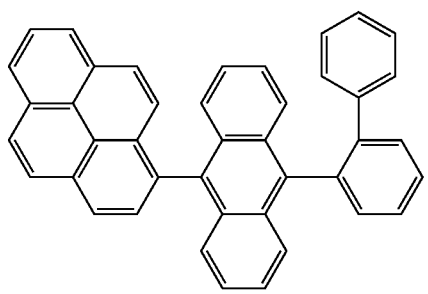
2a'-71
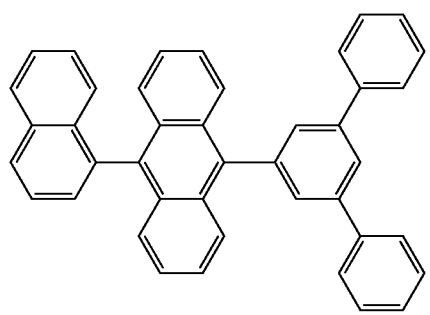

-continued
2a′-72
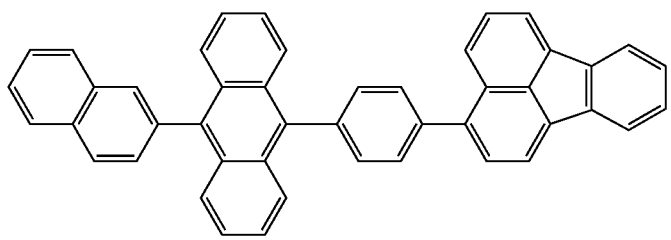
2a′-73
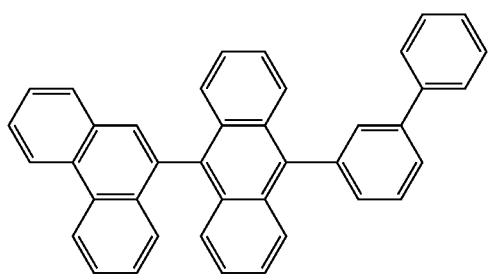
2a′-74
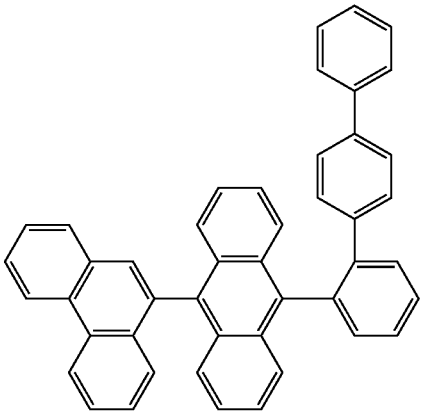
2a′-75
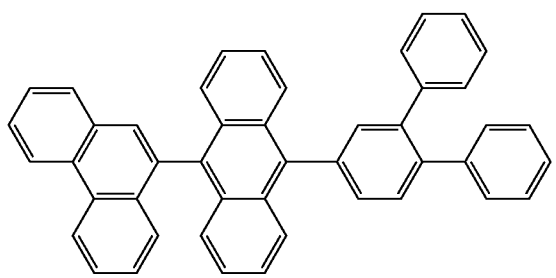
2a′-76
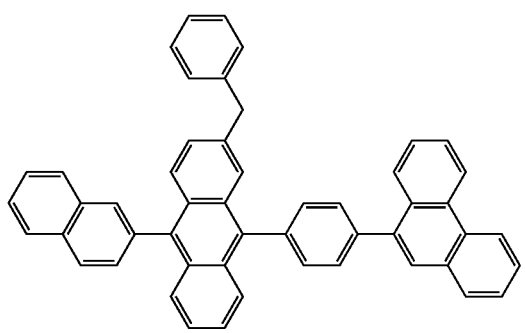
2a′-77
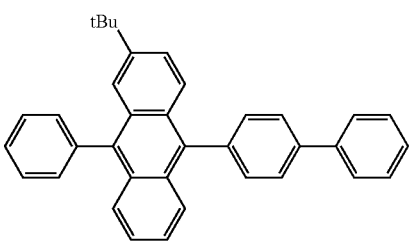
2a′-78
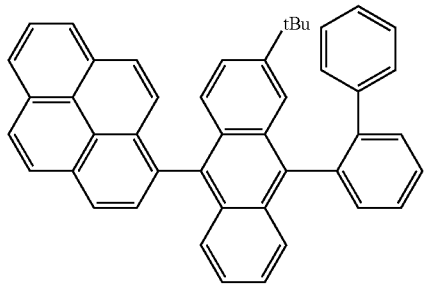
2a′-79
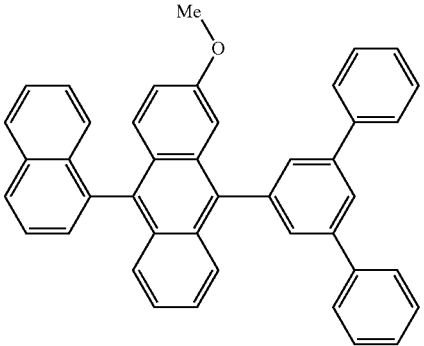

2a′-80
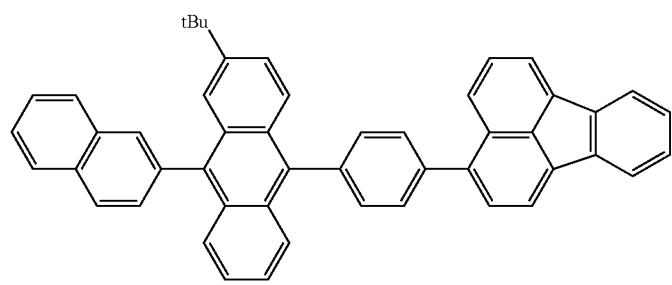
2a′-81
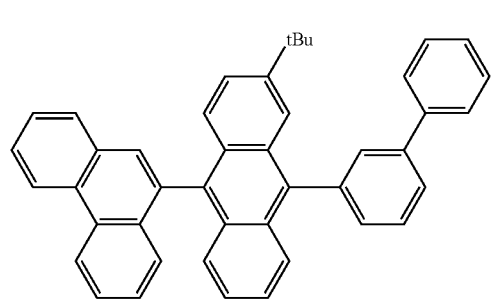
2a′-82
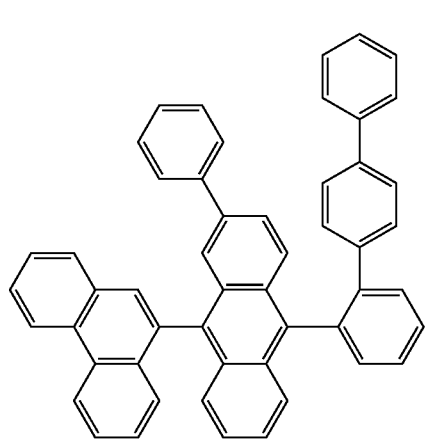
2a′-83
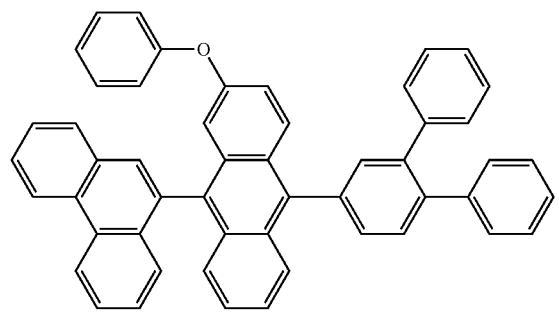
[Chemical Formula 27]
2a′-84
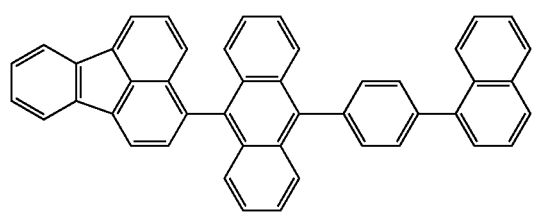
2a′-85
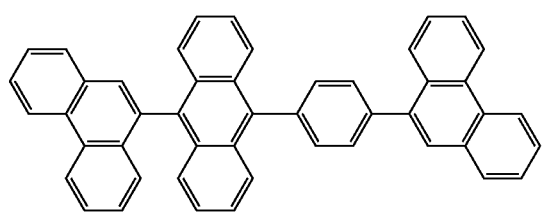

-continued
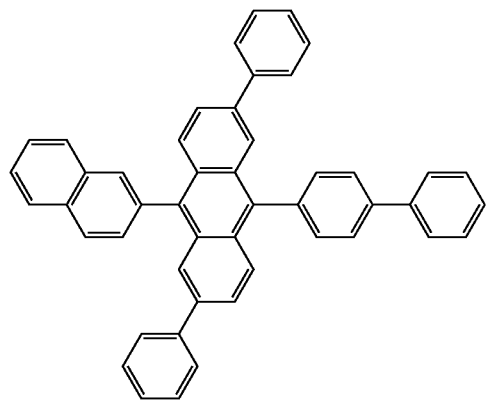

2a'-91
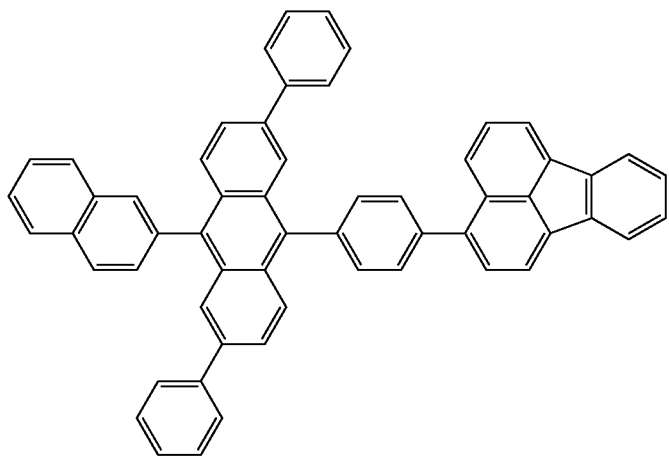
2a'-92
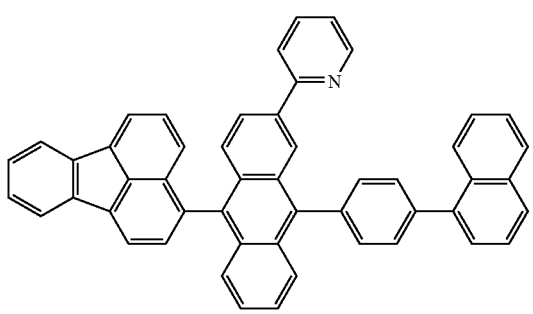
2a'-93
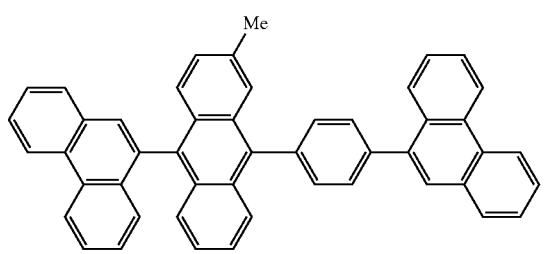
2a'-94
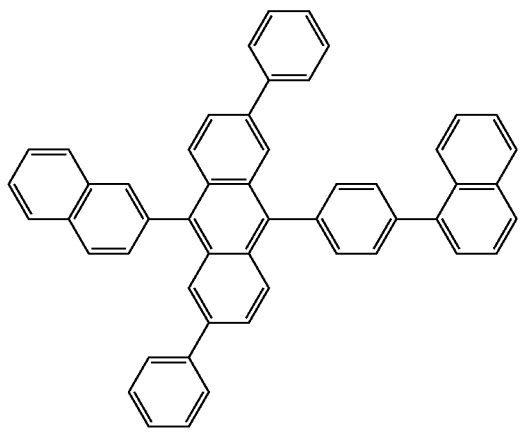
2a'-95
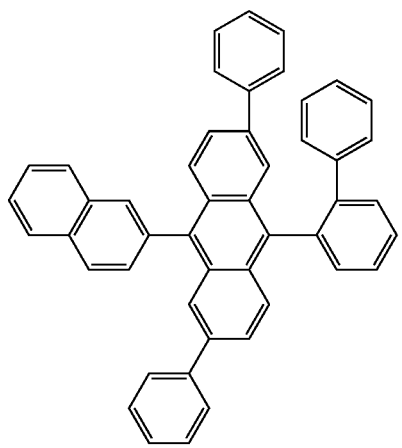
2a'-96
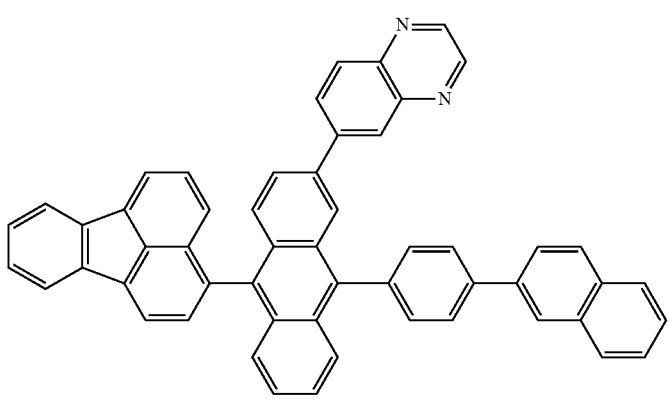

2a'-97
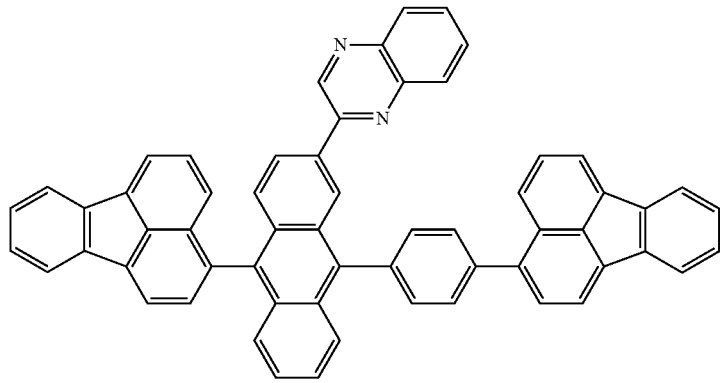
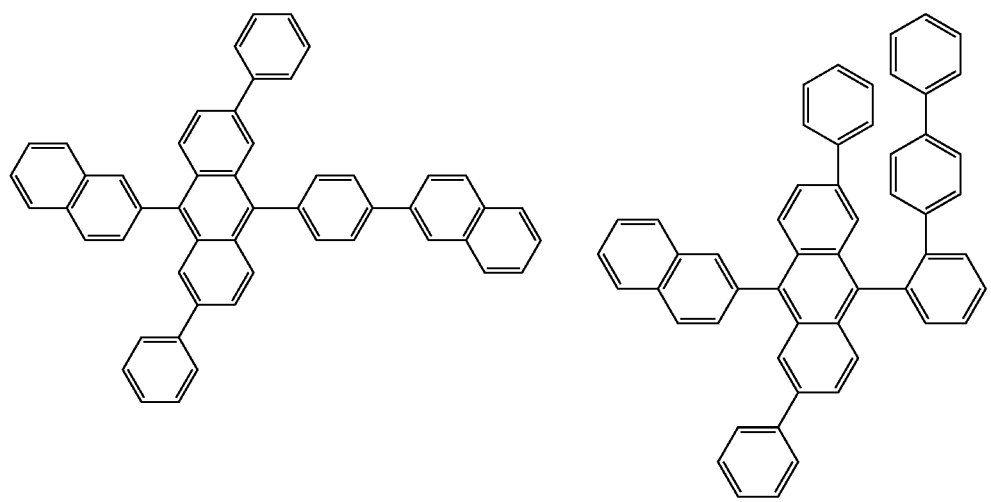
2a'-98    2a'-99
[Chemical Formula 28]
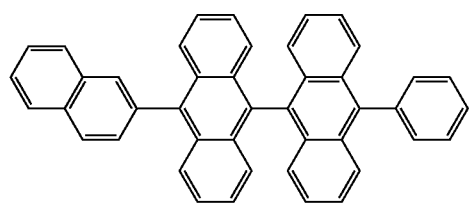
2a'-100
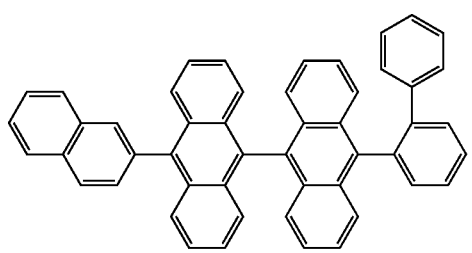
2a'-101
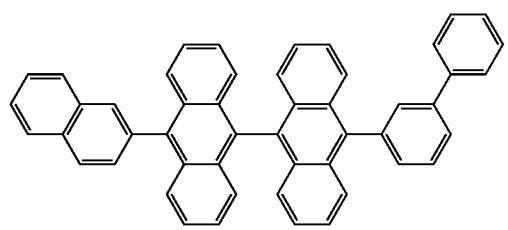
2a'-102
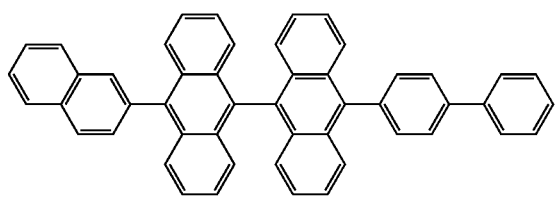
2a'-103

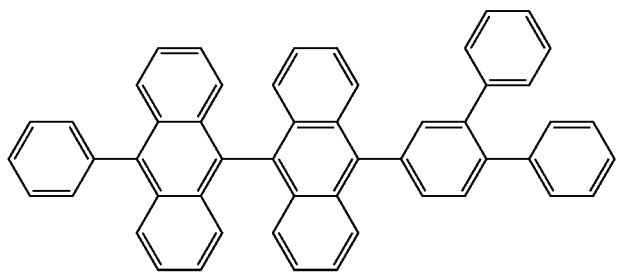
2a′-104
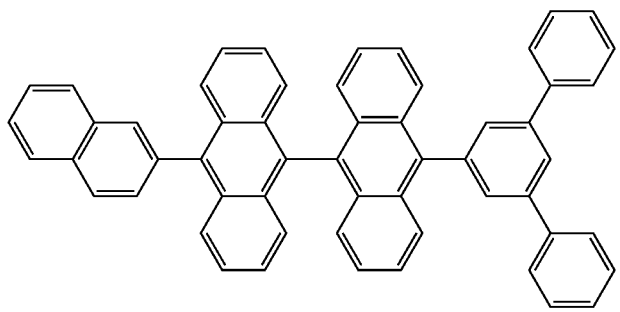
2a′-105
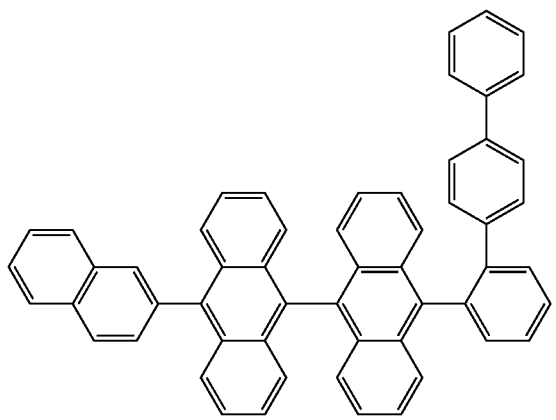
2a′-106
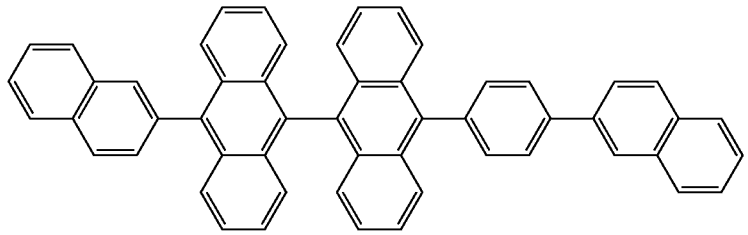
2a′-107
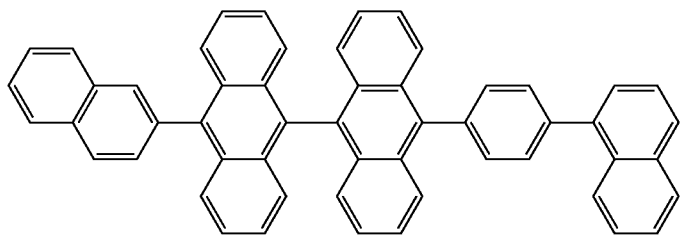
2a′-108

-continued
2a'-109
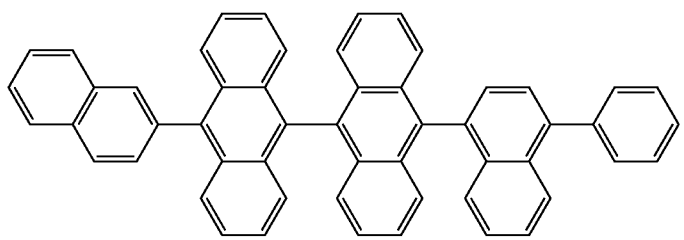
2a'-110
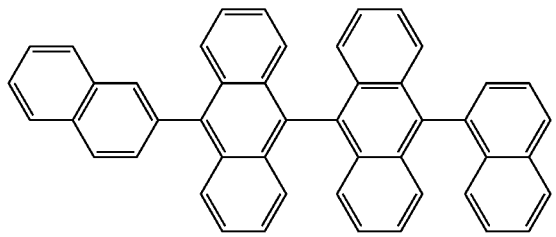
2a'-111
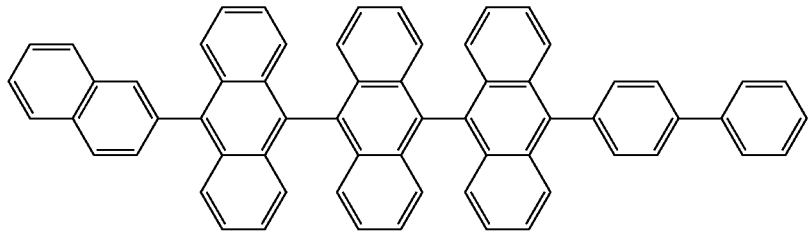
[Chemical Formula 29]
2a'-112
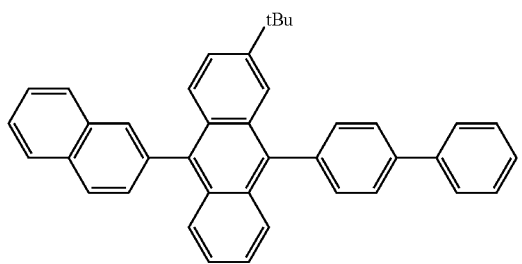
2a'-113
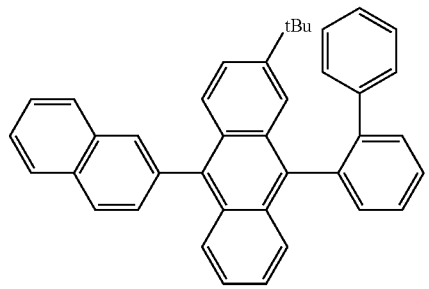
2a'-114
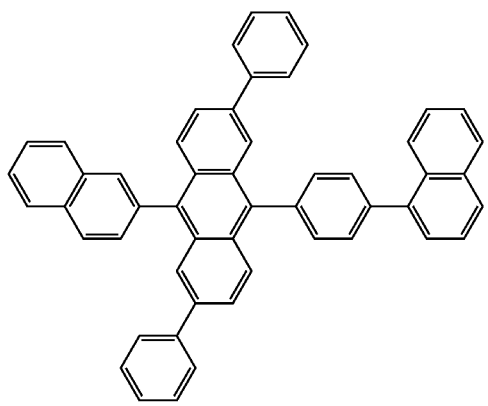
2a'-115
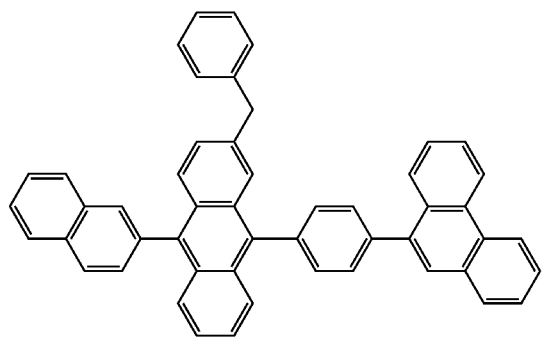

-continued
2a'-116
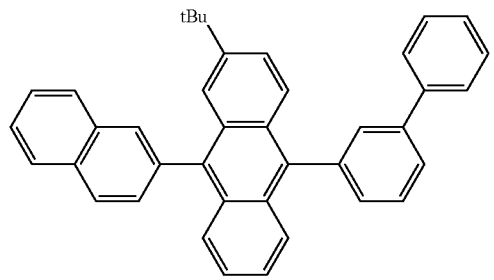
2a'-117
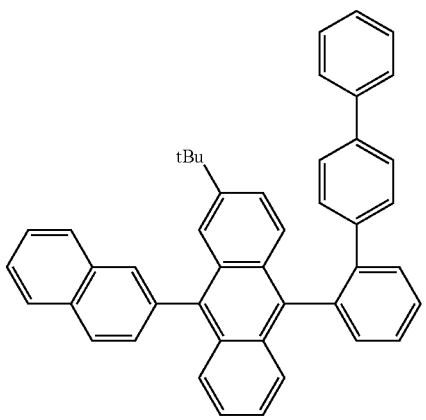
2a'-118
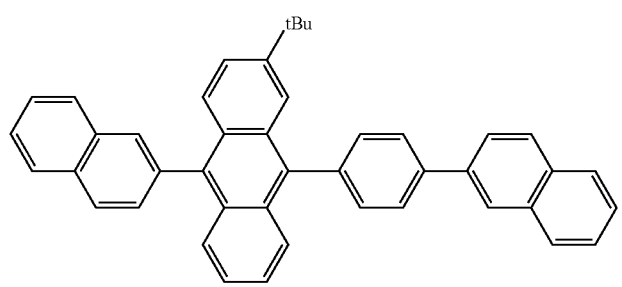
2a'-119
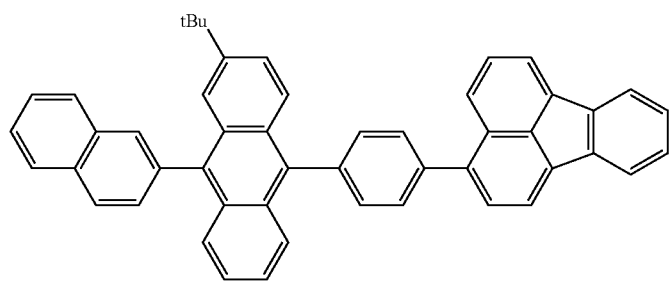
2a'-120
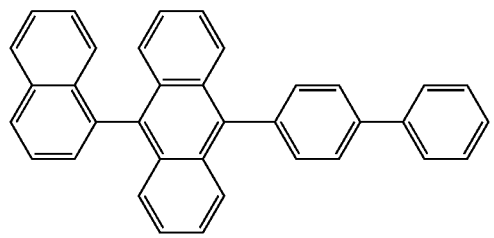
2a'-121
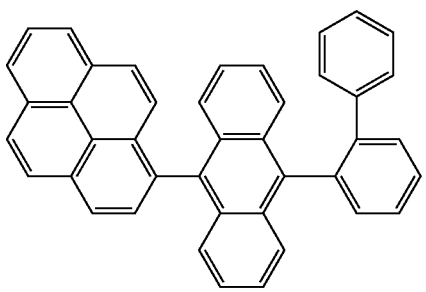
2a'-122
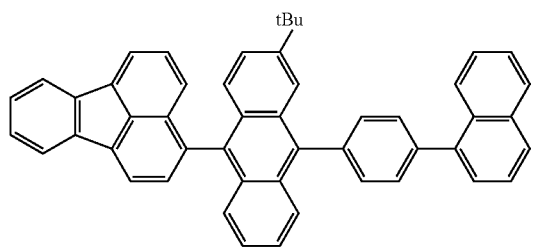
2a'-123
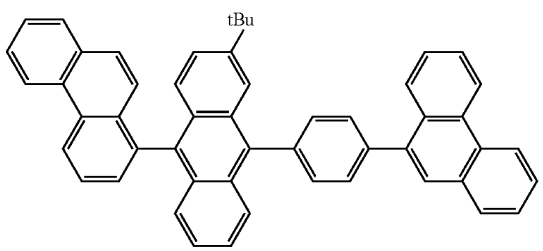

-continued
2a'-124
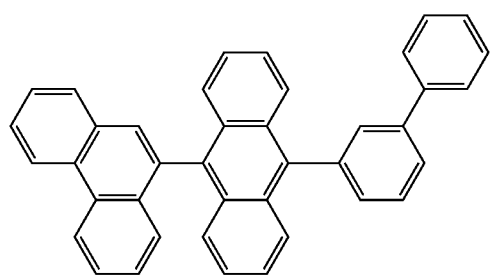
2a'-125
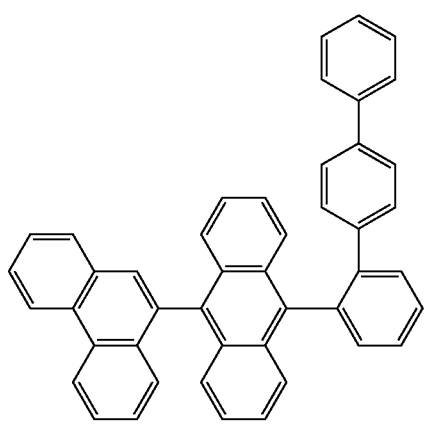
2a'-126
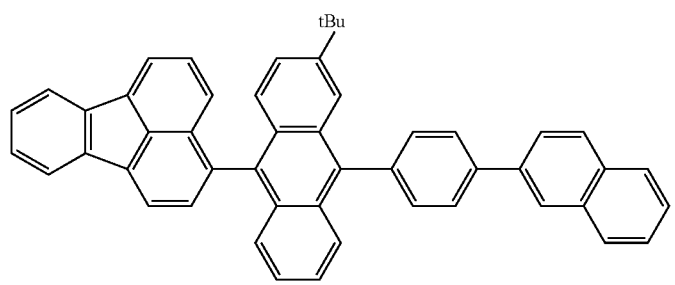
2a'-127
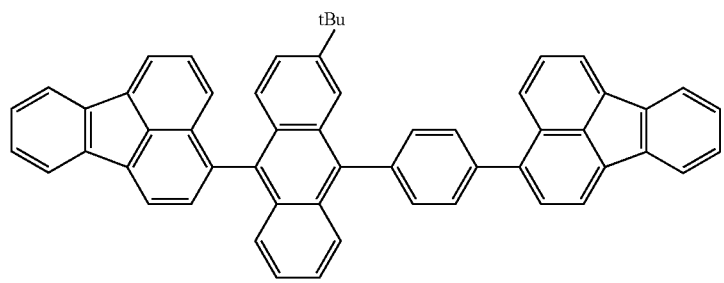
[Chemical Formula 30]
2a'-128
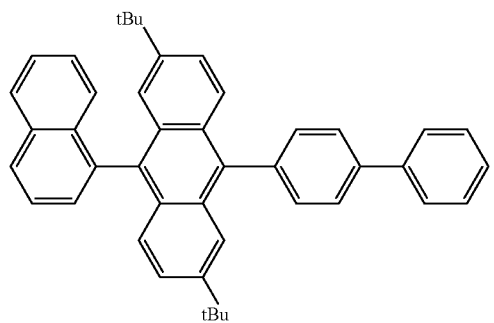
2a'-129
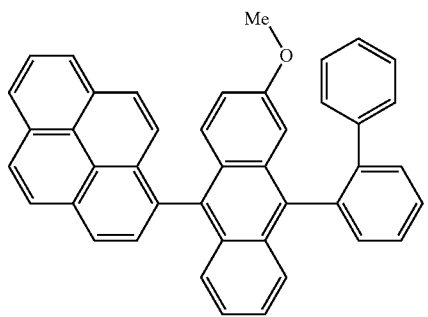

-continued
2a'-130
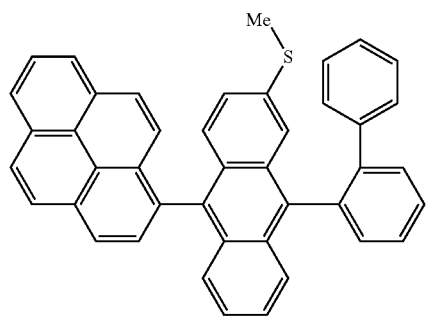
2a'-131
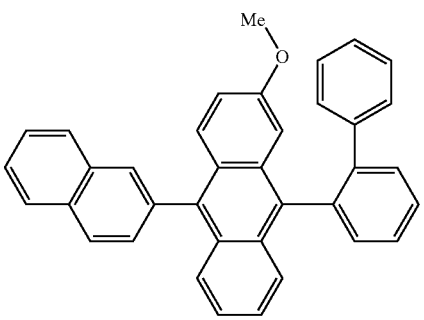
2a'-132
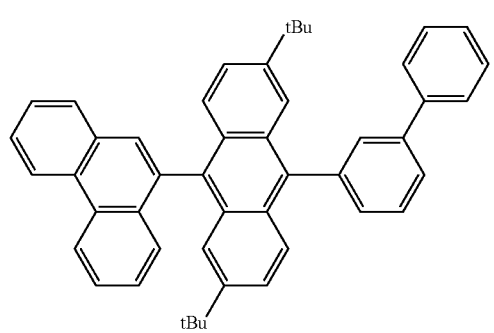
2a'-133
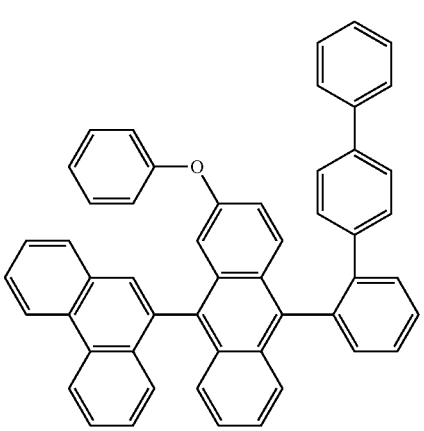
2a'-134
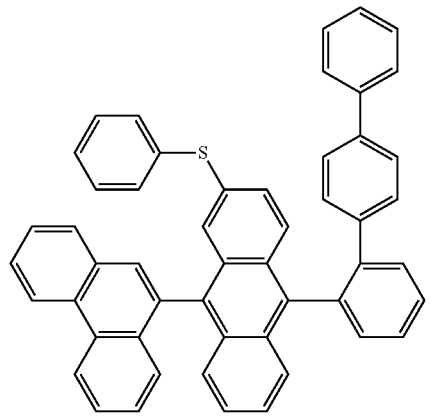
2a'-135
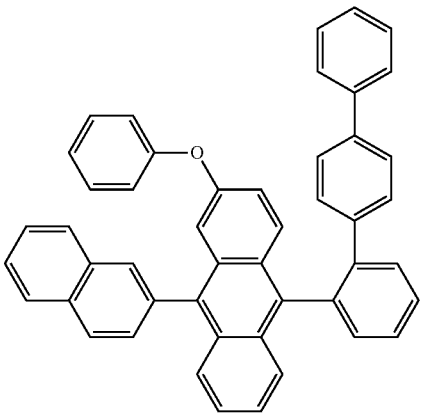
2a'-136
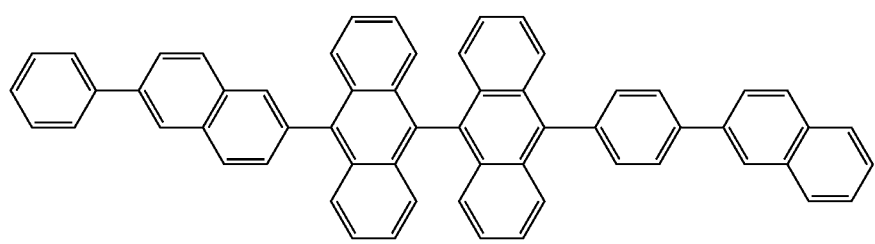
2a'-137
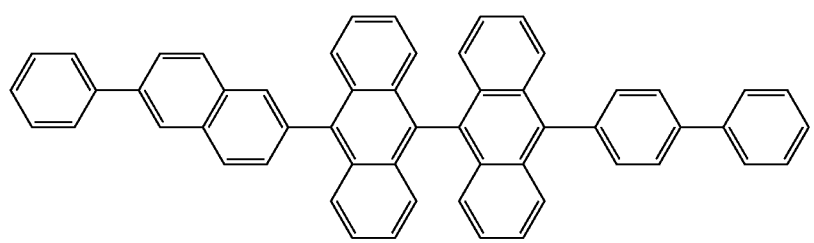

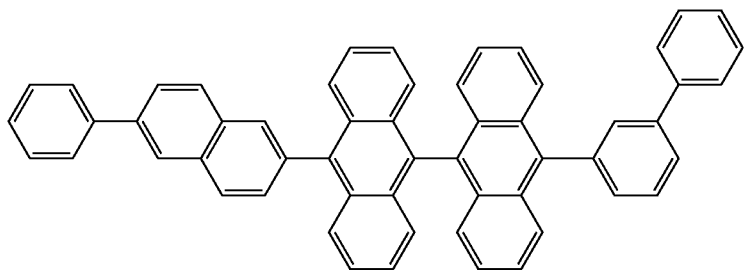
2a'-138
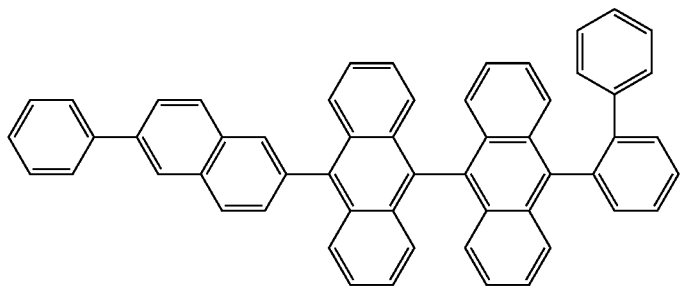
2a'-139
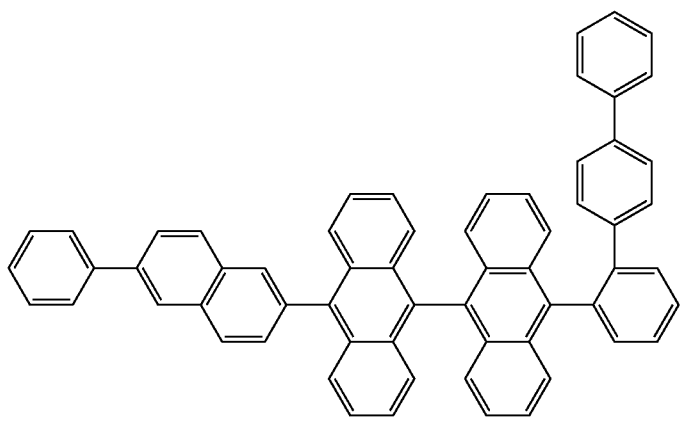
2a'-140
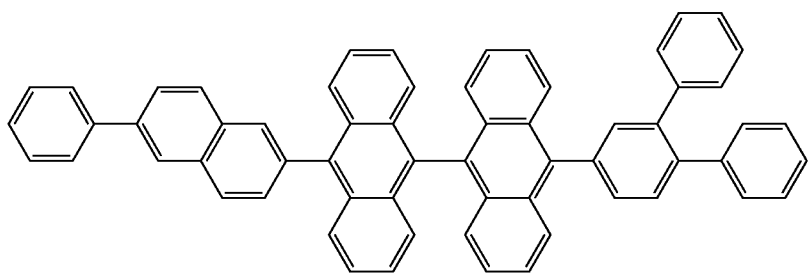
2a'-141
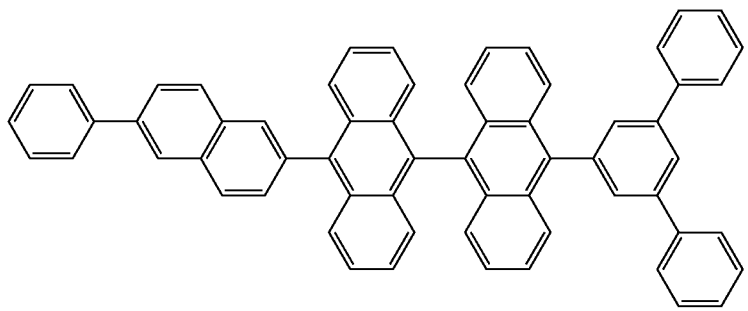
2a'-142

2a'-143

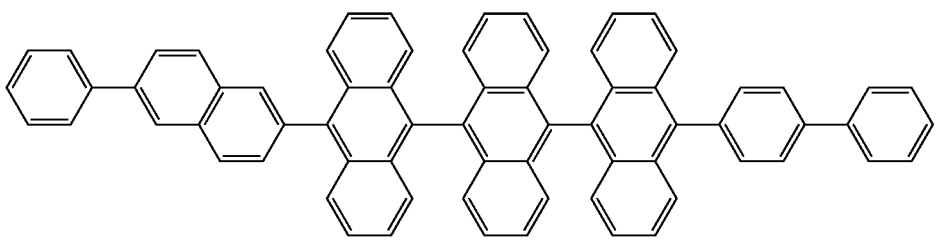

When used as an emitting material, the diaminopyrene derivative according to the aspect of the invention is preferably used together with a compound having a central pyrene skeleton represented by the formula (8).

In the formula (8), $Ar^{81}$ and $Ar^{82}$ each independently represent a substituted or unsubstituted aryl group having 6 to 50 carbon atoms for forming the ring.

Examples of the aryl group having 6 to 50 ring carbon atoms for $Ar^{81}$ and $Ar^{82}$ in the formula (8) are a phenyl group, 1-naphthyl group, 2-naphthyl group, 1-anthryl group, 2-anthryl group, 9-anthryl group, 9-(10-phenyl)anthryl group, 9-(10-naphthyl-1-yl)anthryl group, 9-(10-naphthyl-2-yl)anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, 3-methyl-2-naphthyl group, 4-methyl-1-naphthyl group and 4-methyl-1-anthryl group. The aryl group is preferably an aromatic ring group having 6 to 16 ring carbon atoms. Particularly preferable are a phenyl group, 1-naphthyl group, 2-naphthyl group, 9-(10-phenyl)anthryl group, 9-(10-naphthyl-1-yl)anthryl group, 9-(10-naphthyl-2-yl)anthryl group, 9-phenanthryl group, 1-pyrenyl group, 2-pyrenyl group, 4-pyrenyl group, 2-biphenylyl group, 3-biphenylyl group, 4-biphenylyl group, o-tolyl group, m-tolyl group, p-tolyl group and p-t-butylphenyl group.

The aryl group may be substituted. Examples of the substituent are an alkyl group (e.g., methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group, cyclopropyl group, cyclobutyl group, cyclopentyl group cyclohexyl group, 4-methylcyclohexyl group, 1-adamantyl group, 2-adamantyl group, 1-norbornyl group and 2-norbornyl group), alkoxy group having 1 to 6 carbon atoms (e.g., ethoxy group, methoxy group, i-propoxy group, n-propoxy group, s-butoxy group, t-butoxy group, pentoxy group, hexyloxy group, cyclopentoxy group, cyclohexyloxy group), aryl group having 5 to 40 ring atoms, amino group substituted by an aryl group having 5 to 40 ring atoms, ester group having an aryl group having 5 to 40 ring atoms, ester group having an alkyl group having 1 to 6 carbon atoms, cyano group, nitro group and halogen atom.

$L^{81}$ and $L^{82}$ in the formula (8) are each independently selected from a substituted or unsubstituted phenylene group, substituted or unsubstituted naphthalenylene group, substituted or unsubstituted fluorenylene group and substituted or unsubstituted dibenzo-sylolylene group.

$L^{81}$ and $L^{82}$ are preferably selected from a substituted or unsubstituted phenylene group and substituted or unsubstituted fluorenylene group.

Examples of the substituent are the same as those enumerated as the substituent for the aryl group.

m in the formula (8) is preferably an integer of 0 to 1. n in the formula (8) is preferably an integer of 1 to 2. 0 in the formula (8) is preferably an integer of 0 to 1. v in the formula (8) is preferably an integer of 0 to 2.

$L^{81}$ or $Ar^{81}$ is bonded to the pyrene in one of the 1st to 5th positions, and $L^{82}$ or $Ar^{82}$ is bonded to the pyrene in one of the 6th to 10th positions.

Examples of the pyrene derivative represented by the formula (8) for use in the organic EL device according to the aspect of the invention are asymmetrical pyrene derivatives disclosed in paragraphs [0020] to [0023] of WO2005/115950. In addition to the above, symmetrical pyrene derivatives are also usable as the material for the organic EL device according to the aspect of the invention. Representative examples are shown below.

[Chemical Formula 31]
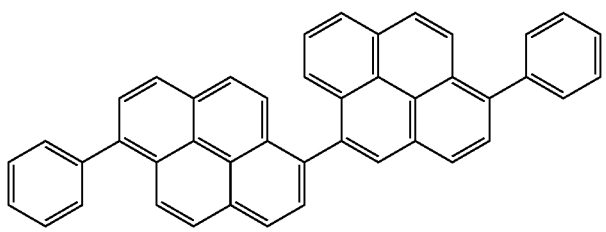
2b-1
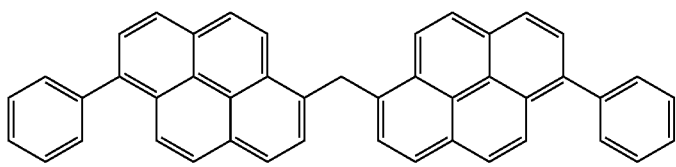
2b-2
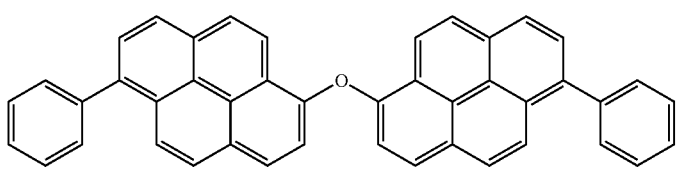
2b-3
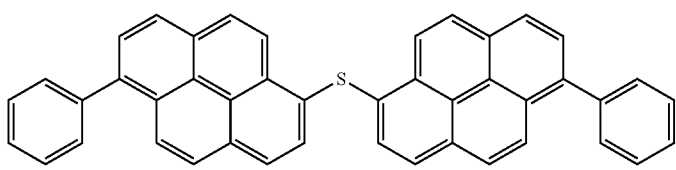
2b-4
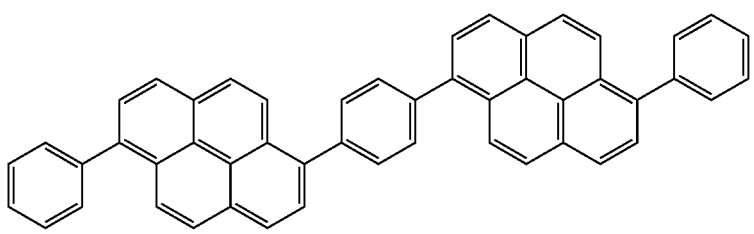
2b-5
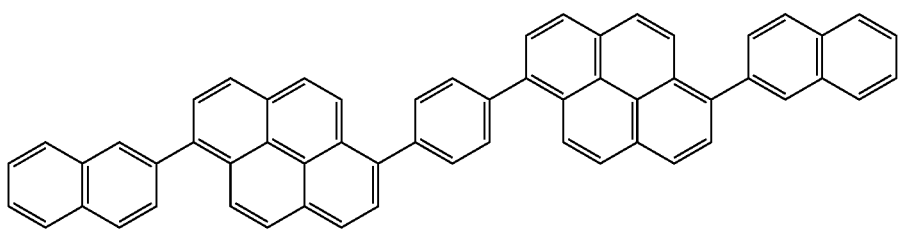
2b-6
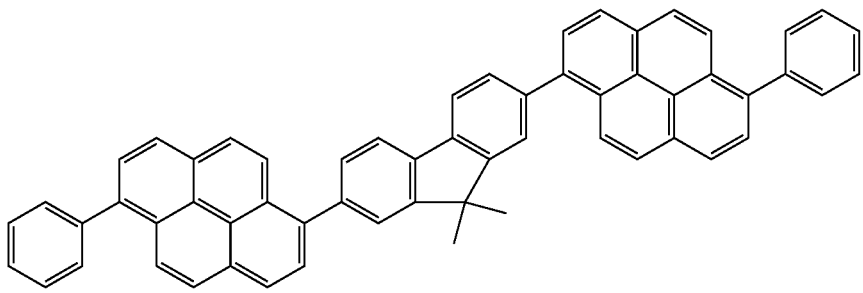
2b-7

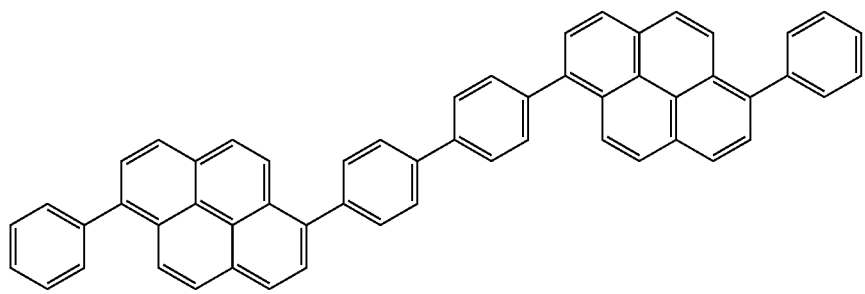
2b-8
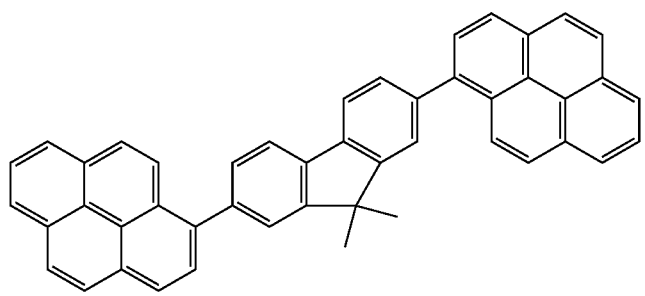
2b-9
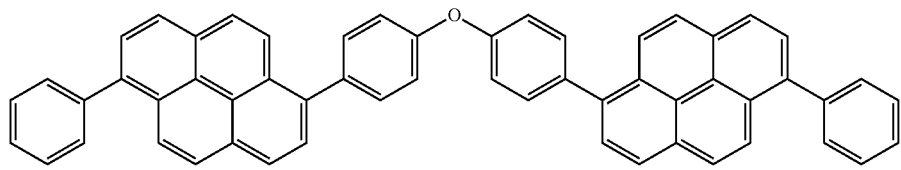
2b-10
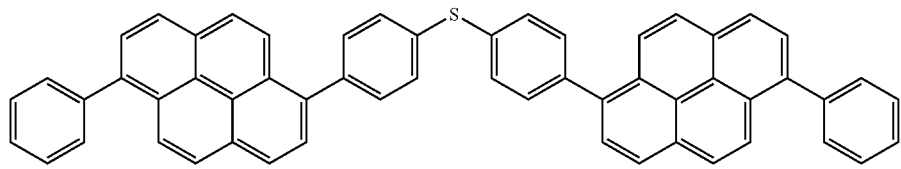
2b-11
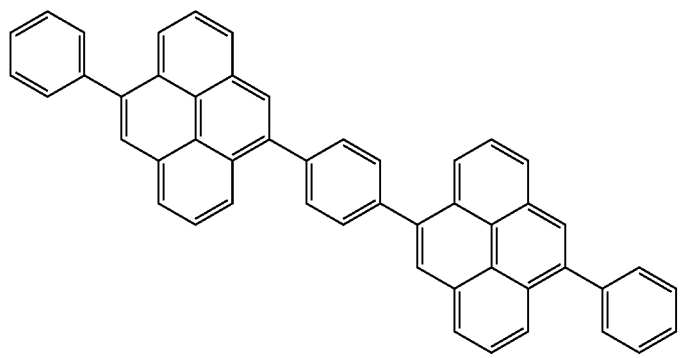
2b-12

[Chemical Formula 32]
2b-13
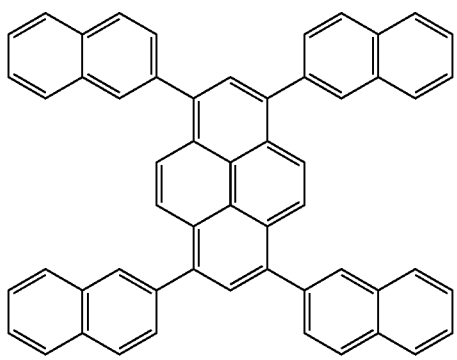
2b-14
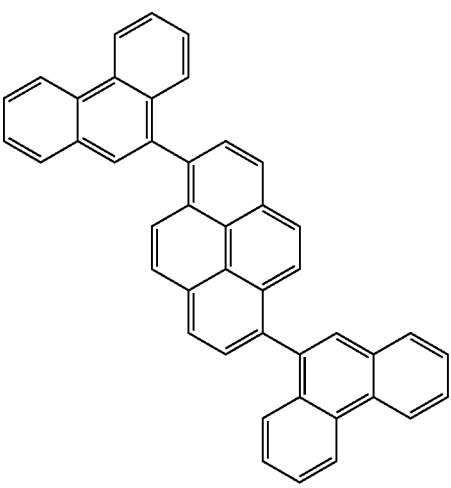
2b-15
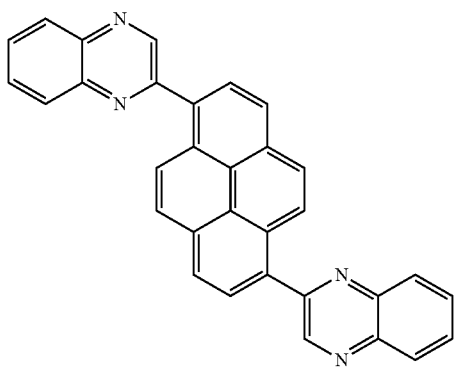
2b-16
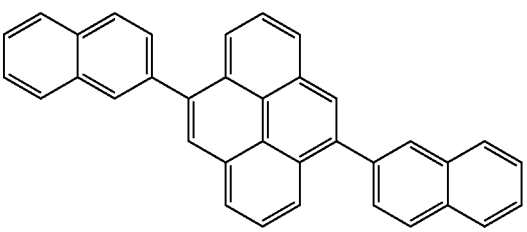
2b-17
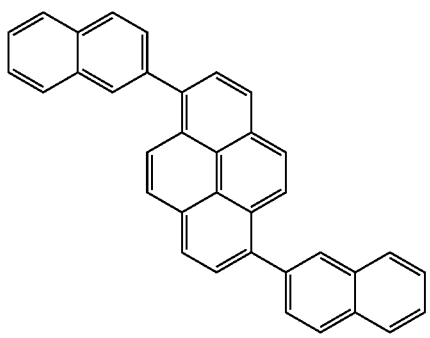
2b-18
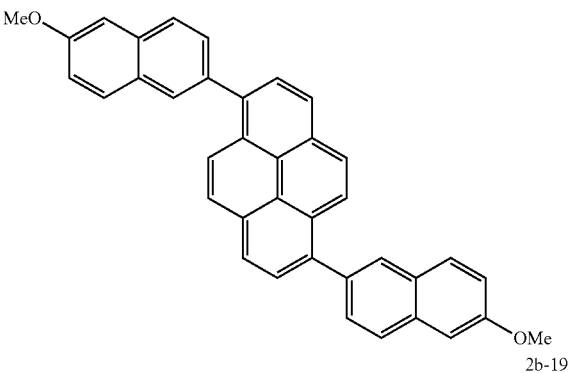
2b-19
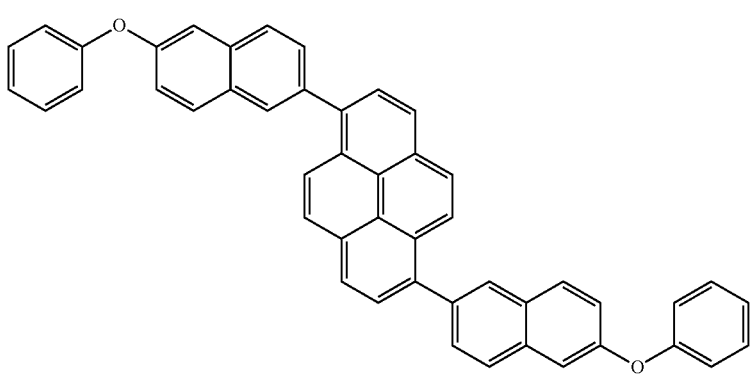

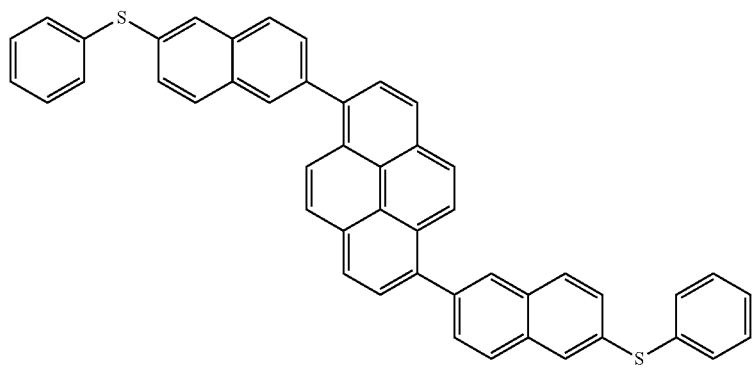
2b-20
[Chemical Formula 33]
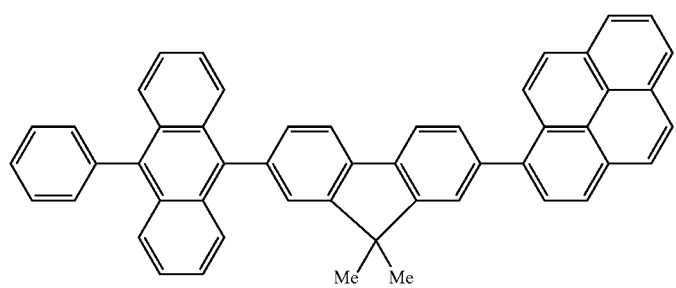
2b-21
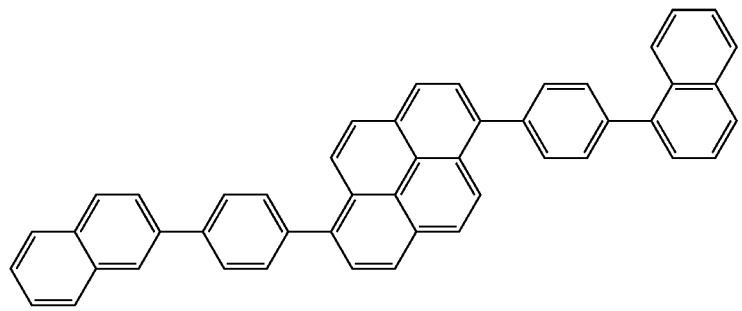
2b-22
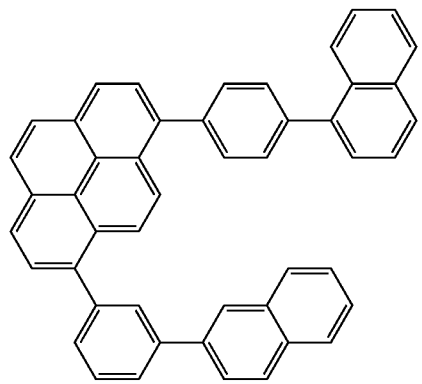
2b-23

-continued
2b-24
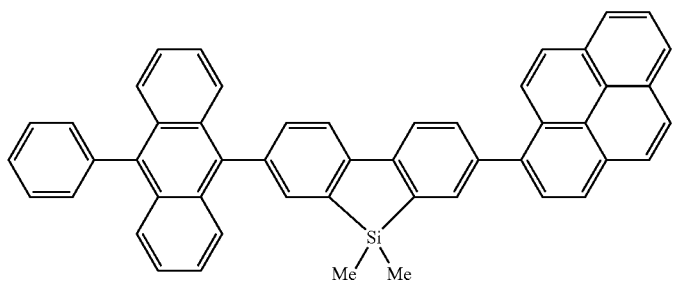
2b-25
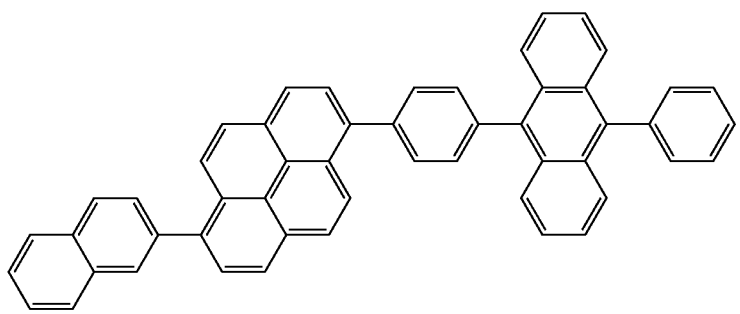
2b-26 2b-27
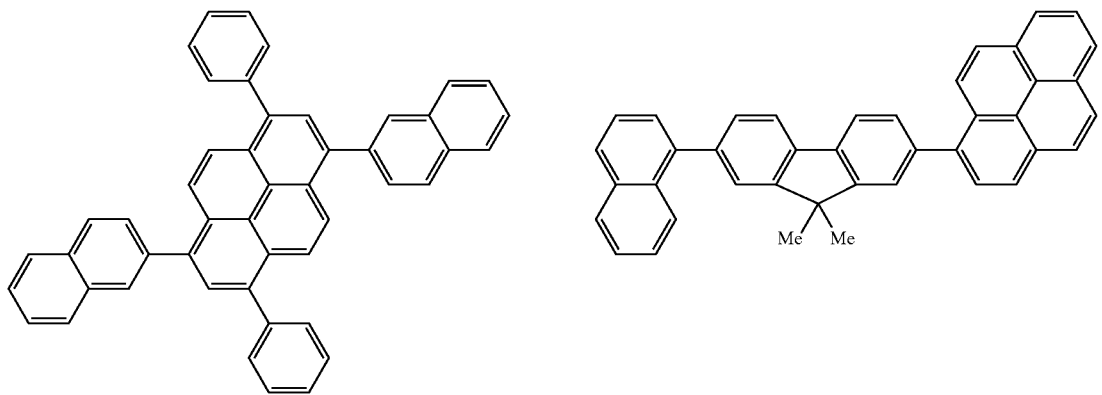
2b-28 2b-29
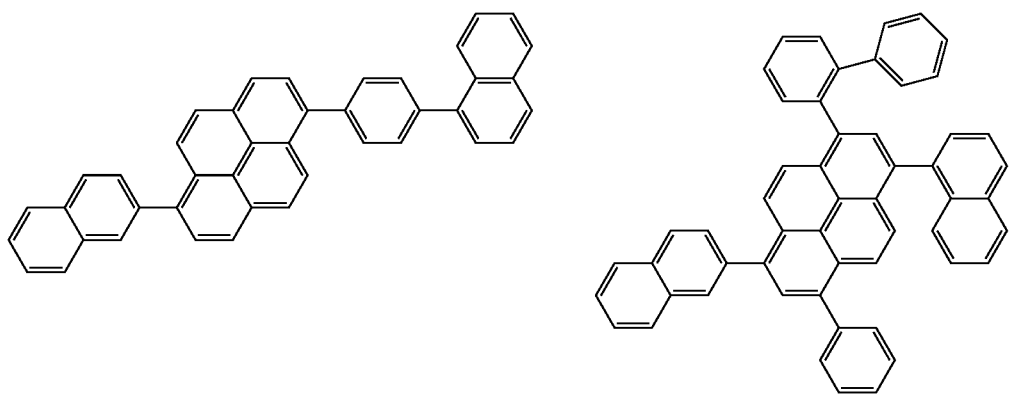

[Chemical Formula 34]
2b-30
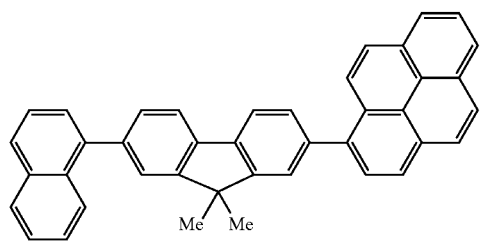
2b-31
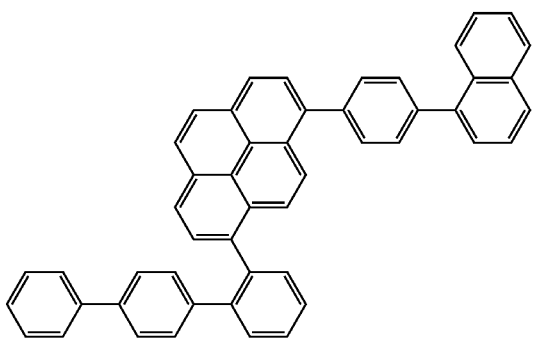
2b-32
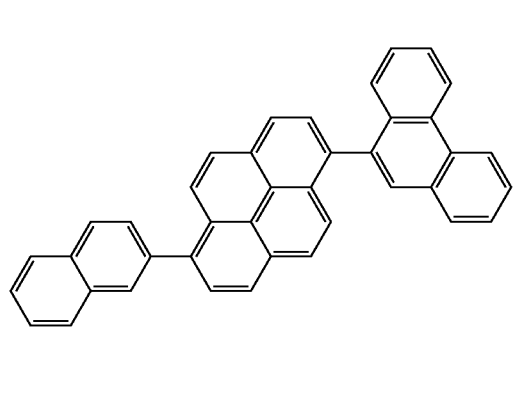
2b-33
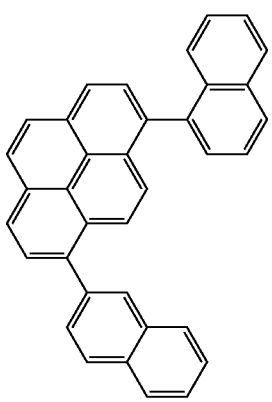
2b-34
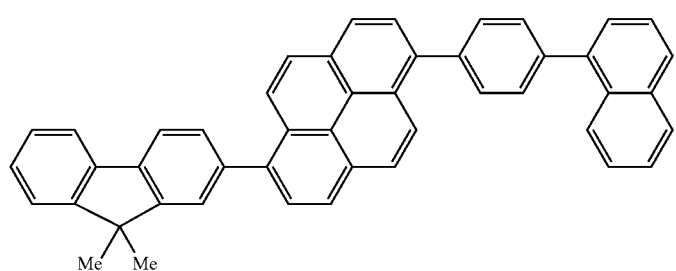
2b-35
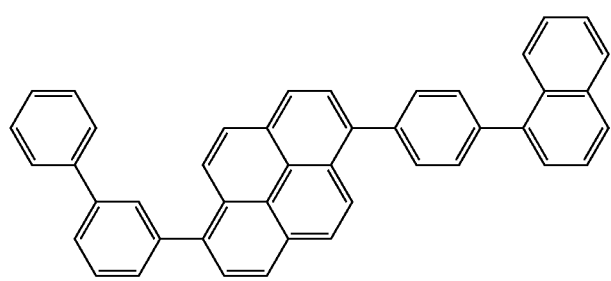

-continued
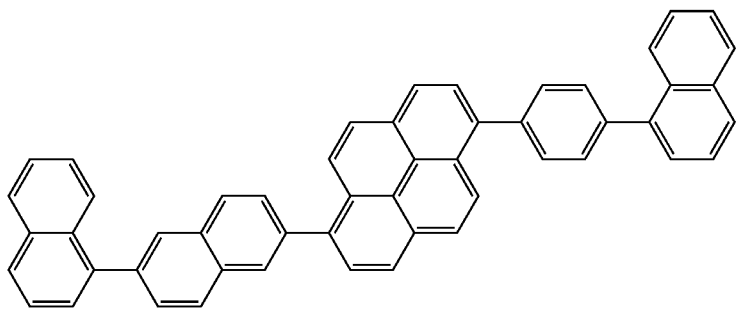
2b-36
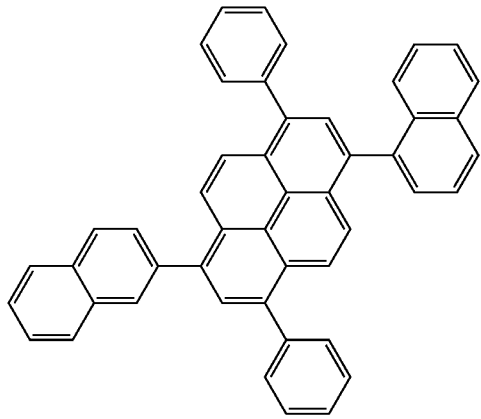
2b-37
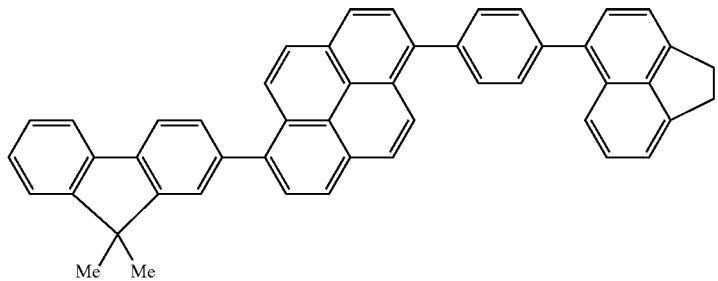
2b-38
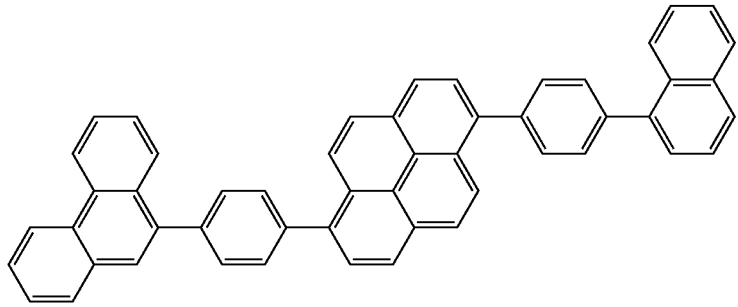
2b-39
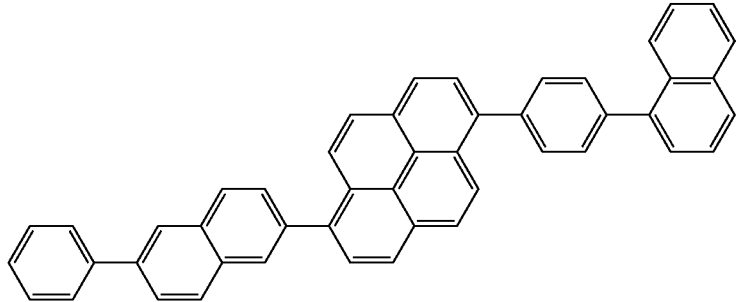
2b-40

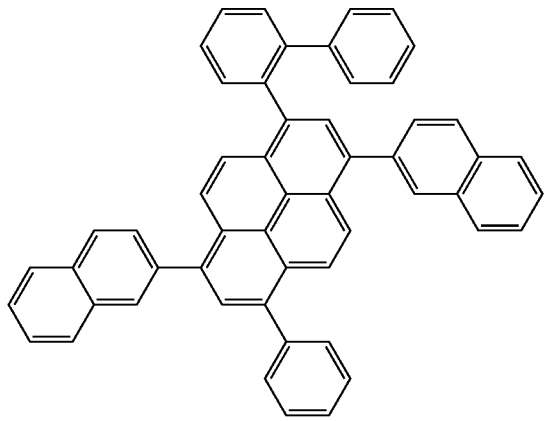

2b-41

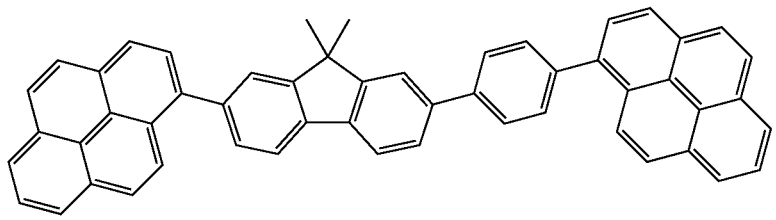

2b-42

When used as an emitting material, the diaminopyrene derivative according to the aspect of the invention is preferably used together with a compound having a triphenylamine skeleton represented by the formula (9).

In the formula (9), $Ar^{91}$, $Ar^{92}$ and $Ar^{93}$ are each independently selected from a group having an anthracene structure, a group having a phenanthrene structure and a group having a pyrene structure.

$R^{91}$, $R^{92}$ and $R^{93}$ each independently represent a hydrogen atom or a substituent.

$Ar^{91}$, $Ar^{92}$ and $Ar^{93}$ in the formula (9) are preferably selected from a substituted or unsubstituted anthrylphenyl group, anthryl group, phenanthrenyl group, perylenyl group and pyrenyl group, more preferably selected from a alkyl-substituted or unsubstituted anthrylphenyl group, phenanthrenyl group and pyrenyl group, particularly preferably selected from a pyrenyl group and phenanthryl group.

Examples of the substituents $R^{91}$, $R^{92}$ and $R^{93}$ are an alkyl group (preferably having 1 to 30 carbon atoms, more preferably 1 to 20 carbon atoms, particularly preferably 1 to 10 carbon atoms, such as methyl, ethyl, isopropyl, t-butyl, n-octyl, n-decyl group, n-hexadecyl, cyclopropyl, cyclopentyl and cyclohexyl), alkenyl group (preferably having 2 to 30 carbon atoms, more preferably 2 to 20 carbon atoms, particularly preferably 2 to 10 carbon atoms, such as vinyl, allyl, 2-butenyl and 3-pentenyl), alkynyl group (preferably having 2 to 30 carbon atoms, more preferably 2 to 20 carbon atoms, particularly preferably 2 to 10 carbon atoms, such as propargyl and 3-pentynyl), aryl group (preferably having 6 to 30 carbon atoms, more preferably 6 to 20 carbon atoms, particularly preferably 6 to 12 carbon atoms, such as phenyl, p-methylphenyl, naphthyl and anthranil), amino group (preferably having 0 to 30 carbon atoms, more preferably 0 to 20 carbon atoms, particularly preferably 0 to 10 carbon atoms, such as amino, methylamino, dimethylamino, diethylamino, dibenzylamino, diphenylamino and ditolylamino), alkoxy group (preferably having 1 to 30 carbon atoms, more preferably 1 to 20 carbon atoms, particularly preferably 1 to 10 carbon atoms, such as methoxy, ethoxy, butoxy and 2-ethylhexyloxy), aryloxy group (preferably having 6 to 30 carbon atoms, more preferably 6 to 20 carbon atoms, particularly preferably 6 to 12 carbon atoms, such as phenyloxy, 1-naphthyloxy and 2-naphthyloxy), heteroaryloxy group (preferably having 1 to 30 carbon atoms, more preferably 1 to 20 carbon atoms, particularly preferably 1 to 12 carbon atoms, such as pyridyloxy, pyradyloxy, pyrimidyloxy and quinolyloxy), acyl group (preferably having 1 to 30 carbon atoms, more preferably 1 to 20 carbon atoms, particularly preferably 1 to 12 carbon atoms, such as acetyl, benzoyl, formyl and pivaloyl), alkoxycarbonyl group (preferably having 2 to 30 carbon atoms, more preferably 2 to 20 carbon atoms, particularly preferably 2 to 12 carbon atoms, such as methoxycarbonyl and ethoxycarbonyl), aryloxycarbonyl group (preferably having 7 to 30 carbon atoms, more preferably 7 to 20 carbon atoms, particularly preferably 7 to 12 carbon atoms, such as phenyloxycarbonyl), acyloxy group (preferably having 2 to 30 carbon atoms, more preferably 2 to 20 carbon atoms, particularly preferably 2 to 10 carbon atoms, such as acetoxy and benzoyloxy), acylamino group (preferably having 2 to 30 carbon atoms, more preferably 2 to 20 carbon atoms, particularly preferably 2 to 10 carbon atoms, such as acetylamino and benzoylamino), alkoxycarbonylamino group (preferably having 2 to 30 carbon atoms, more preferably 2 to 20 carbon atoms, particularly preferably 2 to 12 carbon atoms, such as methoxycarbonylamino), aryloxycarbonylamino group (preferably having 7 to 30 carbon atoms, more preferably 7 to 20 carbon atoms, particularly preferably 7 to 12 carbon atoms, such as phenyloxycarbonylamino), sulphonylamino group (preferably having 1 to 30 carbon atoms, more preferably 1 to 20 carbon atoms, particularly preferably 1 to 12 carbon atoms, such as methanesulphonylamino and benzenesulphonylamino), sulphamoyl group (preferably having 0 to 30 carbon atoms, more preferably 0 to 20 carbon atoms, particularly preferably 0 to 12 carbon atoms, such as sulphamoyl, methylsulphamoyl, dimethylsulphamoyl and phenylsulphamoyl), carbamoyl group (preferably having 1 to 30 carbon atoms, more preferably 1 to 20 carbon atoms, particularly preferably 1 to 12 carbon atoms, such as carbamoyl, methylcarbamoyl, diethylcarbamoyl and phenylcarbamoyl), alkylthio group (preferably having 1 to 30 carbon atoms, more preferably 1 to 20 carbon atoms, particularly preferably 1 to 12 carbon atoms, such as methylthio and ethylthio), arylthio group (preferably having 6 to 30 carbon atoms, more preferably 6 to 20 carbon atoms, particularly preferably 6 to 12 carbon atoms, such as phenylthio), heteroarylthio group (preferably having 1 to 30 carbon atoms, more preferably 1 to 20 carbon atoms, particularly preferably 1 to 12 carbon atoms, such as pyridylthio, 2-benzimizolylthio, 2-benzoxazolylthio and 2-benzthiazolylthio), sulphonyl group (preferably having 1 to 30 carbon atoms, more preferably 1 to 20 carbon atoms, particularly preferably 1 to 12 carbon atoms, such as mesyl and tosyl), sulphinyl group (preferably having 1 to 30 carbon atoms, more preferably 1 to 20 carbon atoms, particularly preferably 1 to 12 carbon atoms, such as methanesulphinyl and benzenesulphinyl), ureido group (preferably having 1 to 30 carbon atoms, more preferably 1 to 20 carbon atoms, particularly preferably 1 to 12 carbon atoms, such as ureido, methylureido and phenylureido), phosphoramide group (preferably having 1 to 30 carbon atoms, more preferably 1 to 20 carbon atoms, particularly preferably 1 to 12 carbon atoms, such as diethyl-phosphoramide and phenyl-phosphoramide), hydroxy group, mercapto group, halogen atom (such as fluorine atom, chlorine atom, bromine atom and iodine atom), cyano group, sulfo group, carboxyl group, nitro group, hydroxamic group, sulfino group, hydrazine group, imino group, heterocyclic group (preferably having 1 to 30 carbon atoms, more preferably 1 to 12 carbon atoms, examples of heteroatom being nitrogen atom, oxygen atom and sulfur atom, such as imidazolyl, pyridyl, quinolyl, furyl, thienyl, piperidyl, morpholino, benzoxazolyl, benzimidazolyl and benzothiazolyl) and silyl group (preferably having 3 to 40 carbon atoms, more preferably 3 to 30 carbon atoms, particularly preferably 3 to 24 carbon atoms, such as trimethylsilyl and triphenylsilyl). These substituents may be further substituted.

The substituents $R^{91}$, $R^{92}$ and $R^{93}$ in the formula (9) are preferably selected from an alkyl group and aryl group.

Examples of the amine derivative represented by the formula (9) for use in the organic EL device according to the aspect of the invention are known various amine derivatives such as amine derivatives disclosed in paragraphs [0079] to [0083] of JP-A-2002-324678. Representative examples are shown below.

[Chemical Formula 35]

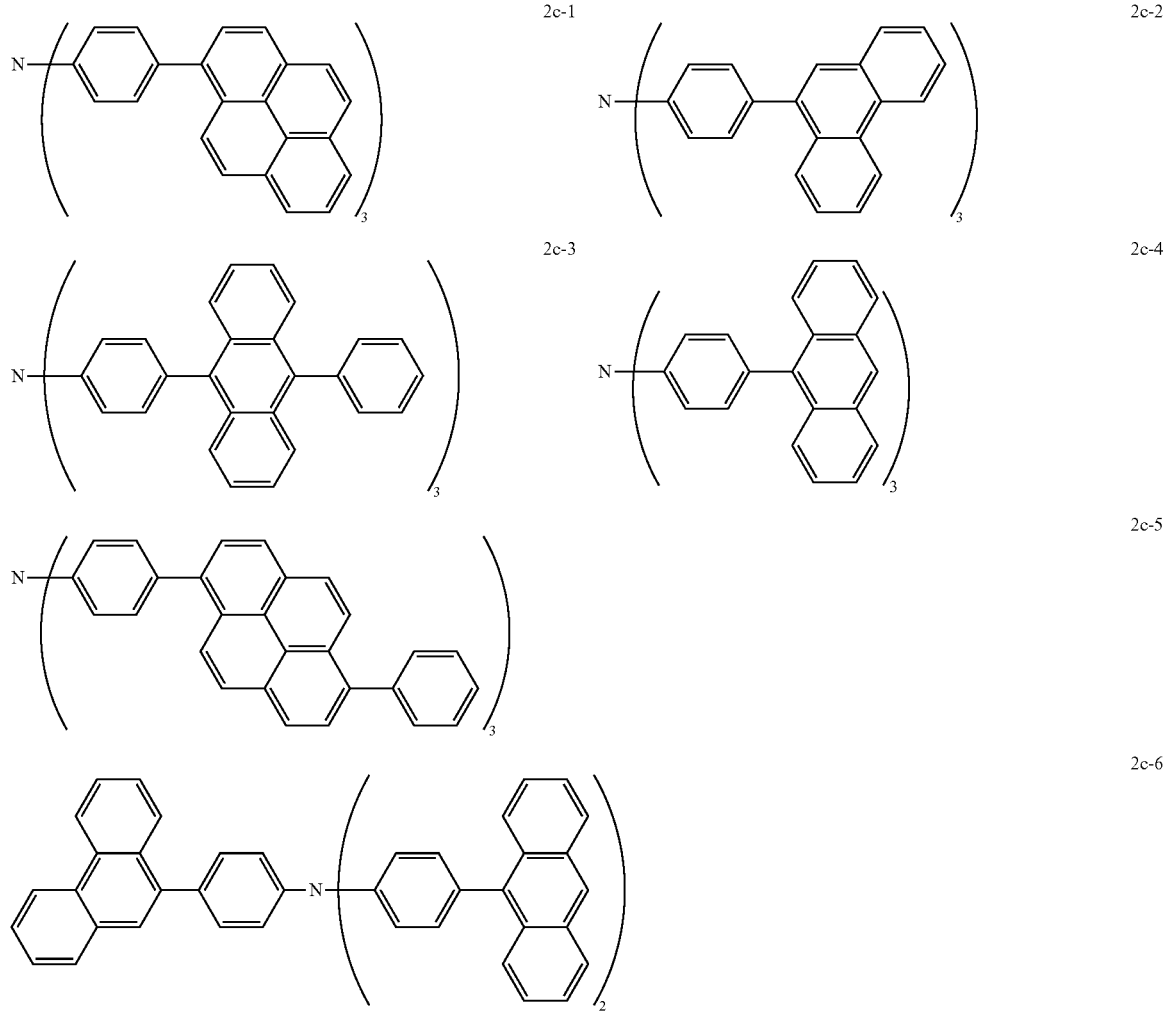

-continued
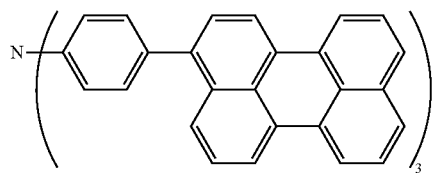
2c-8
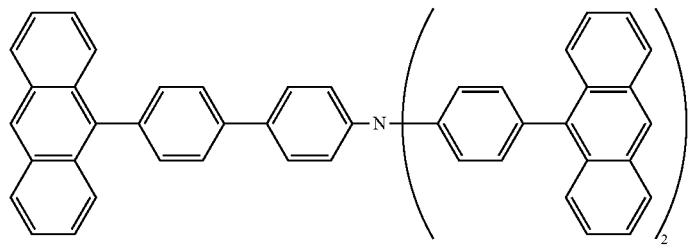
2c-10
[Chemical Formula 36]
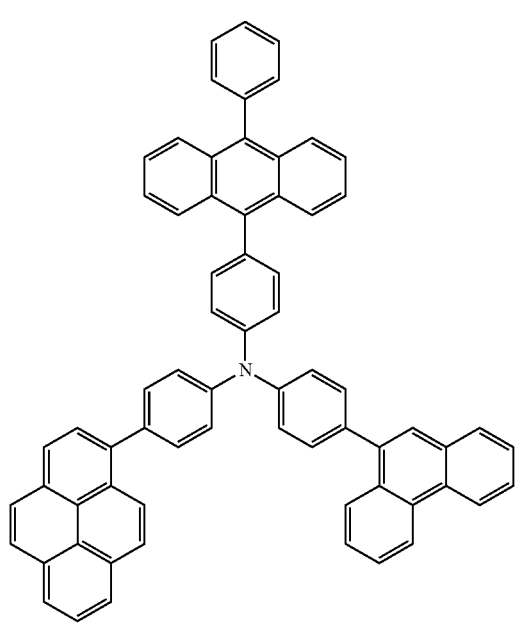
2c-11
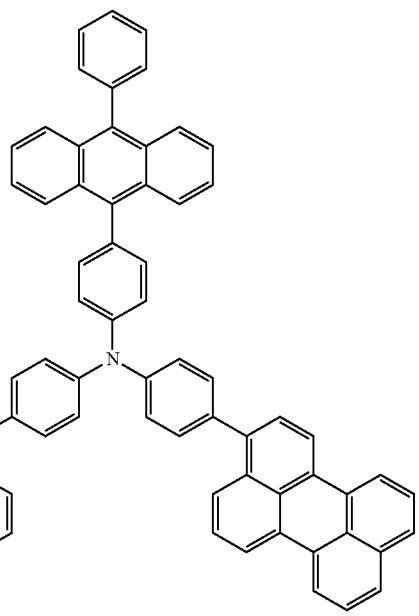
2c-12
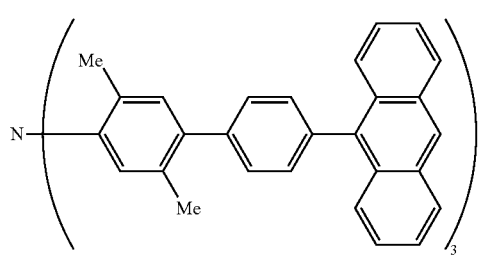
2c-13
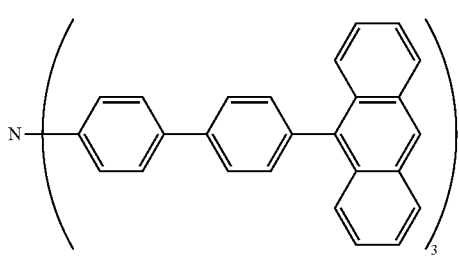
2c-15
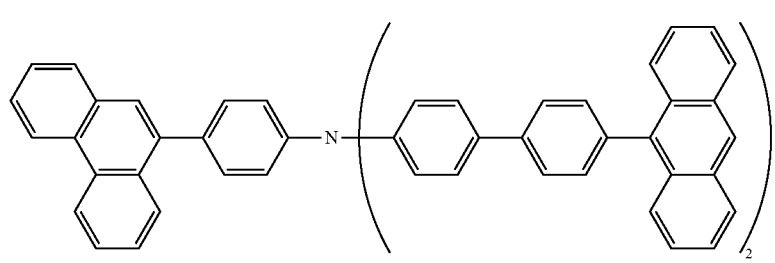
2c-17

When used as an emitting material, the diaminopyrene derivative according to the aspect of the invention is preferably used together with a compound represented by the formula (10).

In the formula (10), $Ar^{12}$, $Ar^{13}$ and $Ar^{14}$ each independently represent an aryl group having 6 to 50 carbon atoms for forming the ring. The aryl group may be substituted by 1 or more substituent(s).

At least one of $Ar^{12}$, $Ar^{13}$, $Ar^{14}$ and substituents for these aryl groups has a ring-fused aryl structure having 10 to 20 carbon atoms for forming the ring or a ring-fused heteroaryl structure having 6 to 20 carbon atoms for forming the ring.

$Ar^{11}$ represents a trivalent group induced from an aromatic ring or hetero aromatic ring.

The aryl group having 6 to 50 ring carbon atoms for $Ar^{12}$, $Ar^{13}$ and $Ar^{14}$ in the formula (10) preferably has 6 to 30 ring carbon atoms, more preferably 6 to 20 carbon atoms, much more preferably 6 to 16 carbon atoms. Examples of the aryl group are a phenyl group, naphthyl group, anthryl group, phenanthrenyl group, pyrenyl group, perylenyl group, fluorenyl group, biphenylyl group, terphenylyl group, rubrenyl group, chrysenyl group, triphenylenyl group, benzanthryl group, benzophenanthrenyl group and diphenylanthryl group. These aryl groups may be further substituted.

Examples of the substituent for the aryl group are an alkyl group (preferably having 1 to 30 carbon atoms, more preferably 1 to 20 carbon atoms, particularly preferably 1 to 10 carbon atoms, such as methyl, ethyl, isopropyl, t-butyl, n-octyl, n-decyl group, n-hexadecyl, cyclopropyl, cyclopentyl and cyclohexyl), alkenyl group (preferably having 2 to 30 carbon atoms, more preferably 2 to 20 carbon atoms, particularly preferably 2 to 10 carbon atoms, such as vinyl, allyl, 2-butenyl and 3-pentenyl), alkynyl group (preferably having 2 to 30 carbon atoms, more preferably 2 to 20 carbon atoms, particularly preferably 2 to 10 carbon atoms, such as propargyl and 3-pentynyl), aryl group (preferably having 6 to 30 carbon atoms, more preferably 6 to 20 carbon atoms, particularly preferably 6 to 12 carbon atoms, such as phenyl, p-methylphenyl, naphthyl and anthranil), amino group (preferably having 0 to 30 carbon atoms, more preferably 0 to 20 carbon atoms, particularly preferably 0 to 10 carbon atoms, such as amino, methylamino, dimethylamino, diethylamino, dibenzylamino, diphenylamino and ditolylamino), alkoxy group (preferably having 1 to 30 carbon atoms, more preferably 1 to 20 carbon atoms, particularly preferably 1 to 10 carbon atoms, such as methoxy, ethoxy, butoxy and 2-ethylhexyloxy), aryloxy group (preferably having 6 to 30 carbon atoms, more preferably 6 to 20 carbon atoms, particularly preferably 6 to 12 carbon atoms, such as phenyloxy, 1-naphthyloxy and 2-naphthyloxy), heteroaryloxy group (preferably having 1 to 30 carbon atoms, more preferably 1 to 20 carbon atoms, particularly preferably 1 to 12 carbon atoms, such as pyridyloxy, pyradyloxy, pyrimidyloxy and quinolyloxy), acyl group (preferably having 1 to 30 carbon atoms, more preferably 1 to 20 carbon atoms, particularly preferably 1 to 12 carbon atoms, such as acetyl, benzoyl, formyl and pivaloyl), alkoxycarbonyl group (preferably having 2 to 30 carbon atoms, more preferably 2 to 20 carbon atoms, particularly preferably 2 to 12 carbon atoms, such as methoxycarbonyl and ethoxycarbonyl), aryloxycarbonyl group (preferably having 7 to 30 carbon atoms, more preferably 7 to 20 carbon atoms, particularly preferably 7 to 12 carbon atoms, such as phenyloxycarbonyl), acyloxy group (preferably having 2 to 30 carbon atoms, more preferably 2 to 20 carbon atoms, particularly preferably 2 to 10 carbon atoms, such as acetoxy and benzoyloxy), acylamino group (preferably having 2 to 30 carbon atoms, more preferably 2 to 20 carbon atoms, particularly preferably 2 to 10 carbon atoms, such as acetylamino and benzoylamino), alkoxycarbonylamino group (preferably having 2 to 30 carbon atoms, more preferably 2 to 20 carbon atoms, particularly preferably 2 to 12 carbon atoms, such as methoxycarbonylamino), aryloxycarbonylamino group (preferably having 7 to 30 carbon atoms, more preferably 7 to 20 carbon atoms, particularly preferably 7 to 12 carbon atoms, such as phenyloxycarbonylamino), sulphonylamino group (preferably having 1 to 30 carbon atoms, more preferably 1 to 20 carbon atoms, particularly preferably 1 to 12 carbon atoms, such as methanesulphonylamino and benzenesulphonylamino), sulphamoyl group (preferably having 0 to 30 carbon atoms, more preferably 0 to 20 carbon atoms, particularly preferably 0 to 12 carbon atoms, such as sulphamoyl, methylsulphamoyl, dimethylsulphamoyl and phenylsulphamoyl), carbamoyl group (preferably having 1 to 30 carbon atoms, more preferably 1 to 20 carbon atoms, particularly preferably 1 to 12 carbon atoms, such as carbamoyl, methylcarbamoyl, diethylcarbamoyl and phenylcarbamoyl), alkylthio group (preferably having 1 to 30 carbon atoms, more preferably 1 to 20 carbon atoms, particularly preferably 1 to 12 carbon atoms, such as methylthio and ethylthio), arylthio group (preferably having 6 to 30 carbon atoms, more preferably 6 to 20 carbon atoms, particularly preferably 6 to 12 carbon atoms, such as phenylthio), heteroarylthio group (preferably having 1 to 30 carbon atoms, more preferably 1 to 20 carbon atoms, particularly preferably 1 to 12 carbon atoms, such as pyridylthio, 2-benzimizolylthio, 2-benzoxazolylthio and 2-benzthiazolylthio), sulphonyl group (preferably having 1 to 30 carbon atoms, more preferably 1 to 20 carbon atoms, particularly preferably 1 to 12 carbon atoms, such as mesyl and tosyl), sulphinyl group (preferably having 1 to 30 carbon atoms, more preferably 1 to 20 carbon atoms, particularly preferably 1 to 12 carbon atoms, such as methanesulphinyl and benzenesulphinyl), ureido group (preferably having 1 to 30 carbon atoms, more preferably 1 to 20 carbon atoms, particularly preferably 1 to 12 carbon atoms, such as ureido, methylureido and phenylureido), phosphoramide group (preferably having 1 to 30 carbon atoms, more preferably 1 to 20 carbon atoms, particularly preferably 1 to 12 carbon atoms, such as diethyl-phosphoramide and phenyl-phosphoramide), hydroxy group, mercapto group, halogen atom (such as fluorine atom, chlorine atom, bromine atom and iodine atom), cyano group, sulfo group, carboxyl group, nitro group, hydroxamic group, sulfino group, hydrazine group, imino group, heterocyclic group (preferably having 1 to 30 carbon atoms, more preferably 1 to 12 carbon atoms, examples of heteroatom being nitrogen atom, oxygen atom and sulfur atom, such as imidazolyl, pyridyl, quinolyl, furyl, thienyl, piperidyl, morpholino, benzoxazolyl, benzimidazolyl, benzothiazolyl, carbazolyl group and azepinyl group) and silyl group (preferably having 3 to 40 carbon atoms, more preferably 3 to 30 carbon atoms, particularly preferably 3 to 24 carbon atoms, such as trimethylsilyl and triphenylsilyl). These substituents may be further substituted.

Examples of the ring-fused aryl structure having 10 to 20 ring carbon atoms, which is present in at least one of $Ar^{12}$, $Ar^{13}$, $Ar^{14}$ and the substituents for these aryl groups in the formula (10), are a naphthalene structure, anthracene structure, phenanthrene structure, pyrene structure and perylene structure, preferably a naphthalene structure, anthracene structure, pyrene structure and phenanthrene structure, more preferably phenanthrene structure and aryl structure having four or more rings, particularly preferably a pyrene structure.

Examples of the ring-fused heteroaryl structure having 6 to 20 ring carbon atoms, which is present in at least one of $Ar^{12}$, $Ar^{13}$, $Ar^{14}$ and the substituents for these aryl groups in the formula (10), are a quinoline structure, quinoxaline structure, quinazoline structure, acridine structure, phenanthridine structure, phthalazine structure and phenanthroline structure, preferably a quinoline structure, quinoxaline structure, quinazoline structure, phthalazine structure and phenanthroline structure.

The trivalent group induced from the aromatic ring of $Ar^{11}$ in the formula (10) preferably has 6 to 30 carbon atoms, more preferably 6 to 20 carbon atoms, much more preferably 6 to 16 carbon atoms. Examples are trivalent groups induced from benzene, naphthalene, anthracene, phenanthrene, pyrene and triphenylene.

The trivalent group induced from the hetero aromatic ring of $Ar^{11}$ in the formula (10) preferably has as the heteroatom an atom selected from nitrogen atom, sulfur atom and oxygen atom. The heteroatom is more preferably a nitrogen atom. In addition, the number of carbon atoms are preferably 2 to 30, more preferably 3 to 20, much more preferably 3 to 16. Examples are trivalent groups induced from pyridine, pyrazine, thiopyran, quinoline, quinoxaline and triazine. The trivalent group induced from the aromatic ring or hetero aromatic ring may be substituted. Examples of the substituent are groups exemplified in relation to the substituent for the aryl group of $Ar^{12}$, $Ar^{13}$ and $Ar^{14}$. $Ar^{11}$ is preferably a trivalent group induced from benzenetriyl, naphthalenetriyl, anthracenetriyl, pyrenetriyl and triphenylene, more preferably benzenetriyl, much more preferably benzentriyl in which only $Ar^{12}$, $Ar^{13}$ and $Ar^{14}$ are substituted and alkyl-substituted benzenetriyl.

Examples of the benzene derivative represented by the formula (10) for use in the organic EL device according to the aspect of the invention are known various benzene derivatives such as benzene derivatives disclosed in paragraphs [0079] to of JP-A-2002-324678. Representative examples are shown below.

[Chemical Formula 37]

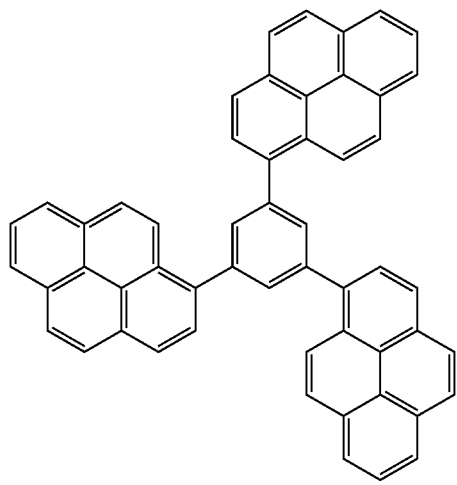

2d-1

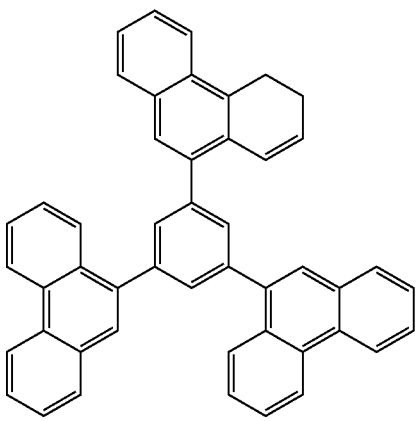

2d-2

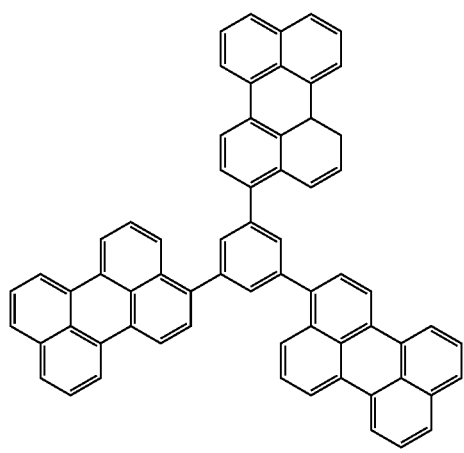

2d-3

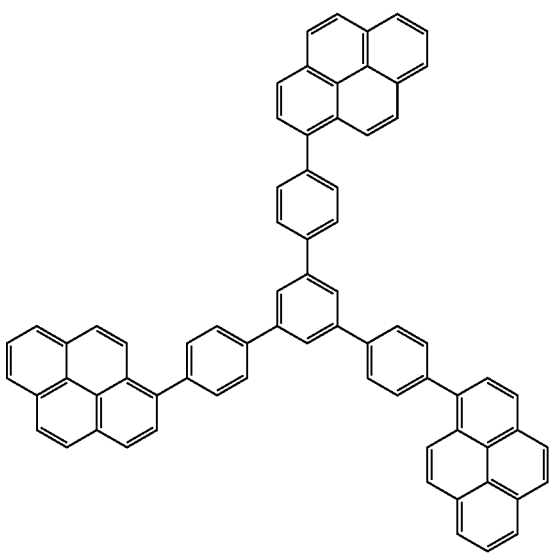

2d-4

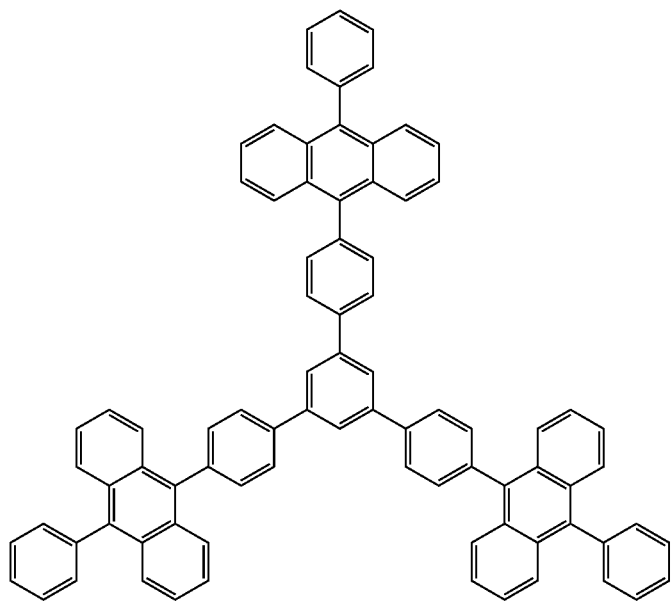
2d-5
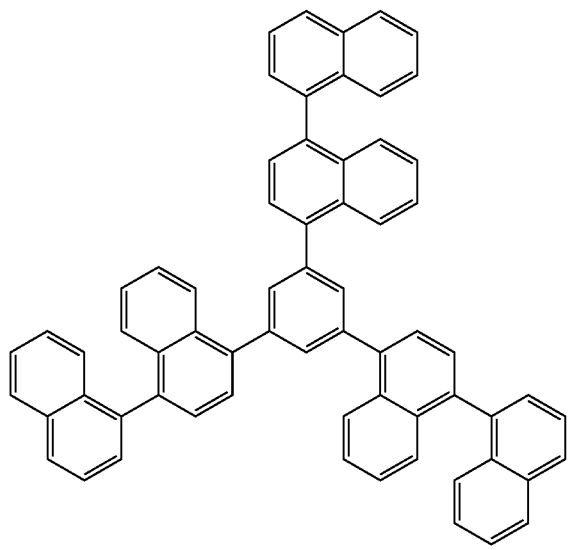
2d-6

[Chemical Formula 38]
2d-7
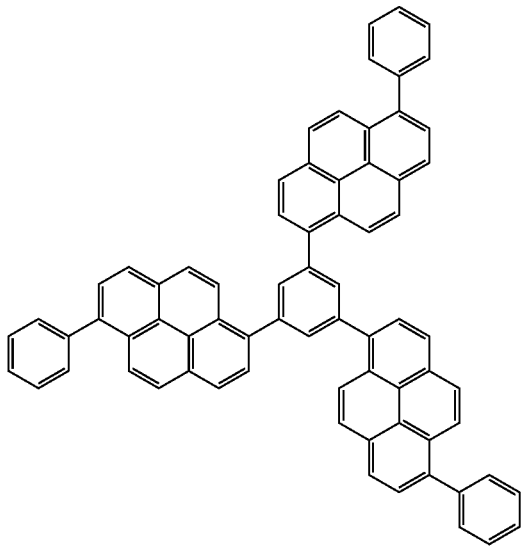
2d-8
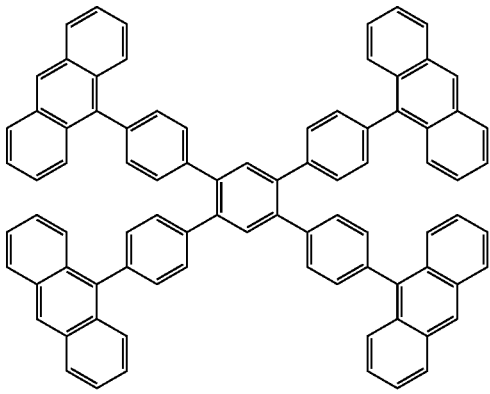
2d-9
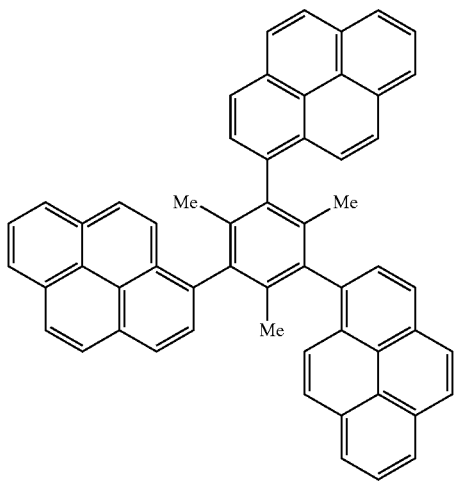
2d-10
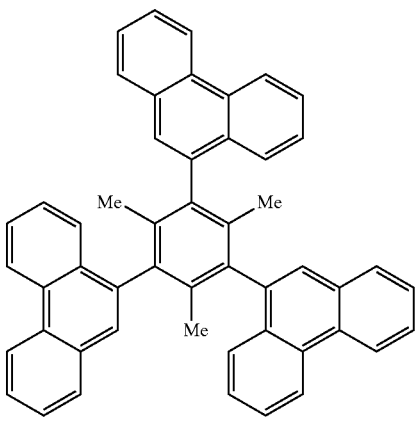
2d-10
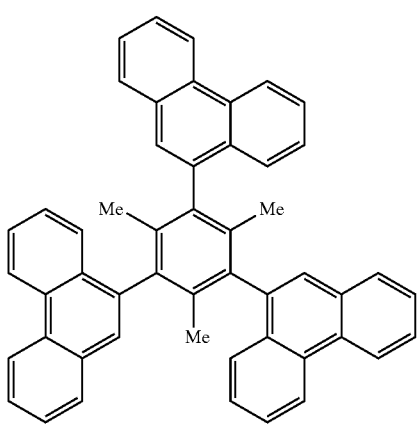

-continued
2d-11
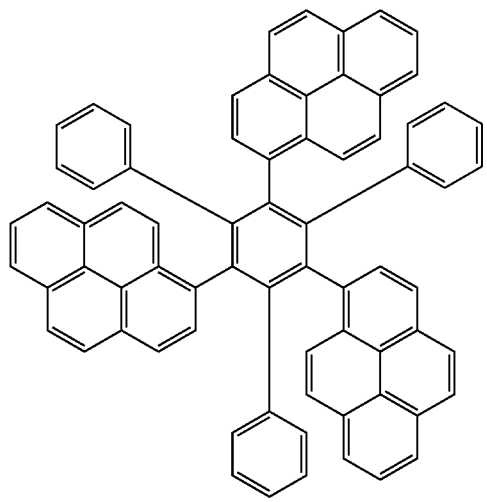
2d-12
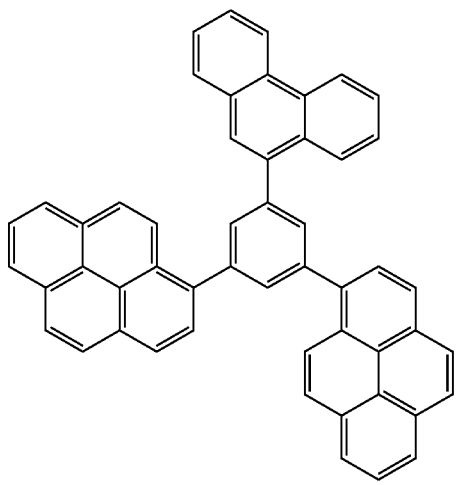
[Chemical Formula 39]
2d-13
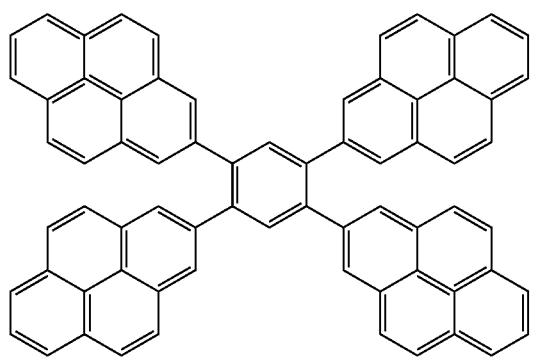
2d-14
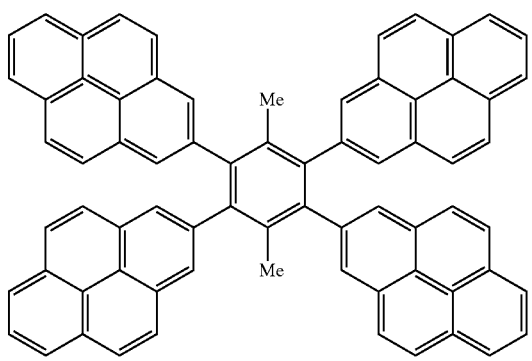
2d-15
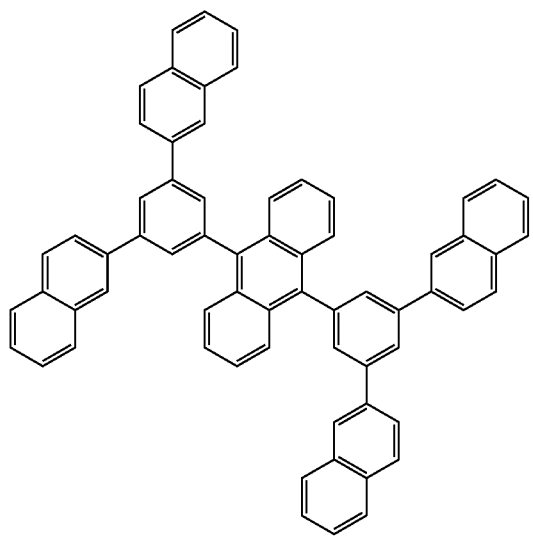
2d-16
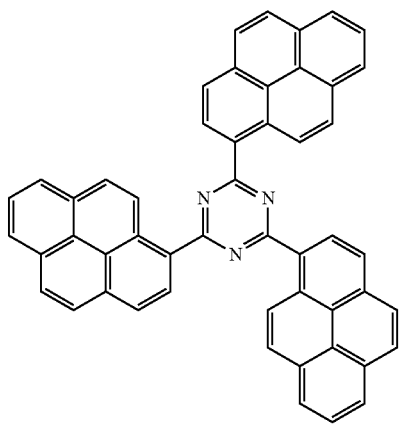

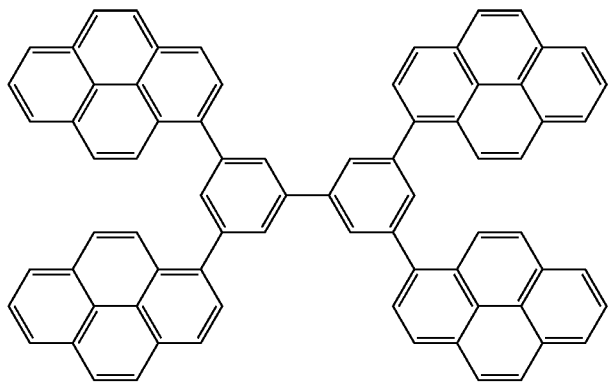

2d-17

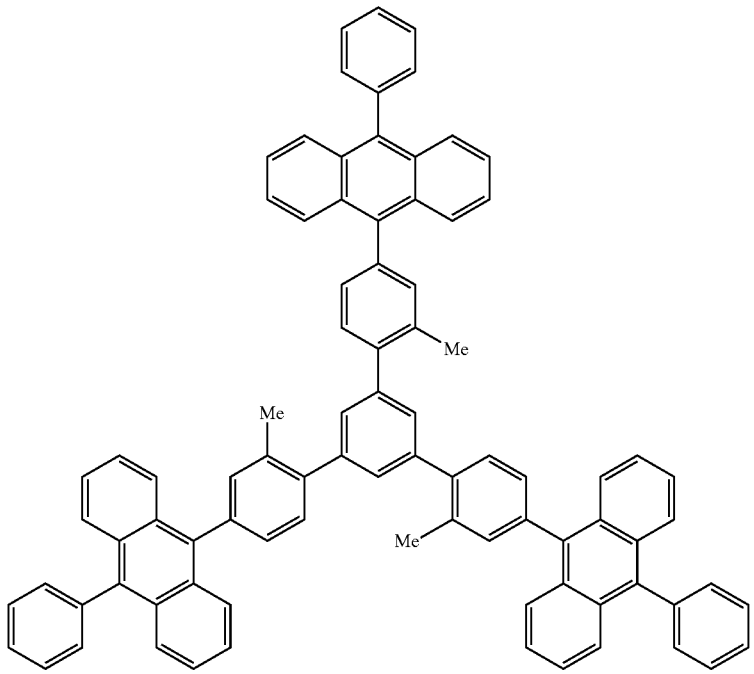

2d-18

In the organic EL device according to the aspect of the invention, the emitting layer preferably contains the diaminopyrene derivative according to the aspect of the invention at 0.01 to 20 mass %, more preferably at 0.5 to 20 mass %. The content of the diaminopyrene derivative is further preferably 1 mass % to 20 mass %, much more preferably 5 mass % to 20 mass %.

Preferably in the organic EL device according to the aspect of the invention, a surface of at least one of the pair of electrodes is layered with a layer selected from a chalcogenide layer, halogenated metal layer and metal oxide layer.

EXAMPLES

Next, the invention will be described in further detail by exemplifying Example(s) and Comparative(s). However, the invention is not limited by the description of Example(s).

Synthesis Example 1

Synthesis of Compound (d-15)

Under argon stream, 4.4 g (10 mmol) of 3,8-diisopropyl-1,6-dibromopyrene, 7.8 g (25 mmol) of bis(4-trimethylsilylphenyl)amine, 0.033 g (0.15 mmol) of palladium acetate, 0.061 g (0.3 mmol) of tri-t-butylphosphine, 2.4 g (25 mmol) of sodium t-butoxide and 100 mL of dry toluene were put into a three-neck flask of 300 mL having a cooling pipe, and stirred at 100 degrees C. for a night while heated. On completion of the reaction, the precipitated crystal were separated by filtration and cleaned with 50 mL of toluene and 100 mL of methanol. Then, 8.2 g of light yellow powder was obtained. This powder was identified as the compound (d-15) as a result of measurement of $^1$H-NMR spectrum and FD-MS (field desorption mass spectrum). The yield was 80%. $^1$H-NMR spectrum was measured with DRX-500 manufactured by Brucker Corporation (solvent of perchloromethylene).

Figure 2:
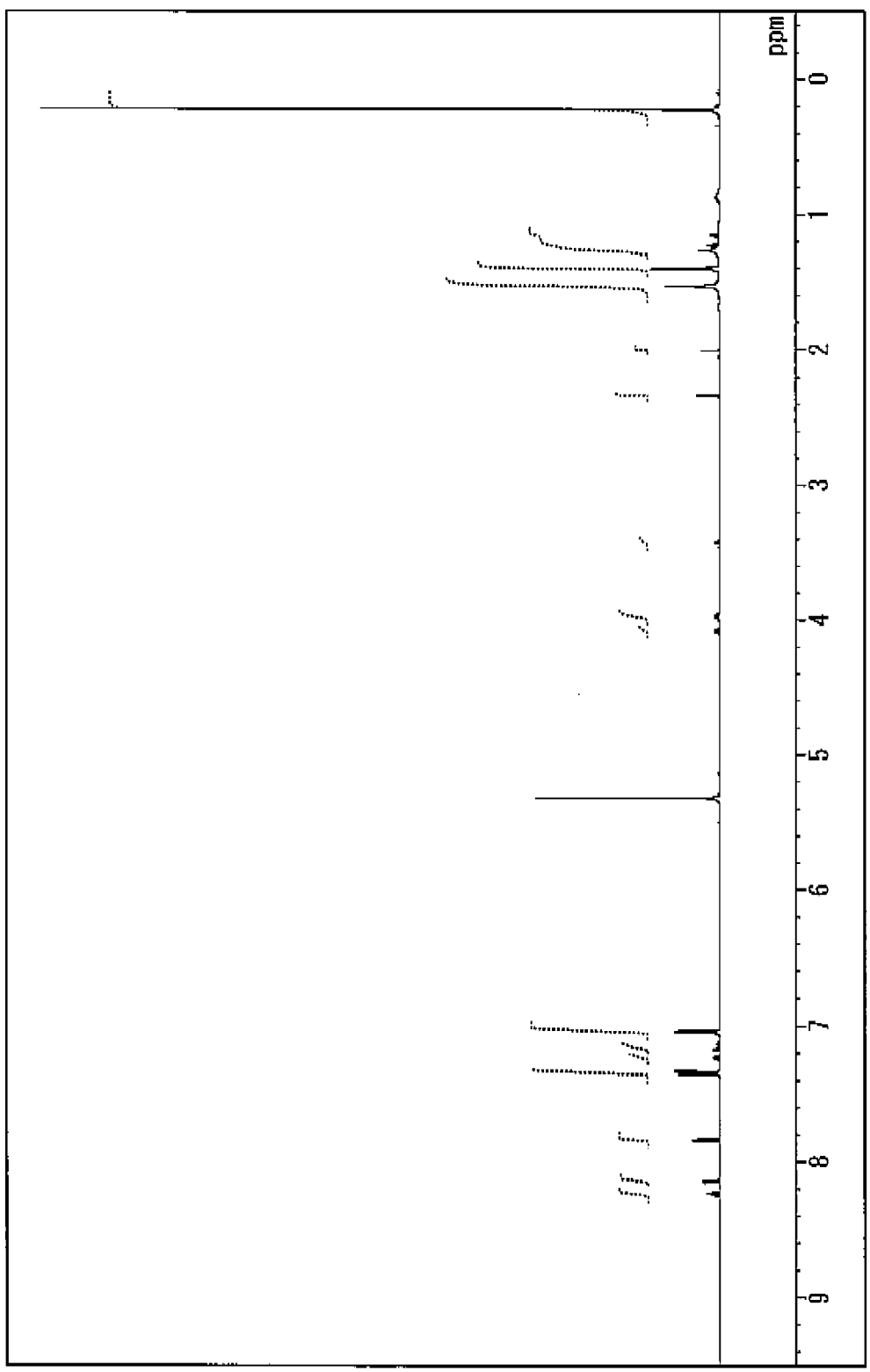
FIG. 2 shows a $^1$H-NMR spectrum of a diaminopyrene derivative according an example of the invention.
Figure 3A:
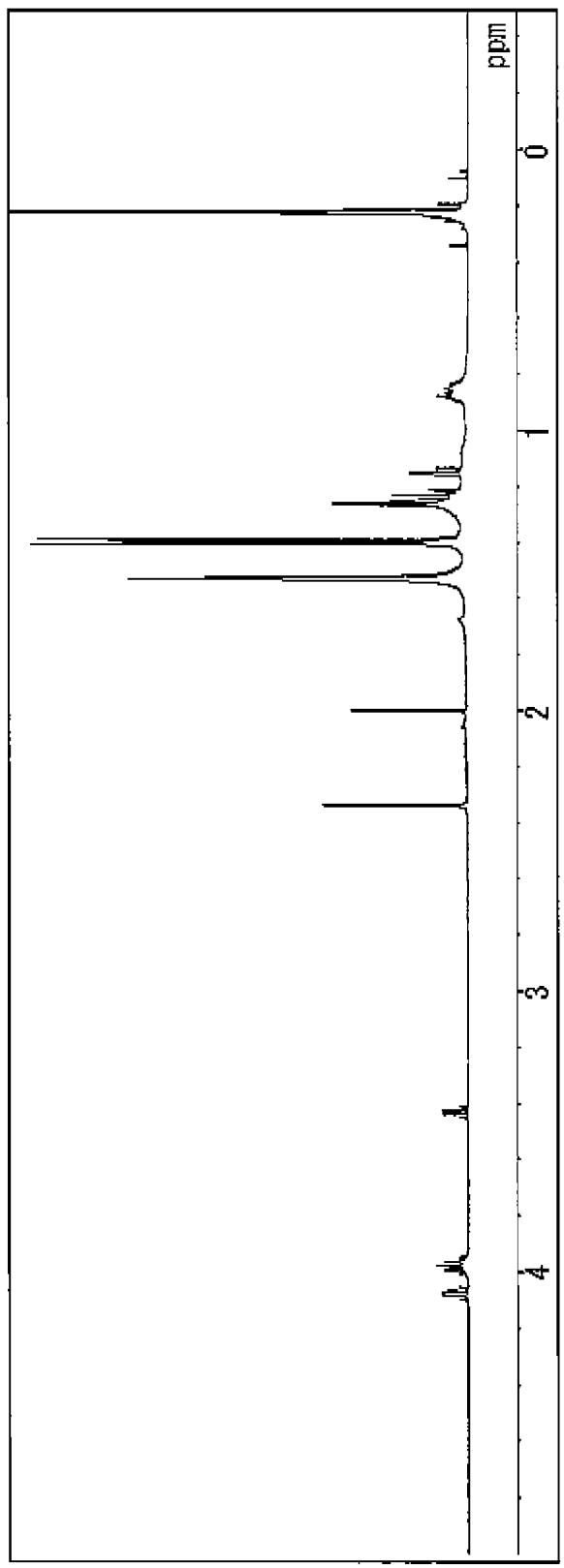
FIG. 3A is a magnified view of FIG. 2.
Figure 3B:
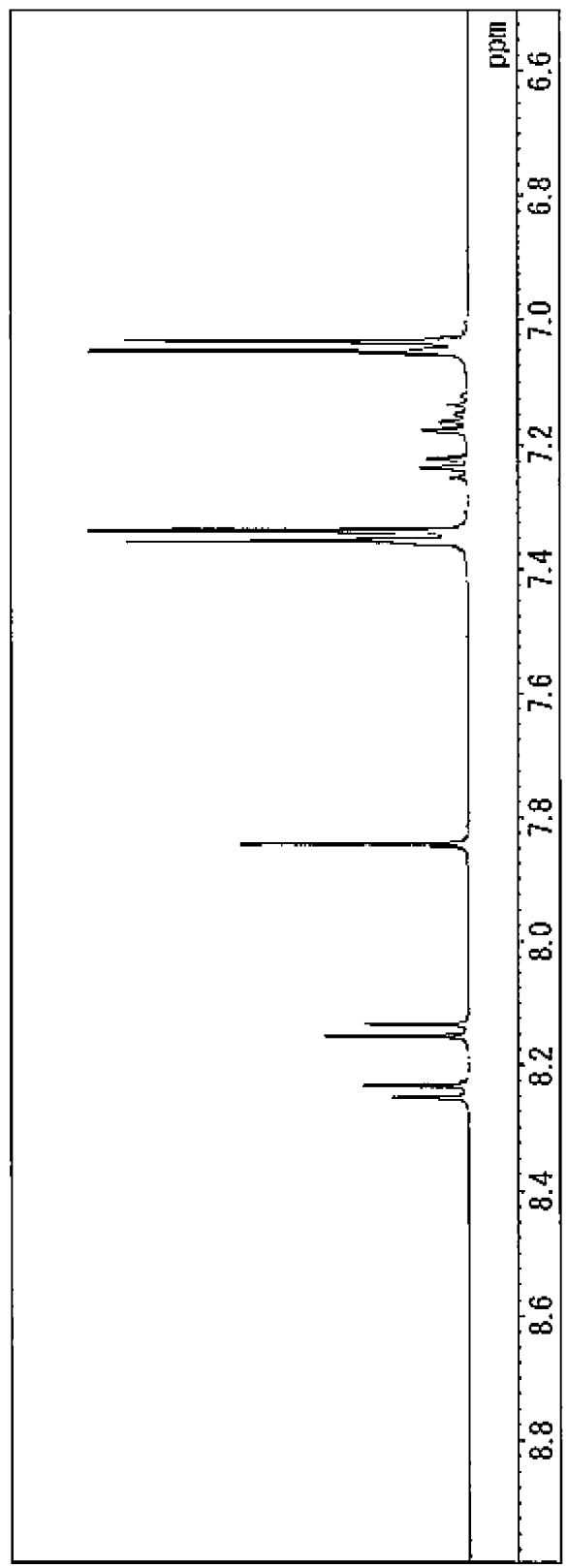
FIG. 3B is a magnified view of FIG. 2.

FIG. 2 shows the measured $^1$H-NMR spectrum, and FIGS. 3A and 3B are magnified views of FIG. 2. FIG. 3A magnifies the range of 5 to 0.5 ppm while FIG. 3B magnifies the range of 9 to 6.5 ppm.

Table 1 shows peak positions read from FIGS. 2, 3A and 3B.

TABLE 1

| Peak No. | Peak Position (ppm) |
|---|---|
| 1 | 0.10302 |
| 2 | 0.19363 |

TABLE 1-continued

| Peak No. | Peak Position (ppm) |
|---|---|
| 3 | 0.21680 |
| 4 | 0.22357 |
| 5 | 0.23003 |
| 6 | 0.24185 |
| 7 | 0.25367 |
| 8 | 0.34098 |
| 9 | 0.85377 |
| 10 | 0.87883 |
| 11 | 1.13712 |
| 12 | 1.15130 |
| 13 | 1.16533 |
| 14 | 1.21591 |
| 15 | 1.23025 |
| 16 | 1.24459 |
| 17 | 1.26161 |
| 18 | 1.39273 |
| 19 | 1.40628 |
| 20 | 1.52967 |
| 21 | 2.00244 |
| 22 | 2.33826 |
| 23 | 3.41128 |
| 24 | 3.42515 |
| 25 | 3.43918 |
| 26 | 3.96316 |
| 27 | 3.97687 |
| 28 | 3.99058 |
| 29 | 4.05629 |
| 30 | 4.07064 |
| 31 | 4.08482 |
| 32 | 4.09900 |
| 33 | 7.03315 |
| 34 | 7.04639 |
| 35 | 7.05017 |
| 36 | 7.13637 |

Synthesis Example 2

Synthesis of Compound (d-8)

Under argon stream, 3.8 g (10 mmol) of 3,8-dimethyl-1,6-dibromopyrene, 6 g (25 mmol) of 4-trimethylsilyl diphenylamine, 0.033 g (0.15 mmol) of palladium acetate, 0.061 g (0.3 mmol) of tri-t-butylphosphine, 2.4 g (25 mmol) of sodium t-butoxide and 100 mL of dry toluene were put into a three-neck flask of 300 mL having a cooling pipe, and stirred at 100 degrees C. for a night while heated. On completion of the reaction, the precipitated crystal were separated by filtration and cleaned with 50 mL of toluene and 100 mL of methanol. Then, 5.6 g of light yellow powder was obtained. This powder was identified as the compound (d-8) as a result of measurement of $^1$H-NMR spectrum and FD-MS. The yield was 80%. The maximum absorption wavelength measured in a solution of toluene with respect to the obtained compound was 425 nm.

Figure 4:
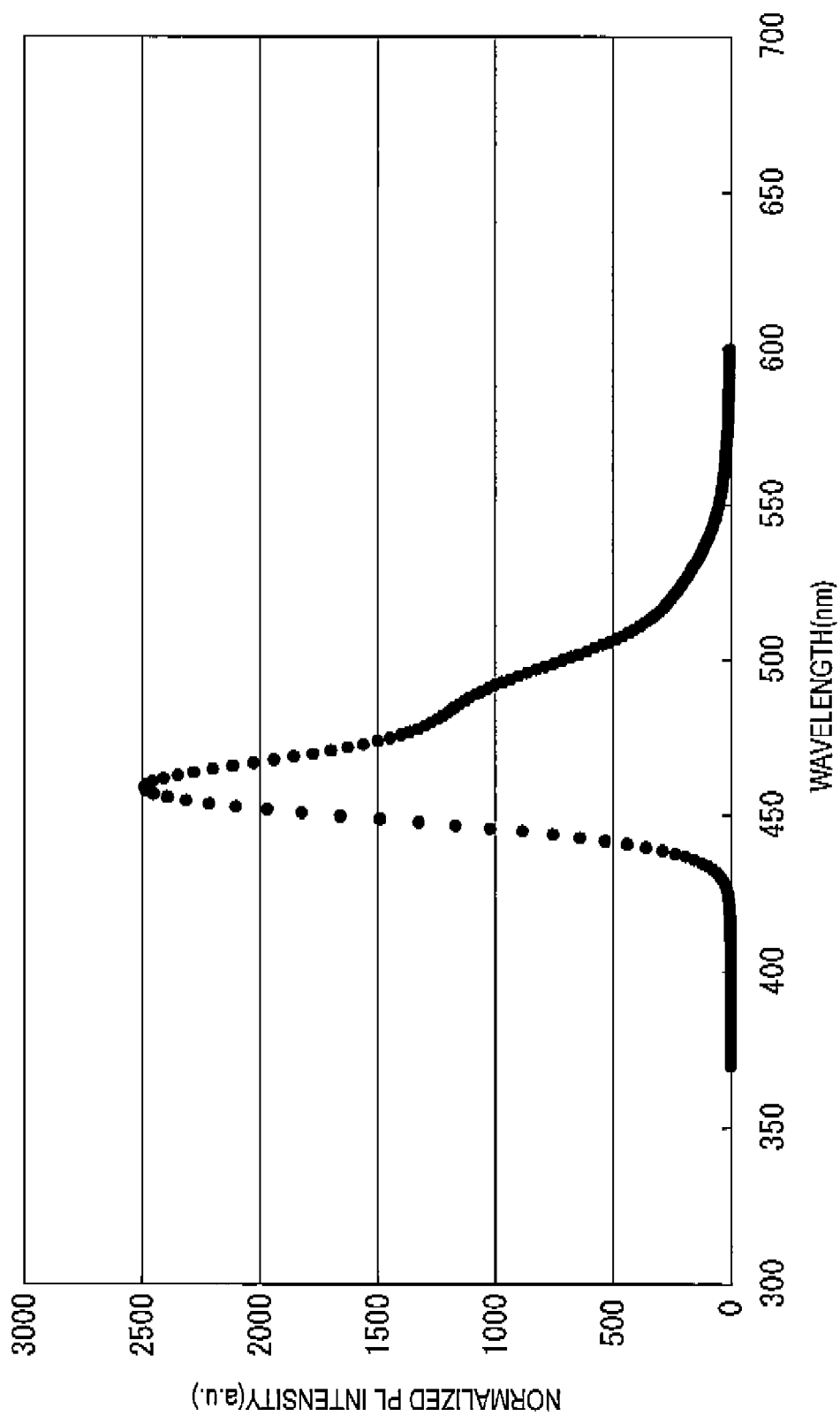
FIG. 4 shows a fluorescence spectrum of a diaminopyrene derivative according an example of the invention.

FIG. 4 shows the emission spectrum of the obtained compound. The maximum fluorescence wavelength was 459 nm.

Example 1

A transparent electrode made of indium tin oxide was provided onto a glass substrate (size: 25 mm×75 mm×1.1 mm) to be 120 nm thick. The transparent electrode served as the anode.

Subsequently, the glass substrate was cleaned with irradiation of ultraviolet and ozone, and mounted on a vacuum deposition equipment.

N',N'''-bis[4-(diphenylamino)phenyl]-N',N'''-diphenylbiphenyl-4,4'-diamine was initially deposited to be 60 nm thick (serving as the hole injecting layer), and then N,N,N',N'-tetrakis(4-biphenyl)-4,4'-benzidine was deposited to be 20 nm thick (serving as the hole transporting layer). Subsequently, 10,10'-bis[1,1',4',1"]terphenyl-2-yl-9,9'-bisanthracene as the host and the compound (d-15) as the doping material were simultaneously deposited at a mass ratio of 40 to 2, so that a 40-nm thick emitting layer was provided.

As the electron injecting layer, tris(8-hydroxyquinolinato) aluminum was deposited on the emitting layer to be 20 nm thick.

Next, lithium fluoride was deposited to be 1 nm thick, and aluminum was then deposited to be 150 nm thick. This aluminum/lithium fluoride served as the cathode.

When a current test was conducted on the obtained organic EL device, blue emission (maximum wavelength of emission: 462 nm) was obtained with luminous efficiency of 7.0 cd/A and 700 cd/cm$^2$ under a voltage of 6.5 V and a current density of 10 mA/cm$^2$. When a direct-current continuous current test was conducted with the initial luminance intensity being 100 cd/cm$^2$, time elapsed until the initial luminance intensity was reduced to the half (i.e., time until half-life) was 10,000 hours and more.

Example 2

An organic EL device was manufactured by using the compound (d-28) in place of the compound (d-15) in Example 1.

When a current test was conducted on the obtained organic EL device, blue emission (maximum wavelength of emission: 461 nm) was obtained with luminous efficiency of 7.2 cd/A and 720 cd/cm$^2$ under a voltage of 6.5 V and a current density of 10 mA/cm$^2$. When a direct-current continuous current test was conducted with the initial luminance intensity being 100 cd/cm$^2$, time until half-life was 10,000 hours and more.

Example 3

An organic EL device was manufactured by using the compound (d-9) in place of the compound (d-15) in Example 1.

When a current test was conducted on the obtained organic EL device, blue emission (maximum wavelength of emission: 455 nm) was obtained with luminous efficiency of 5.4 cd/A and 540 cd/cm$^2$ under a voltage of 6.5 V and a current density of 10 mA/cm$^2$. When a direct-current continuous current test was conducted with the initial luminance intensity being 100 cd/cm$^2$, time until half-life was 7,000 hours.

Example 4

An organic EL device was manufactured in the same manner as Example 1, except that the host was changed to 9,10-bis[1,1',4',1"]terphenyl anthracene and the compound (d-8) was used as the dopant in place of the compound (d-15) in the emitting layer.

When a current test was conducted on the obtained organic EL device, blue emission (maximum wavelength of emission: 459 nm) was obtained with luminous efficiency of 6.6 cd/A and 660 cd/cm$^2$ under a voltage of 6.5 V and a current density of 10 mA/cm$^2$. When a direct-current continuous current test was conducted with the initial luminance intensity being 100 cd/cm$^2$, time until half-life was 8,500 hours.

Example 5

An organic EL device was manufactured in the same manner as Example 4, except that the mass ratio of host to dopant in the emitting layer was set at 40:3.

Example 6

An organic EL device was manufactured in the same manner as Example 4, except that the mass ratio of host to dopant in the emitting layer was set at 40:4.

Evaluation conducted in the same manner as Example 4 on the organic EL devices according to Examples 5 and 6 revealed that both of the organic EL devices according to Examples 5 and 6 emitted blue light and that the luminance intensity of Example 5 was 675 cd/m$^2$ while that of Example 6 was 680 cd/m$^2$.

The time until half-life of Example 5 was 9,500 hours while that of Example 6 was 10,000 and more.

From the above, the organic EL devices in which the aromatic amine derivative according to the aspect of the invention was doped in their emitting layers at a high concentration have been found to emit blue light of long life and high efficiency.

Example 7

An organic EL device was manufactured in the same manner as Example 1, except that the host was changed to 10-(4-naphthalene-1-yl)phenyl-9-(naphthalene-2-yl) anthracene and the compound (d-8) was used as the dopant in the emitting layer.

A current test was conducted on the obtained organic EL device.

Voltage was 6.5 V, and current density was 10 mA/cm$^2$;
Luminous efficiency was 6.7 cd/A and 670 cd/m$^2$;
Wavelength of emission was 467 nm;
Initial luminance intensity for a measurement of lifetime was 1000 cd/m$^2$ (direct current); and
Lifetime was 10,000 hr.

Example 8

An organic EL device was manufactured in the same manner as Example 7, except that the compound (d-14) was used as the dopant in the emitting layer.

A current test was conducted on the obtained organic EL device.

Voltage was 6.5 V, and current density was 10 mA/cm$^2$;
Luminous efficiency was 6.7 cd/A and 670 cd/m$^2$;
Wavelength of emission was 467 nm;
Initial luminance intensity for a measurement of lifetime was 1000 cd/m$^2$ (direct current); and
Lifetime was 10,000 hr.

Example 9

An organic EL device was manufactured in the same manner as Example 7, except that the compound (d-56) was used as the dopant in the emitting layer.

A current test was conducted on the obtained organic EL device.

Voltage was 6.5 V, and current density was 10 mA/cm$^2$;
Luminous efficiency was 17 cd/A and 17000 cd/m$^2$;
Wavelength of emission was 490 nm;
Initial luminance intensity for a measurement of lifetime was 1000 cd/m$^2$ (direct current);
Lifetime was 20,000 hr.

(Comparative 1)

An organic EL device was manufactured by using 1,6-bis[di(3-pyridyl)amino]pyrene in place of the compound (d-15) in Example 1.

When a current test was conducted on the obtained organic EL device, blue emission (maximum wavelength of emission: 451 nm) was obtained with luminous efficiency of 5.1 cd/A and 511 cd/cm$^2$ under a voltage of 6.2 V and a current density of 10 mA/cm$^2$. When a direct-current continuous current test was conducted with the initial luminance intensity being 100 cd/cm$^2$, time until half-life was as short as 1000 hours.

(Comparative 2)

An organic EL device was manufactured in the same manner as Example 4, except that 3,8-dimethyl-1,6-bis(diphenylamino) pyrene was used in place of the compound (d-8) and the mass ratio of host to dopant in the emitting layer was set at 40:2.

(Comparative 3)

An organic EL device was manufactured in the same manner as Example 4, except that 3,8-dimethyl-1,6-bis(diphenylamino) pyrene was used in place of the compound (d-8) and the mass ratio of host to dopant in the emitting layer was set at 40:4.

When a current test was conducted on these organic EL devices, the organic EL devices according to Comparatives 2 and 3 emitted blue light.

The time until half-life of the organic EL device according to Comparative 2 was 4,500 hours while that of the organic EL device according to Comparative 3 was 4,000 hours. Increase in the doping concentration did not lead to increase in lifetime.

The emission spectrum of Comparatives 2 and 3 was a broad spectrum peaked at a point closer to long-wavelength side than the desirable spectrum (e.g., FIG. 4), and the chromaticity was also deteriorated while exhibiting inconsistency with pure blue.

Although the reason of such deterioration is not necessarily clear, one possibility is that molecular aggregate resulted in emission of long-wavelength light.

From the above, diaminopyrene derivatives in which the diphenylamino groups were not substituted have been found not capable of increasing the lifetime by high-concentration doping. It has been also found that the high-concentration doping resulted in emission mixed with long-wavelength emission and thus deteriorated the chromaticity.

(Comparative 4)

An organic EL device was manufactured by using 1,6-bis ((4-trimethylsilylphenyl)-phenylamino) pyrene in place of the compound (d-8).

A current test was conducted on the obtained organic EL device.

Voltage was 6.5 V, and current density was 10 mA/cm$^2$;
Luminous efficiency was 6 cd/A and 600 cd/m$^2$;
Wavelength of emission was 467 nm;
Initial luminance intensity for a measurement of lifetime was 1000 cd/m$^2$ (direct current); and
Lifetime was as short as 4,000 hours.

Table 2 below shows the results of Examples 1 to 6 and Comparatives 1 to 3.

TABLE 2

| | Dopant | Dopant Amount | Device Lifetime |
|---|---|---|---|
| Example 1 | d-15 | 5 mass % | 10000 h |
| Example 2 | d-28 | 5 mass % | 10000 h |
| Example 3 | d-9 | 5 mass % | 7000 h |
| Example 4 | d-8 | 5 mass % | 8500 h |
| Example 5 | d-8 | 7.5 mass % | 9500 h |
| Example 6 | d-8 | 10.0 mass % | 10000 h |

TABLE 2-continued

| | Dopant | Dopant Amount | Device Lifetime |
|---|---|---|---|
| Comparative 1 | 1,6-bis[di(3-pyridyl)amino] pyrene | 5 mass % | 1000 h |
| Comparative 2 | 3,8-dimethyl-1,6-bis(diphenylamino) pyrene | 5 mass % | 4500 h |
| Comparative 3 | 3,8-dimethyl-1,6-bis(diphenylamino) pyrene | 10.0 mass % | 4000 h |

(Modification)

The invention is not limited to the above-described exemplary embodiments or examples, but may adopt arrangements of the following typical organic EL devices as needed.

[Organic EL Device]

The organic EL device according to the aspect of the invention includes the organic layer between the anode and the cathode. This organic layer has an emitting portion. The organic layer may be structured such that the emitting portion is only singly layered, or such that a plurality of layers including the emitting layer are layered.

The organic EL device is configured such that the single-layered or multilayered organic thin film including at least the emitting layer is sandwiched between the cathode and the anode. At least one layer of the organic thin film contains the above-described diaminopyrene derivative as its sole component or as one component of a mixture.

Arrangement(s) of the organic EL device will be described below.

(1) Arrangement of Organic EL Device

The followings are representative arrangement examples of an organic EL device:

(a) anode/emitting layer/cathode;
(b) anode/hole injecting layer/emitting layer/cathode;
(c) anode/emitting layer/electron injecting layer/cathode;
(d) anode/hole injecting layer/emitting layer/electron injecting layer/cathode;
(e) anode/organic semiconductor layer/emitting layer/cathode;
(f) anode/organic semiconductor layer/electron blocking layer/emitting layer/cathode;
(g) anode/organic semiconductor layer/emitting layer/adhesion improving layer/cathode;
(h) anode/hole injecting layer/hole transporting layer/emitting layer/electron injecting layer/cathode;
(i) anode/insulating layer/emitting layer/insulating layer/cathode;
(j) anode/inorganic semiconductor layer/insulating layer/emitting layer/insulating layer/cathode;
(k) anode/organic semiconductor layer/insulating layer/emitting layer/insulating layer/cathode;
(l) anode/insulating layer/hole injecting layer/hole transporting layer/emitting layer/insulating layer/cathode; and
(m) anode/insulating layer/hole injecting layer/hole transporting layer/emitting layer/electron injecting layer/cathode.

Among the above, the arrangement (h) is preferably used.

(2) Light-Transmissive Substrate

The organic EL device is formed on a light-transmissive substrate. The light-transmissive plate, which supports the organic EL device, is preferably a smoothly-shaped substrate that transmits 50% or more of light in a visible region of 400 nm to 700 nm.

The light-transmissive plate is exemplarily a glass plate, a polymer plate or the like.

For the glass plate, materials such as soda-lime glass, barium/strontium-containing glass, lead glass, aluminosilicate glass, borosilicate glass, barium borosilicate glass and quartz can be used.

For the polymer plate, materials such as polycarbonate, acryl, polyethylene terephthalate, polyether sulfide and polysulfone can be used.

(3) Anode

The anode of the organic EL device is used for injecting holes into the hole injecting layer, the hole transporting layer or the emitting layer. It is effective that the anode has a work function of 4.5 eV or more. Exemplary materials for the anode are indium-tin oxide (ITO), tin oxide (NESA), indium zinc oxide (IZO), gold, silver, platinum and copper.

The anode may be made by forming a thin film from these electrode materials through a method such as vapor deposition or sputtering.

When light from the emitting layer is to be emitted through the anode as herein, the anode preferably transmits more than 10% of the light in the visible region. Although depending on the material of the anode, thickness of the anode is typically in a range of 10 nm to 1 µm, and preferably in a range of 10 to 200 nm.

(4) Emitting Layer

The emitting layer of the organic EL device has functions of: accepting, when an electrical field is applied, the holes injected by the anode or the hole injecting layer, or the electrons injected by the cathode or the electron injecting layer; transporting injected electric charges (the electrons and the holes) by the force of the electrical field; and providing a condition for recombination of the electrons and the holes to emit light.

Injectability of the holes may differ from that of the electrons and transporting capabilities of the hole and the electrons (represented by mobilities of the holes and the electrons) may differ from each other. It is preferable that either one of the charges is transported.

The thickness of the emitting layer is preferably in a range of 5 to 50 nm, more preferably in a range of 7 to 50 nm and most preferably in a range of 10 to 50 nm. The thickness below 5 nm may cause difficulty in forming the emitting layer and in controlling chromaticity, while the thickness above 50 nm may increase driving voltage.

As a method of forming the emitting layer, known methods such as vapor deposition, spin coating and an LB method may be employed.

(5) Hole Injecting/Transporting Layer (Hole Transporting Zone)

The hole injecting/transporting layer aids the injection of the holes into the emitting layer and transports the holes to the emitting region. In this layer, the hole mobility is large and ionization energy is usually as small as 5.5 eV or less. The hole injecting/transporting layer is preferably formed of a material capable of transporting the holes to the emitting layer at lower field intensity. In addition, the hole mobility thereof is preferably at least $1.0 \times 10^{-4}$ cm$^2$/V·second when an electric field of, for instance, $1.0 \times 10^4$ to $1.0 \times 10^6$ V/cm is applied.

Examples are a triazole derivative (see, for instance, the specification of U.S. Pat. No. 3,112,197), an oxadiazole derivative (see, for instance, the specification of U.S. Pat. No. 3,189,447), an imidazole derivative (see, for instance, JP-B-37-16096), a polyarylalkane derivative (see, for instance, the specifications of U.S. Pat. No. 3,615,402, No. 3,820,989 and No. 3,542,544, JP-B-45-555, JP-B-51-10983, JP-A-51-93224, JP-A-55-17105, JP-A-56-4148, JP-A-55-108667, JP-A-55-156953, and JP-A-56-36656), a pyrazoline derivative and a pyrazolone derivative (see, for instance, the specifications of U.S. Pat. No. 3,180,729 and No. 4,278,746, JP-A-55-88064, JP-A-55-88065, JP-49-105537, JP-A-55-51086, JP-A-56-80051, JP-A-56-88141, JP-A-57-45545, JP-A-54-112637 and JP-A-55-74546), a phenylenediamine derivative (see, for instance, the specification of U.S. Pat. No. 3,615,404, JP-B-51-10105, JP-B-46-3712, JP-B-47-25336, and JP-A-54-119925), an arylamine derivative (see, for instance, the specifications of U.S. Pat. No. 3,567,450, No. 3,240,597, No. 3,658,520, No. 4,232,103, No. 4,175,961 and No. 4,012,376, JP-B-49-35702, JP-B-39-27577, JP-A-55-144250, JP-A-56-119132 and JP-A-56-22437 and the specification of West Germany Patent No. 1,110,518), an amino-substituted chalcone derivative (see, for instance, the specification of U.S. Pat. No. 3,526,501), an oxazole derivative (disclosed in, for instance, the specification of U.S. Pat. No. 3,257,203), a styrylanthracene derivative (see, for instance, JP-A-56-46234), a fluorenone derivative (see, for instance, JP-A-54-110837), a hydrazone derivative (see, for instance, the specification of U.S. Pat. No. 3,717,462 and JP-A-54-59143, JP-A-55-52063, JP-A-55-52064, JP-A-55-46760, JP-A-57-11350, JP-A-57-148749 and JP-A-02-311591), a stilbene derivative (see, for instance, JP-A-61-210363, JP-A-61-228451, JP-A-61-14642, JP-A-61-72255, JP-A-62-47646, JP-A-62-36674, JP-A-62-10652, JP-A-62-30255, JP-A-60-93455, JP-A-60-94462, JP-A-60-174749 and JP-A-60-175052), a silazane derivative (see the specification of U.S. Pat. No. 4,950,950, a polysilane type (see JP-A-02-204996), an aniline-based copolymer (see JP-A-02-282263), and a conductive polymer oligomer (particularly, thiophene oligomer).

The material for the hole injecting/transporting layer, examples of which are as listed above, is preferably a porphyrin compound (disclosed in JP-A-63-295695 etc.), an aromatic tertiary amine compound or a styrylamine compound (see, for instance, the specification of U.S. Pat. No. 4,127,412, JP-A-53-27033, JP-A-54-58445, JP-A-55-79450, JP-A-55-144250, JP-A-56-119132, JP-A-61-295558, JP-A-61-98353 or JP-A-63-295695), particularly preferably an aromatic tertiary amine compound.

Additional examples are 4,4'-bis(N-(1-naphthyl)-N-phenylamino)biphenyl (hereinafter, abbreviated as NPD) having in the molecule two fused aromatic rings disclosed in U.S. Pat. No. 5,061,569, and 4,4',4"-tris(N-(3-methylphenyl)-N-phenylamino)triphenylamine (hereinafter, abbreviated as MTDATA) in which three triphenylamine units disclosed in JP-A-04-308688 are bonded in a starbust form.

Alternatively, inorganic compounds such as p-type Si and p-type SiC can also be used as the material for the hole injecting layer.

The hole injecting/transporting layer can be provided by forming the above-described compounds into thin films in accordance with a known method such as vacuum deposition, spin coating, casting and LB method.

The thickness of the hole injecting/transporting layer is not particularly limited, but is typically 5 nm to 5 μm.

(6) Electron Injecting/Transporting Layer (Electron Transporting Zone)

An electron injecting/transporting layer may be additionally provided between the organic emitting layer and the cathode. The electron injecting/transporting layer, which aids injection of the electrons into the emitting layer, has a high electron mobility.

In organic EL devices, where electrodes (cathodes in this example) reflect the emitted light, the emitted light directly exited from the anodes and the emitted light exited after reflection by the electrodes are known to interfere with each other. In order to efficiently utilize the interference effect, the thickness of the electron transporting layer is suitably determined in a range of several nanometers to several micrometers. Particularly when the electron transporting layer is formed thick, its electron mobility is preferably at least $10^{-5}$ cm$^2$/Vs or more under the application of an electrical field of $10^4$ to $10^6$ V/cm for prevention of increase in voltage.

As a material for the electron injecting/transporting layer, 8-hydroxyquinoline or a metal complex of its derivative is preferable. An example of the 8-hydroxyquinoline or the metal complex of its derivative is a metal chelate oxinoid compound containing a chelate of oxine (typically 8-quinolinol or 8-hydroxyquinoline). For instance, Alq having Al as the central metal is usable as the electron injecting/transporting layer.

Oxadiazole derivatives represented by the following formulae are also preferable as the material for the electron injecting (transporting) layer.

[Chemical Formula 40]

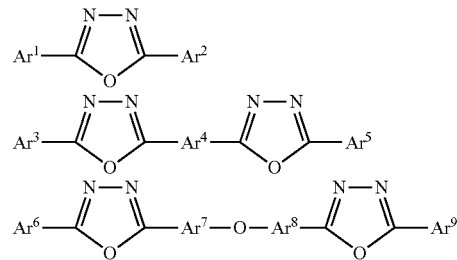

In the formulae, Ar$^1$, Ar$^2$, Ar$^3$, Ar$^5$, Ar$^6$ and Ar$^9$ each represent a substituted or unsubstituted aryl group, which may be mutually the same or different. Ar$^4$, Ar$^7$ and Ar$^8$ each represent a substituted or unsubstituted arylene group, which may be mutually the same or different.

Examples of the aryl group are a phenyl group, biphenyl group, anthranil group, perylenyl group and pyrenyl group. Examples of the arylene group are a phenylene group, naphthylene group, biphenylene group, anthranylene group, perylenylene group and pyrenylene group. Examples of the substituent therefor are an alkyl group having 1 to 10 carbon atoms, alkoxy group having 1 to 10 carbon atoms and cyano group. Such an electron transport compound is preferably a compound that can be favorably formed into thin films.

Examples of the electron transport compounds are as follows.

[Chemical Formula 41]

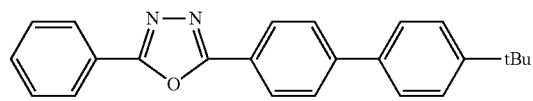

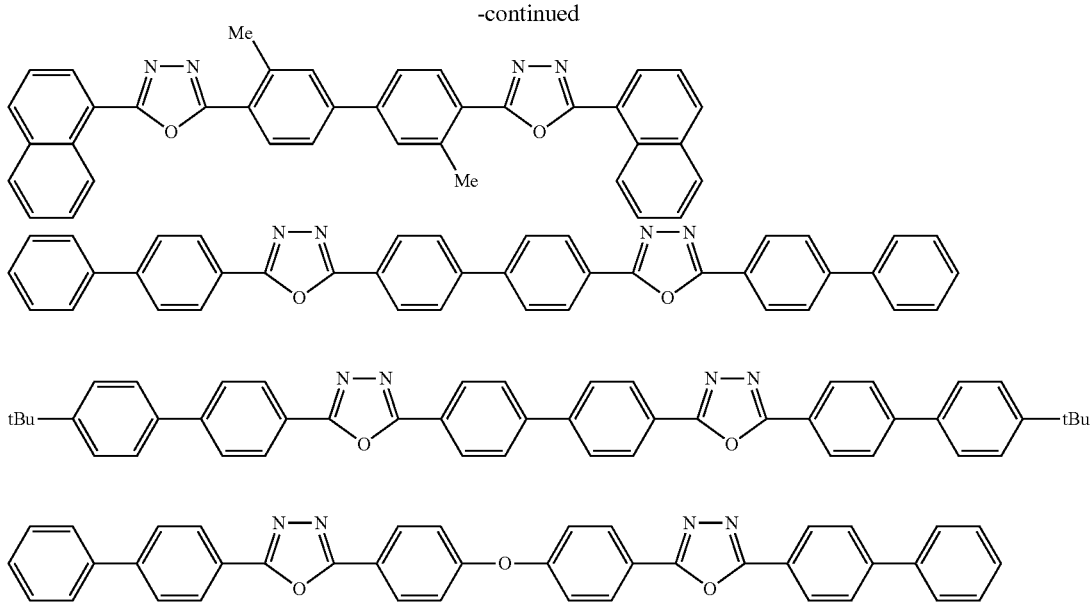

Nitrogen-containing heterocyclic derivatives represented by the following formulae are also preferable as the material for the electron injecting (transporting) layer.

[Chemical Formula 42]

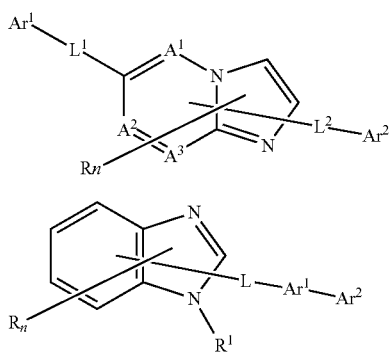

In the formulae: $A^1$ to $A^3$ each represent a nitrogen atom or carbon atom; R represents a substituted or unsubstituted aryl group having 6 to 60 carbon atoms, substituted or unsubstituted heteroaryl group having 3 to 60 carbon atoms, alkyl group having 1 to 20 carbon atoms, haloalkyl group having 1 to 20 carbon atoms or an alkoxy group having 1 to 20 carbon atoms; and n represents an integer of 0 to 5. When n is an integer of 2 or more, the plurality of R may be mutually the same or different.

Further, the adjoining R groups may be bonded together to form a substituted or unsubstituted carbocyclic aliphatic ring or a substituted or unsubstituted carbocyclic aromatic ring.

$Ar^1$ represents a substituted or unsubstituted aryl group having 6 to 60 carbon atoms or a substituted or unsubstituted heteroaryl group having 3 to 60 carbon atoms while $Ar^2$ represents a hydrogen atom, an alkyl group having 1 to 20 carbon atoms, a haloalkyl group having 1 to 20 carbon atoms, an alkoxy group having 1 to 20 carbon atoms, a substituted or unsubstituted aryl group having 6 to 60 carbon atoms or a substituted or unsubstituted heteroaryl group having 3 to 60 carbon atoms.

However, either one of $Ar^1$ and $Ar^2$ represents a substituted or unsubstituted fused ring group having 10 to 60 carbon atoms or a substituted or unsubstituted hetero fused ring group having 3 to 60 carbon atoms.

$L^1$ and $L^2$ each represent a single bond, substituted or unsubstituted fused ring having 6 to 60 carbon atoms, substituted or unsubstituted hetero fused ring having 3 to 60 carbon atoms or substituted or unsubstituted fluorenylene group.

$$HAr-L^1-Ar^1—Ar^2$$ [Chemical Formula 43]

In the formula: HAr represents a substituted or unsubstituted nitrogen-containing heterocycle having 3 to 40 carbon atoms; $L^1$ represents a single bond, substituted or unsubstituted arylene group having 6 to 60 carbon atoms, substituted or unsubstituted heteroarylene group having 3 to 60 carbon atoms or substituted or unsubstituted fluorenylene group; $Ar^1$ represents a substituted or unsubstituted divalent aromatic hydrocarbon group having 6 to 60 carbon atoms; and $Ar^2$ represents a substituted or unsubstituted aryl group having 6 to 60 carbon atoms or substituted or unsubstituted heteroaryl group having 3 to 60 carbon atoms.

Silacyclopentadiene derivatives represented by the following formula are also preferable as the material for the electron injecting (transporting) layer.

[Chemical Formula 44]

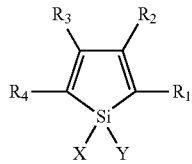

In the formula, X and Y each independently represent a saturated or unsaturated hydrocarbon group having 1 to 6 carbon atoms, alkoxy group, alkenyloxy group, alkynyloxy group, hydroxy group, substituted or unsubstituted aryl group or substituted or unsubstituted heterocycle. Alternatively, X and Y may be bonded together to form a saturated or unsaturated ring.

$R_1$ to $R_4$ each independently represent hydrogen, halogen, substituted or unsubstituted alkyl group having 1 to 6 carbon atoms, alkoxy group, aryloxy group, perfluoroalkyl group, amino group, alkylcarbonyl group, arylcarbonyl group, alkoxycarbony group, aryloxycarbonyl group, azo group, alkylcarbonyloxy group, arylcarbonyloxy group, alkoxycarbonyloxy group, aryloxycarbonyloxy group, sulfinyl group, sulfonyl group, sulfanyl group, silyl group, carbamoyl group, aryl group, heterocyclic group, alkenyl group, alkynyl group, nitro group, formyl group, nitroso group, formyloxy group, isocyano group, cyanate group, isocyanate group, thiocyanate group, isothiocyanate group or cyano group. Alternatively, an adjoining set of $R_1$ to $R_4$ may form a structure in which substituted or unsubstituted rings are fused.

Silacyclopentadiene derivatives represented by the following formula are also preferable as the material for the electron injecting (transporting) layer.

[Chemical Formula 45]

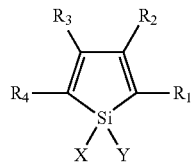

In the formula, X and Y each independently represent a saturated or unsaturated hydrocarbon group having 1 to 6 carbon atoms, alkoxy group, alkenyloxy group, alkynyloxy group, hydroxy group, substituted or unsubstituted aryl group or substituted or unsubstituted heterocycle. Alternatively, X and Y may be bonded together to form a saturated or unsaturated ring.

$R_1$ to $R_4$ each independently represent hydrogen, halogen, substituted or unsubstituted alkyl group having 1 to 6 carbon atoms, alkoxy group, aryloxy group, perfluoroalkyl group, amino group, alkylcarbonyl group, arylcarbonyl group, alkoxycarbony group, aryloxycarbonyl group, azo group, alkylcarbonyloxy group, arylcarbonyloxy group, alkoxycarbonyloxy group, aryloxycarbonyloxy group, sulfinyl group, sulfonyl group, sulfanyl group, silyl group, carbamoyl group, aryl group, heterocyclic group, alkenyl group, alkynyl group, nitro group, formyl group, nitroso group, formyloxy group, isocyano group, cyanate group, isocyanate group, thiocyanate group, isothiocyanate group or cyano group. Alternatively, an adjoining set of $R_1$ to $R_4$ may form a structure in which substituted or unsubstituted rings are fused.

However, when $R^1$ and $R^4$ are phenyl groups, X and Y are not an alkyl group and phenyl group. When $R^1$ and $R^4$ are thienyl groups, X and Y being a monovalent hydrocarbon group is not concurrent with $R^2$ and $R^3$ being an alkyl group, aryl group, alkenyl group or an aliphatic group in which $R^2$ and $R^3$ are bonded together to form a ring. When $R^1$ and $R^4$ are silyl groups, $R^2$, $R^3$, X and Y are not each independently a monovalent hydrocarbon having 1 to 6 carbon atoms or hydrogen atom. When $R^1$ and $R^2$ form a structure in which benzene rings are fused, X and Y are not an alkyl group and phenyl group.

Borane derivatives represented by the following formula are also preferable as the material for the electron injecting (transporting) layer.

[Chemical Formula 46]

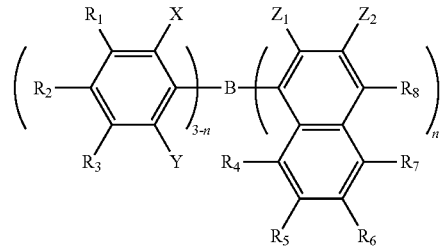

In the formula: $R_1$ to $R_8$ and $Z_2$ each independently represent a hydrogen atom, saturated or unsaturated hydrocarbon group, aromatic group, heterocyclic group, substituted amino group, substituted boryl group, alkoxy group or aryloxy group; X, Y and $Z_1$ each independently represent a saturated or unsaturated hydrocarbon group, aromatic group, heterocyclic group, substituted amino group, alkoxy group or aryloxy group; substituents of $Z_1$ and $Z_2$ may be bonded to form a fused ring; n represents an integer of 1 to 3; and where when n is 2 or more, $Z_1$ may be different and $Z_2$ may be different.

However, the above formula does not cover a case where n is 1, X, Y and $R_2$ are the methyl group and $R_8$ is the hydrogen atom or the substituted boryl group or a case where n is 3 and $Z_1$ is the methyl group.

Gallium complexes represented by the following formula are also preferable as the material for the electron injecting (transporting) layer.

[Chemical Formula 47]

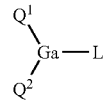

In this formula, $Q^1$ and $Q^2$ each independently represent a ligand represented by the formula below. L represents a ligand which may be: a halogen atom; a substituted or unsubstituted alkyl group; a substituted or unsubstituted cycloalkyl group; a substituted or unsubstituted aryl group; a substituted or unsubstituted heterocyclic group; those represented by —$OR^1$ ($R^1$ representing a hydrogen atom, a substituted or unsubstituted alkyl group, a substituted or unsubstituted cycloalkyl group, a substituted or unsubstituted aryl group or a substituted or unsubstituted heterocyclic group); or those represented by —O—Ga-$Q^3(Q^4)$ ($Q^3$ and $Q^4$ being the same as $Q^1$ and $Q^2$).

In the formula, $Q^1$ to $Q^4$ each represent a residue represented by the formula below, which may be exemplified by, but not limited to, a quinoline residue such as 8-hydroxyquinoline and 2-methyl-8-hydroxyquinoline.

[Chemical Formula 48]

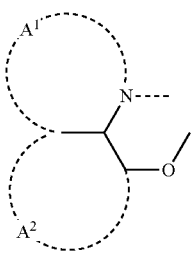

Rings $A^1$ and $A^2$ are substituted or unsubstituted aryl rings bonded to each other or a heterocyclic structure.

The metal complex shown above exhibits a strong property as an n-type semiconductor and has a large electron injecting capability. In addition, since formation energy when forming the complex is low, bonding between the metal and the ligand in the formed metal complex becomes strong, thereby exhibiting a large fluorescence quantum efficiency as a luminescent material.

Examples of the substituent groups of Ring $A^1$ and Ring $A^2$ that form the ligands in the formula above are: halogen atoms such as chlorine, bromine, iodine and fluorine; substituted or unsubstituted alkyl groups such as a methyl group, an ethyl group, a propyl group, a butyl group, a sec-butyl group, a tert-butyl group, a pentyl group, a hexyl group, a heptyl group, an octyl group, a stearyl group and a trichloromethyl group; substituted or unsubstituted aryl groups such as a phenyl group, a naphthyl group a 3-methylphenyl group, a 3-methoxyphenyl group, a 3-fluorophenyl group, a 3-trichloromethylphenyl group, a 3-trifluoromethylphenyl group and a 3-nitrophenyl group; substituted or unsubstituted alkoxy groups such as a methoxy group, a n-butoxy group, a tert-butoxy group, a trichloromethoxy group, a trifluoroethoxy group, a pentafluoropropoxy group, a 2,2,3,3-tetrafluoropropoxy group, a 1,1,1,3,3,3-hexafluoro-2-propoxy group and a 6-(perfluorohethyl)hexyloxy group; substituted or unsubstituted aryloxy groups such as a phenoxy group, a p-nitrophenoxy group, a p-tert-butylphenoxy group, a 3-fluorophenoxy group, a pentafluorophenyl group and a 3-trifluoromethylphenoxy group; substituted or unsubstituted alkylthio groups such as a methylthio group, an ethylthio group, a tert-butylthio group, a hexylthio group, an octylthio group and a trifluoromethylthio group; substituted or unsubstituted arylthio groups such as a phenylthio group, a p-nitrophenylthio group, a p-tert-butylphenylthio group, a 3-fluorophenylthio group, a pentafluorophenylthio group and a 3-trifluoromethylphenylthio group; mono- or disubstituted amino groups such as a cyano group, a nitro group, an amino group, a methylamino group, a diethylamino group, an ethylamino group, a diethylamino group, a dipropylamino group, a dibutylamino group and a diphenylamino group; acylamino groups such as a bis(acetoxymethyl)amino group, a bis(acetoxyethyl)amino group, a bis(acetoxypropyl)amino group and a bis(acetoxybutyl)amino group; a hydroxyl group; a siloxy group; an acyl group; carbamoyl groups such as a methylcarbamoyl group, a dimethylcarbamoyl group, an ethylcarbamoyl group, a diethylcarbamoyl group, a propylcarbamoyl group, a butylcarbamoyl group, and a phenylcarbamoyl group; a carboxylic acid group; a sulfonic acid group; an imide group; cycloalkyl groups such as a cyclopentane group and a cyclohexyl group; aryl groups such as a phenyl group, a naphthyl group, a biphenyl group, an anthranil group, a phenanthryl group, a fluorenyl group and a pyrenyl group; and heterocyclic groups such as a pyridinyl group a pyrazinyl group, a pyrimidinyl group, a pyridazinyl group, a triazinyl group, an indolinyl group, a quinolinyl group, an acridinyl group, a pyrrolidinyl group, a dioxanyl group, a piperidinyl group, a morpholidinyl group, a piperazinyl group, a carbazolyl group, a furanyl group, a thiophenyl group, an oxazolyl group, an oxadiazolyl group, a benzoxazolyl group, a thiazolyl group, a thiadiazolyl group, a benzothiazolyl group, a triazolyl group, an imidazolyl group and a benzoimidazolyl group. In addition, the substituent groups listed above may be bonded to each other to form a 6-membered aryl ring or a heterocycle.

One of preferred embodiments of the organic EL device is a device containing a reductive dopant at a boundary between a region transporting the electrons or the cathode and the organic layer. The reductive dopant is defined as a substance capable of reducing an electron-transporting compound. Accordingly, as long as the substance has reducibility of a predetermined level, various substances may be usable. For instance, at least one substance selected from a group consisting of alkali metal, alkali earth metal, rare-earth metal, oxide of alkali metal, halide of alkali metal, oxide of alkali earth metal, halide of alkali earth metal, oxide of rare-earth metal, halide of rare-earth metal, organic complex of alkali metal, organic complex of alkali earth metal and organic complex of rare-earth metal can be favorably used.

Specifically, a preferable reductive dopant is at least one alkali metal selected from a group consisting of $L^1$ (work function: 2.9 eV), Na (work function: 2.36 eV), K (work function: 2.28 eV), Rb (work function: 2.16 eV) and Cs (work function: 1.95 eV), or at least one alkali earth metal selected from a group consisting of Ca (work function: 2.9 eV), Sr (work function: 2.0 to 2.5 eV) and Ba (work function: 2.52 eV). The substances having the work function of 2.9 eV or less are particularly preferable. Among the above, a more preferable reductive dopant is at least one alkali metal selected from a group consisting of K, Rb and Cs. A further more preferable reductive dopant is Rb or Cs. The most preferable reductive dopant is Cs. Since the above alkali metals have particularly high reducibility, addition of a relatively small amount of these alkali metals to an electron injecting zone can enhance luminance intensity and lifetime of the organic EL device. As a reductive dopant having work function of 2.9 eV or less, a combination of two or more of the alkali metals is also preferable. Particularly, a combination including Cs (e.g., Cs and Na, Cs and K, Cs and Rb, or Cs, Na and K) is preferable. A reductive dopant containing Cs in a combining manner can efficiently exhibit reducibility. Addition of the reductive dopant to the electron injecting zone can enhance luminance intensity and lifetime of the organic EL device.

An electron injecting layer formed from an insulator or semiconductor may be provided between the cathode and the organic layer. Such an insulator or semiconductor can effectively prevent a current leak, thereby enhancing electron injectability of the electron injecting layer. As the insulator, it is preferable to use at least one metal compound selected from a group consisting of an alkali metal chalcogenide, an alkali earth metal chalcogenide, a halogenide of alkali metal and a halogenide of alkali earth metal. By forming the electron injecting layer from the alkali metal chalcogenide or the like, the electron injecting capability can preferably be further enhanced. Specifically, preferable examples of the alkali metal chalcogenide are $Li_2O$, $K_2O$, $Na_2S$, $Na_2Se$ and $Na_2O$, while preferable example of the alkali earth metal chalcogenide are CaO, BaO, SrO, BeO, BaS and CaSe. Preferable examples of the halogenide of the alkali metal are LiF, NaF, KF, LiCl, KCl and NaCl. Preferable examples of the halogenide of the alkali earth metal are fluorides such as $CaF_2$, $BaF_2$, $SrF_2$, $MgF_2$ and $BeF_2$, and halogenides other than the fluoride.

Examples of the semiconductor are one of or a combination of two or more of an oxide, a nitride or an oxidized nitride containing at least one element selected from Ba, Ca, Sr, Yb, Al, Ga, In, Li, Na, Cd, Mg, Si, Ta, Sb and Zn. An inorganic compound for forming the electron transporting layer is preferably a microcrystalline or amorphous semiconductor film. When the electron transporting layer is formed of such insulator film, more uniform thin film can be formed, thereby reducing pixel defects such as a dark spot. Examples of such an inorganic compound are the above-described alkali metal chalcogenide, alkali earth metal chalcogenide, halogenide of the alkali metal and halogenide of the alkali earth metal.

(7) Cathode

In order to inject the electrons into the electron injecting/transporting layer or the emitting layer, a material whose work function is small (4 eV or less) is used as an electrode material for the cathode. Examples of the material are metals, alloys, electrically conductive compounds and mixtures thereof. Examples of the electrode material are sodium, a sodium-potassium alloy, magnesium, lithium, a magnesium-silver alloy, aluminium-aluminium oxide, an aluminium-lithium alloy, indium and rare earth metal.

The cathode may be made by forming a thin film from these electrode materials through a method such as vapor deposition or sputtering.

When light from the emitting layer is to be emitted through the cathode, the cathode preferably transmits more than 10% of the light in the visible region.

The sheet resistance as the cathode is preferably several hundreds Ω/square or less, and the thickness of the film is typically 10 nm to 1 μm, preferably 50 to 200 nm.

(8) Insulating Layer

Since the electrical field is applied to ultra thin films in the organic EL device, pixel defects resulted from leak or short circuit likely occur. In order to prevent such defects, it is preferable to interpose an insulating thin film layer between a pair of electrodes.

Examples of a material used for the insulating layer are aluminum oxide, lithium fluoride, lithium oxide, cesium fluoride, cesium oxide, magnesium oxide, magnesium fluoride, calcium oxide, calcium fluoride, aluminium nitride, titanium oxide, silicon oxide, germanium oxide, silicon nitride, boron nitride, molybdenum oxide, ruthenium oxide and vanadium oxide.

Mixtures or laminates thereof may also be used.

(9) Manufacturing Method of Organic EL Device

The organic EL device can be manufactured by forming the anode, the emitting layer, the hole injecting layer (as necessary), the electron injecting layer (as necessary) and the cathode form the materials listed above by the above-described formation methods. Alternatively, the organic EL device can be also manufactured in the reverse order of the above (i.e., from the cathode to the anode).

The following is a manufactured example of the organic EL device in which the anode, the hole injecting layer, the emitting layer, the electron injecting layer and the cathode are sequentially formed on the light-transmissive substrate.

A thin film made of anode material is initially formed on a suitable transparent substrate to be 1 μm thick or less, more preferably 10 to 200 nm thick, by a method such as vapor deposition or sputtering, through which an anode is manufactured.

Then, a hole injecting layer is provided onto the anode.

The hole injecting layer can be formed by a method such as vacuum deposition, spin coating, casting and LB method. The thickness of the hole injecting/transporting layer may be suitably determined in a range of 5 nm to 5 μm.

Next, an emitting layer, which is to be formed on the hole injecting layer, can be formed by forming a desirable organic emitting material into film by dry processing (representative example: vacuum deposition) or by wet processing such as spin coating or casting.

Then, an electron injecting layer is formed on the emitting layer.

The electron injecting layer may be exemplarily formed by vacuum deposition.

Lastly, a cathode is layered, and the organic EL device is obtained.

The cathode is formed of metal by vapor deposition or sputtering.

However, in order to protect the underlying organic layer from damages at the time of film forming, vacuum deposition is preferable.

A method of forming each of the layers in the organic EL device 1 is not particularly limited.

Conventionally-known methods such as vacuum deposition and spin coating are usable. Specifically, the organic thin-film layer may be formed by a conventional coating method such as vacuum deposition, molecular beam epitaxy (MBE method) and coating methods using a solution such as a dipping, spin coating, casting, bar coating, roll coating and ink jetting.

Although the thickness of each organic thin film of the organic EL device is not particularly limited, the thickness is typically preferably in a range of several nanometers to 1 μm because an excessively-thinned film is likely to entail defects such as a pin hole while an excessively-thickened film requires high voltage to be applied and deteriorates efficiency.

When a direct current is applied to the organic EL device, the emission can be observed by applying a voltage of 5 to 40V with the anode having the positive polarity and the cathode having the negative polarity. When the voltage is applied with the inversed polarity, no current flows, so that the emission is not generated. When an alternating current is applied, the uniform emission can be observed only when the anode has the positive polarity and the cathode has the negative polarity. A waveform of the alternating current to be applied may be suitably selected.

The invention claimed is:

1. A diaminopyrene derivative for use as an emitting material for an organic EL device, represented by a formula (1) below,

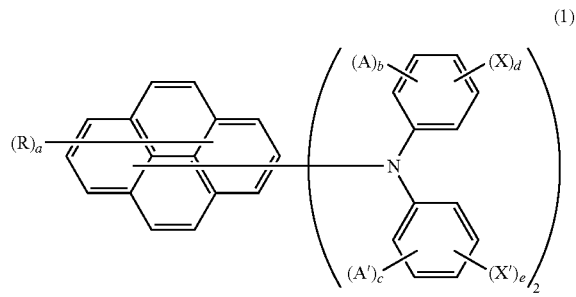

where: R represents a substituted or unsubstituted alkyl group having 1 to 20 carbon atoms or a fluorine atom; a represents an integer of 1 to 9; when a is 2 or more, the plurality of R are allowed to be mutually the same or different;

A and A' each independently represent a hydrogen atom, substituted or unsubstituted alkyl group having 1 to 20 carbon atoms, substituted or unsubstituted aryl group having 5 to 25 carbon atoms, substituted or unsubstituted aralkyl group having 6 to 25 carbon atoms, substituted or unsubstituted cycloalkyl group having 3 to 25 carbon atoms, substituted or unsubstituted alkoxyl group having 1 to 20 carbon atoms, substituted or unsubstituted aryloxy group having 5 to 25 carbon atoms, substituted or unsubstituted arylamino group having 5 to 25 carbon atoms, substituted or unsubstituted alkylamino group having 1 to 20 carbon atoms, fluorine atom or cyano group;

b and c each represent an integer of 1 to 5 while $b+c \leqq 9$ is satisfied; when b is 2 or more, the plurality of A are allowed to be mutually the same or different and to be bonded together to form a saturated or unsaturated ring; when c is 2 or more, the plurality of A' are allowed to be mutually the same or different and to be bonded together to form a saturated or unsaturated ring;

X and X' each independently represent a substituent containing at least one of Ge, P, B and Si;

d and e each represent an integer of 0 to 5 while $d+e \geqq 1$ is satisfied; when d is 2 or more, the plurality of X are allowed to be mutually the same or different and to be bonded together to form a saturated or unsaturated ring; and when e is 2 or more, the plurality of X' are allowed to be mutually the same or different and to be bonded together to form a saturated or unsaturated ring.

2. The diaminopyrene derivative for use as an emitting material for an organic EL device according to claim 1, the diaminopyrene derivative being a compound represented by a formula (2) below among compounds represented by the formula (1),

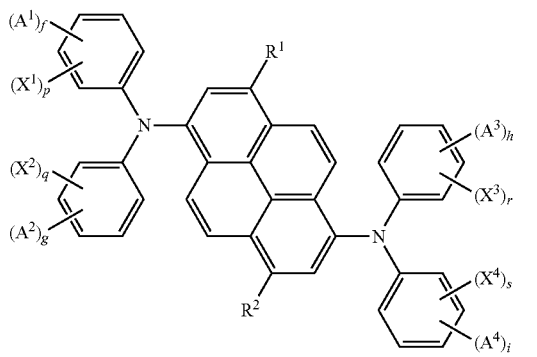

(2)

where: $R^1$ and $R^2$ each independently represent a substituted or unsubstituted alkyl group having 1 to 20 carbon atoms, or a fluorine atom;

$A^1, A^2, A^3$ and $A^4$ each independently represent a hydrogen atom, substituted or unsubstituted alkyl group having 1 to 20 carbon atoms, substituted or unsubstituted aryl group having 5 to 25 carbon atoms, substituted or unsubstituted aralkyl group having 6 to 25 carbon atoms, substituted or unsubstituted cycloalkyl group having 3 to 25 carbon atoms, substituted or unsubstituted alkoxyl group having 1 to 20 carbon atoms, substituted or unsubstituted aryloxy group having 5 to 25 carbon atoms, substituted or unsubstituted arylamino group having 5 to 25 carbon atoms, substituted or unsubstituted alkylamino group having 1 to 20 carbon atoms or cyano group;

f, g, h and i each represent an integer of 1 to 5 while $f+g+h+i \leqq 19$ is satisfied; when f is 2 or more, the plurality of $A^1$ are allowed to be mutually the same or different and to be bonded together to form a saturated or unsaturated ring; when g is 2 or more, the plurality of $A^2$ are allowed to be mutually the same or different and to be bonded together to form a saturated or unsaturated ring; when h is 2 or more, the plurality of $A^3$ are allowed to be mutually the same or different and to be bonded together to form a saturated or unsaturated ring; when i is 2 or more, the plurality of $A^4$ are allowed to be mutually the same or different and to be bonded together to form a saturated or unsaturated ring;

$X^1, X^2, X^3$ and $X^4$ each independently represent a substituent containing at least one of Ge, P, B and Si;

p, q, r and s each represent an integer of 0 to 5 while $p+q+r+s \geqq 1$ is satisfied; when p is 2 or more, the plurality of $X^1$ are allowed to be mutually the same or different and to be bonded together to form a saturated or unsaturated ring; when q is 2 or more, the plurality of $X^2$ are allowed to be mutually the same or different and to may be bonded together to form a saturated or unsaturated ring; when r is 2 or more, the plurality of $X^3$ are allowed to be mutually the same or different and to be bonded together to form a saturated or unsaturated ring; and when s is 2 or more, the plurality of $X^4$ are allowed to be mutually the same or different and to be bonded together to form a saturated or unsaturated ring.

3. The diaminopyrene derivative for use as an emitting material for an organic EL device according to claim 2, wherein $X^1, X^2, X^3$ and $X^4$ in the formula (2) each independently represent a substituent represented by a formula (3) below, $$-M(-R^3)_3 \qquad (3)$$

where: M represents Ge or Si;

$R^3$ represents hydrogen, a substituted or unsubstituted alkyl group having 1 to 20 carbon atoms, substituted or unsubstituted aryl group having 5 to 25 carbon atoms, substituted or unsubstituted aralkyl group having 6 to 25 carbon atoms, substituted or unsubstituted cycloalkyl group having 3 to 25 carbon atoms, substituted or unsubstituted alkoxyl group having 3 to 20 carbon atoms, substituted or unsubstituted aryloxy group having 5 to 25 carbon atoms, substituted or unsubstituted arylamino group having 5 to 20 carbon atoms, substituted or unsubstituted alkylamino group having 1 to 20 carbon atoms or cyano group; and the plurality of $R^3$ are allowed to be mutually the same or different and to be bonded together to form a saturated or unsaturated ring.

4. The diaminopyrene derivative for use as an emitting material for an organic EL device according to claim 2, wherein $X^1, X^2, X^3$ and $X^4$ in the formula (2) each independently represent a substituent represented by a formula (4) below, $$-M(-R^4)_2 \qquad (4)$$

where: M represents P or B;

R⁴ represents hydrogen, a substituted or unsubstituted alkyl group having 1 to 20 carbon atoms, substituted or unsubstituted aryl group having 5 to 25 carbon atoms, substituted or unsubstituted aralkyl group having 6 to 25 carbon atoms, substituted or unsubstituted cycloalkyl group having 3 to 25 carbon atoms, substituted or unsubstituted alkoxyl group having 3 to 20 carbon atoms, substituted or unsubstituted aryloxy group having 5 to 25 carbon atoms, substituted or unsubstituted arylamino group having 5 to 20 carbon atoms, substituted or unsubstituted alkylamino group having 1 to 20 carbon atoms or cyano group; and the plurality of R⁴ are allowed to be mutually the same or different and to be bonded together to form a saturated or unsaturated ring.

5. The diaminopyrene derivative for use as an emitting material for an organic EL device according to claim 3, wherein M in the formula (3) is Si.

6. The diaminopyrene derivative for use as an emitting material for an organic EL device according to claim 2, wherein at least either one of $R^1$ and $R^2$ in the formula (2) is a substituted or unsubstituted alkyl group having 1 to 20 carbon atoms.

7. A diaminopyrene derivative for use as an emitting material for an organic EL device, represented by a formula (5) below,

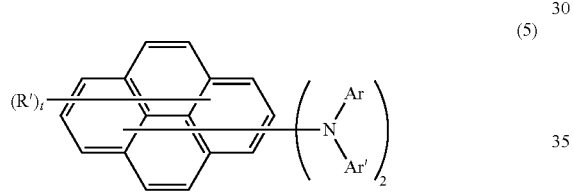

(5)

where: R' represents a substituted or unsubstituted alkyl group having 1 to 20 carbon atoms or a fluorine atom; t represents an integer of 1 to 9; when t is 2 or more, the plurality of R' are allowed to be mutually the same or different;

Ar and Ar' each independently represent a substituted or unsubstituted alkyl group having 1 to 20 carbon atoms, substituted or unsubstituted aryl group having 5 to 25 carbon atoms, substituted or unsubstituted aralkyl group having 6 to 25 carbon atoms, substituted or unsubstituted cycloalkyl group having 3 to 25 carbon atoms, substituted or unsubstituted alkoxyl group having 1 to 20 carbon atoms, substituted or unsubstituted aryloxy group having 5 to 25 carbon atoms, substituted or unsubstituted arylamino group having 5 to 25 carbon atoms, substituted or unsubstituted alkylamino group having 1 to 20 carbon atoms or substituted or unsubstituted nitrogen-containing heterocyclic group having 5 to 25 atoms for forming the ring; and two Ar and two Ar' are allowed be mutually the same or different, on a condition that at least one of Ar and Ar' is a substituted or unsubstituted nitrogen-containing heterocyclic group having 5 to 25 ring atoms.

8. The diaminopyrene derivative for use as an emitting material for an organic EL device according to claim 7, the diaminopyrene derivative being a compound represented by a formula (6) below among compounds represented by the formula (5),

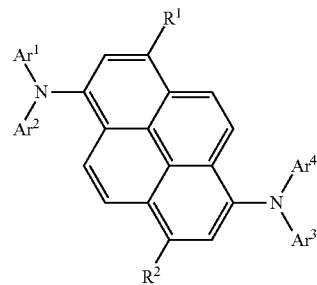

(6)

where: $R^1$ and $R^2$ each independently represent a substituted or unsubstituted alkyl group having 1 to 20 carbon atoms or a fluorine atom; and $Ar^1$, $Ar^2$, $Ar^3$ and $Ar^4$ each independently represent a substituted or unsubstituted alkyl group having 1 to 20 carbon atoms, substituted or unsubstituted aryl group having 5 to 25 carbon atoms, substituted or unsubstituted aralkyl group having 6 to 25 carbon atoms, substituted or unsubstituted cycloalkyl group having 3 to 25 carbon atoms, substituted or unsubstituted alkoxyl group having 1 to 20 carbon atoms, substituted or unsubstituted aryloxy group having 5 to 25 carbon atoms, substituted or unsubstituted arylamino group having 5 to 25 carbon atoms, substituted or unsubstituted alkylamino group having 1 to 20 carbon atoms or substituted or unsubstituted nitrogen-containing heterocyclic group having 5 to 25 atoms for forming the ring, on a condition that at least one of $Ar^1$, $Ar^2$, $Ar^3$ and $Ar^4$ is a substituted or unsubstituted nitrogen-containing heterocyclic group having 5 to 25 ring atoms.

9. The diaminopyrene derivative for use as an emitting material for an organic EL device according to claim 8, wherein at least either one of $R^1$ and $R^2$ in the formula (6) is a substituted or unsubstituted alkyl group having 1 to 20 carbon atoms.

10. The diaminopyrene derivative for use as an emitting material for an organic EL device according to claim 1, the diaminopyrene derivative being used as a dopant of the emitting layer of the organic EL device, the emitting layer containing a host and the dopant material.

11. An organic EL device, comprising:

an organic layer provided between a cathode and an anode, the organic layer containing the diaminopyrene derivative according to claim 1.

12. An organic EL device, comprising:

an emitting layer provided between a cathode and an anode, the emitting layer containing the diaminopyrene derivative according to claim 1.

13. The organic EL device according to claim 12, wherein the emitting layer contains: the diaminopyrene derivative as a dopant; and a compound having a central anthracene skeleton represented by a formula (7) below as a host,

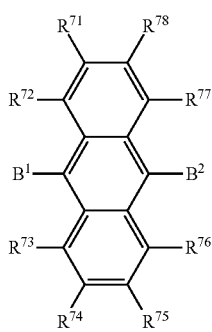

(7)

where: $B^1$ and $B^2$ each independently represent a group induced from a substituted or unsubstituted aromatic ring having 6 to 20 carbon atoms for forming the ring;

the aromatic ring is allowed to be substituted by 1 or more substituent;

the substituent is selected from a substituted or unsubstituted aryl group having 6 to 50 carbon atoms for forming the ring, substituted or unsubstituted alkyl group having 1 to 50 carbon atoms, substituted or unsubstituted cycloalkyl group having 3 to 50 carbon atoms, substituted or unsubstituted alkoxy group having 1 to 50 carbon atoms, substituted or unsubstituted aralkyl group having 6 to 50 carbon atoms, substituted or unsubstituted aryloxy group having 5 to 50 atoms for forming the ring, substituted or unsubstituted arylthio group having 5 to 50 atoms for forming the ring, substituted or unsubstituted alkoxycarbonyl group having 1 to 50 carbon atoms, substituted or unsubstituted silyl group, carboxyl group, halogen atom, cyano group, nitro group and hydroxyl group;

when the aromatic ring is substituted by 2 or more substituents, the substituents are allowed to be the same or different, an adjoining set of the substituents being allowed to be bonded together to form a saturated or unsaturated ring structure; and $R^{71}$ to $R^{78}$ are each independently selected from a hydrogen atom, substituted or unsubstituted aryl group having 6 to 50 carbon atoms for forming the ring, substituted or unsubstituted heteroaryl group having 5 to 50 atoms for forming the ring, substituted or unsubstituted alkyl group having 1 to 50 carbon atoms, substituted or unsubstituted cycloalkyl group having 3 to 50 carbon atoms, substituted or unsubstituted alkoxy group having 1 to 50 carbon atoms, substituted or unsubstituted aralkyl group having 6 to 50 carbon atoms, substituted or unsubstituted aryloxy group having 5 to 50 atoms for forming the ring, substituted or unsubstituted arylthio group having 5 to 50 atoms for forming the ring, substituted or unsubstituted alkoxycarbonyl group having 1 to 50 carbon atoms, substituted or unsubstituted silyl group, carboxyl group, halogen atom, cyano group, nitro group and hydroxyl group.

14. The organic EL device according to claim 13, wherein $B^1$ and $B^2$ in the formula (7) are mutually different.

15. The organic EL device according to claim 12, wherein the emitting layer contains: the diaminopyrene derivative as a dopant; and a compound having a central pyrene skeleton represented by a formula (8) below as a host,

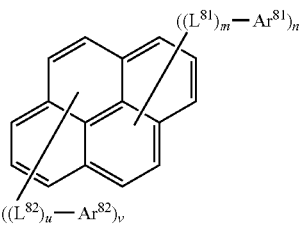

(8)

where: $Ar^{81}$ and $Ar^{82}$ each independently represent a substituted or unsubstituted aryl group having 6 to 50 carbon atoms for forming the ring;

$L^{81}$ and $L^{82}$ are each independently selected from a substituted or unsubstituted phenylene group, substituted or unsubstituted naphthalenylene group, substituted or unsubstituted fluorenylene group and substituted or unsubstituted dibenzo-sylolylene group;

m represents an integer of 0 to 2, n represents an integer of 1 to 4, u represents an integer of 0 to 2, and v represents an integer of 0 to 4; and $L^{81}$ or $Ar^{81}$ is bonded to the pyrene in one of 1st to 5th positions, and $L^{82}$ or $Ar^{82}$ is bonded to the pyrene in one of 6th to 10th positions.

16. The organic EL device according to claim 12, wherein the emitting layer contains: the diaminopyrene derivative as a dopant; and a compound having a triphenylamine skeleton represented by a formula (9) below as a host,

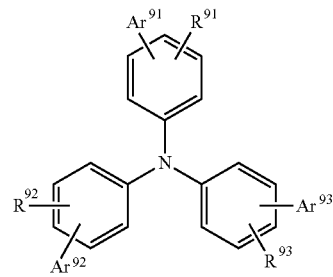

(9)

where: $Ar^{91}$, $Ar^{92}$ and $Ar^{93}$ are each independently selected from a group having an anthracene structure, a group having a phenanthrene structure and a group having a pyrene structure; and $R^{91}$, $R^{92}$ and $R^{93}$ each independently represent a hydrogen atom or a substituent.

17. The organic EL device according to claim 12, wherein the emitting layer contains the diaminopyrene derivative and a compound having a structure represented by a formula (10) below,

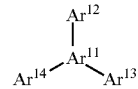

(10)

where: $Ar^{12}$, $Ar^{13}$ and $Ar^{14}$ each independently represent an aryl group having 6 to 50 carbon atoms for forming the ring;

the aryl group is allowed to be substituted by 1 or more substituent;

at least one of $Ar^{12}$, $Ar^{13}$, $Ar^{14}$ and substituents for these aryl groups has a ring-fused aryl structure having 10 to 20 carbon atoms for forming the ring or a ring-fused heteroaryl structure having 6 to 20 carbon atoms for forming the ring; and $Ar^{11}$ represents a trivalent group induced from an aromatic ring or hetero aromatic ring.

18. The diaminopyrene derivative for use as an emitting material for an organic EL device according to claim 7, the diaminopyrene derivative being used as a dopant of the emitting layer of the organic EL device, the emitting layer containing a host and the dopant.

19. An organic EL device, comprising:
an organic layer provided between a cathode and an anode, the organic layer containing the diaminopyrene derivative according to claim 7.

20. An organic EL device, comprising:
an emitting layer provided between a cathode and an anode,
the emitting layer containing the diaminopyrene derivative according to claim 7.

21. The organic EL device according to claim 20, wherein the emitting layer contains: the diaminopyrene derivative as a dopant; and a compound having a central anthracene skeleton represented by a formula (7) below as a host,

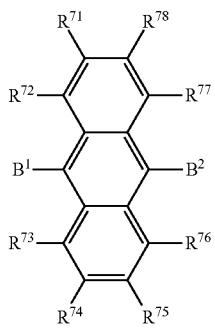

(7)

where: $B^1$ and $B^2$ each independently represent a group induced from a substituted or unsubstituted aromatic ring having 6 to 20 carbon atoms for forming the ring; the aromatic ring is allowed to be substituted by 1 or more substituent;
the substituent is selected from a substituted or unsubstituted aryl group having 6 to 50 carbon atoms for forming the ring, substituted or unsubstituted alkyl group having 1 to 50 carbon atoms, substituted or unsubstituted cycloalkyl group having 3 to 50 carbon atoms, substituted or unsubstituted alkoxy group having 1 to 50 carbon atoms, substituted or unsubstituted aralkyl group having 6 to 50 carbon atoms, substituted or unsubstituted aryloxy group having 5 to 50 atoms for forming the ring, substituted or unsubstituted arylthio group having 5 to 50 atoms for forming the ring, substituted or unsubstituted alkoxycarbonyl group having 1 to 50 carbon atoms, substituted or unsubstituted silyl group, carboxyl group, halogen atom, cyano group, nitro group and hydroxyl group;

when the aromatic ring is substituted by 2 or more substituents, the substituents are allowed to be the same or different, an adjoining set of the substituents being allowed to be bonded together to form a saturated or unsaturated ring structure; and $R^{71}$ to $R^{78}$ are each independently selected from a hydrogen atom, substituted or unsubstituted aryl group having 6 to 50 carbon atoms for forming the ring, substituted or unsubstituted heteroaryl group having 5 to 50 atoms for forming the ring, substituted or unsubstituted alkyl group having 1 to 50 carbon atoms, substituted or unsubstituted cycloalkyl group having 3 to 50 carbon atoms, substituted or unsubstituted alkoxy group having 1 to 50 carbon atoms, substituted or unsubstituted aralkyl group having 6 to 50 carbon atoms, substituted or unsubstituted aryloxy group having 5 to 50 atoms for forming the ring, substituted or unsubstituted arylthio group having 5 to 50 atoms for foiining the ring, substituted or unsubstituted alkoxycarbonyl group having 1 to 50 carbon atoms, substituted or unsubstituted silyl group, carboxyl group, halogen atom, cyano group, nitro group and hydroxyl group.

22. The organic EL device according to claim 21, wherein $B^1$ and $B^2$ in the formula (7) are mutually different.

23. The organic EL device according to claim 20, wherein the emitting layer contains: the diaminopyrene derivative as a dopant; and a compound having a central pyrene skeleton represented by a formula (8) below as a host,

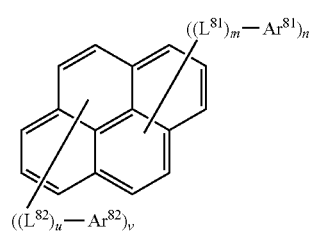

(8)

where: $Ar^{81}$ and $Ar^{82}$ each independently represent a substituted or unsubstituted aryl group having 6 to 50 carbon atoms for forming the ring;

$L^{81}$ and $L^{82}$ are each independently selected from a substituted or unsubstituted phenylene group, substituted or unsubstituted naphthalenylene group, substituted or unsubstituted fluorenylene group and substituted or unsubstituted dibenzo-sylolylene group;

m represents an integer of 0 to 2, n represents an integer of 1 to 4, u represents an integer of 0 to 2, and v represents an integer of 0 to 4; and $L^{81}$ or $Ar^{81}$ is bonded to the pyrene in one of 1st to 5th positions, and $L^{82}$ or $Ar^{82}$ is bonded to the pyrene in one of 6th to 10th positions.

24. The organic EL device according to claim 20, wherein the emitting layer contains: the diaminopyrene derivative as a dopant; and a compound having a triphenylamine skeleton represented by a formula (9) below as a host,

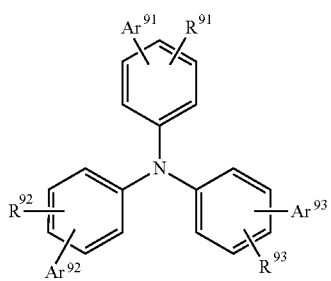

(9)

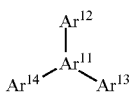

(10)

where: $Ar^{91}$, $Ar^{92}$ and $Ar^{93}$ are each independently selected from a group having an anthracene structure, a group having a phenanthrene structure and a group having a pyrene structure; and $R^{91}$, $R^{92}$ and $R^{93}$ each independently represent a hydrogen atom or a substituent.

25. The organic EL device according to claim 20, wherein the emitting layer contains the diaminopyrene derivative and a compound having a structure represented by a formula (10) below, where: $Ar^{12}$, $Ar^{13}$ and $Ar^{14}$ each independently represent an aryl group having 6 to 50 carbon atoms for forming the ring;

the aryl group is allowed to be substituted by 1 or more substituent;

at least one of $Ar^{12}$, $Ar^{13}$, $Ar^{14}$ and substituents for these aryl groups has a ring-fused aryl structure having 10 to 20 carbon atoms for forming the ring or a ring-fused heteroaryl structure having 6 to 20 carbon atoms for forming the ring; and $Ar^{11}$ represents a trivalent group induced from an aromatic ring or hetero aromatic ring.

* * * * *